US008697631B2

(12) United States Patent
Nakamura et al.

(10) Patent No.: US 8,697,631 B2
(45) Date of Patent: Apr. 15, 2014

(54) TMEM22 PEPTIDES AND VACCINES INCLUDING THE SAME

(75) Inventors: Yusuke Nakamura, Tokyo (JP); Takuya Tsunoda, Kanagawa (JP); Ryuji Ohsawa, Kanagawa (JP); Sachiko Yoshimura, Kanagawa (JP); Tomohisa Watanabe, Kanagawa (JP)

(73) Assignee: OncoTherapy Science, Inc., Kanagawa (JP)

( * ) Notice: Subject to any disclaimer, the term of this patent is extended or adjusted under 35 U.S.C. 154(b) by 0 days.

(21) Appl. No.: 13/515,656

(22) PCT Filed: Dec. 13, 2010

(86) PCT No.: PCT/JP2010/007228
§ 371 (c)(1),
(2), (4) Date: Aug. 20, 2012

(87) PCT Pub. No.: WO2011/074236
PCT Pub. Date: Jun. 23, 2011

(65) Prior Publication Data
US 2012/0308591 A1 Dec. 6, 2012

Related U.S. Application Data

(60) Provisional application No. 61/326,380, filed on Apr. 21, 2010, provisional application No. 61/287,650, filed on Dec. 17, 2009, provisional application No. 61/286,213, filed on Dec. 14, 2009.

(51) Int. Cl.
*C07K 7/06* (2006.01)
*A61K 38/08* (2006.01)
*G01N 33/53* (2006.01)

(52) U.S. Cl.
USPC ........... 514/1.1; 530/327; 530/328; 435/7.21; 435/7.24

(58) Field of Classification Search
None
See application file for complete search history.

(56) References Cited

FOREIGN PATENT DOCUMENTS

| CN | 101365806 A | 2/2009 |
|---|---|---|
| WO | 98/41539 A2 | 9/1998 |
| WO | 2004/024766 A1 | 3/2004 |
| WO | 2007/013575 A2 | 2/2007 |
| WO | 2007/072225 A2 | 6/2007 |
| WO | 2008/126413 A1 | 10/2008 |
| WO | 2009/069302 A1 | 6/2009 |
| WO | 2009/117196 A1 | 9/2009 |

OTHER PUBLICATIONS

Furuta, et al., "Silencing of *Peroxiredoxin* 2 and Aberrant Methylation of 33 CpG Islands in Putative Promoter Regions in Human Malignant Melanomas," *Cancer Res.*, vol. 66(12), pp. 6080-6086 (Jun. 15, 2006).
Kurome, et al., "Aureobasidins as New Inhibitors of P-Glycoprotein in Multidrug Resistant Tumor Cells," *J Antibiot.*, vol. 51(3), pp. 353-358 (Mar. 1998).
Kurome, et al., "Structure-Activity Relationship of Antifungal Aureobasidin A, Inhibitor of Sphingolipid Biosynthesis: Synthesis of New Active Aureobasidins against *Aspergillus fumigatus*," *Pept Sci.*, vol. 36, pp. 197-200 (1999).
Suda, et al., "Identification of *secernin* 1 as a novel immunotherapy target for gastric cancer using the expression profiles of cDNA microarray," *Cancer Sci.*, vol. 97(5), pp. 411-419 (May 2006).
Belli, et al. "Vaccination of Metastatic Melanoma Patients with Autologous Tumor-Derived Heat Shock Protein gp96-Peptide complexes: Clinical and Immunologic Findings," *J Clin Oncol.*, vol. 20(20), pp. 4169-4180 (Oct. 15, 2002).
Boon, "Tumor Antigens Recognized by Cytolytic T Lymphocytes: Present Perspectives for Specific Immunotherapy," *Int J Cancer*, vol. 54(2), pp. 177-180 (May 8, 1993).
Boon, et al., "Human Tumor Antigens Recognized by T Lymphocytes," *J Exp Med.*, vol. 183(3), pp. 725-729 (Mar. 1, 1996).
Butterfield, et al., "Generation of Human T-cell responses to an HLA-2.1 restricted Peptide Epitope Derived from α-Fetoprotein," *Cancer Res.*, vol. 59(13), pp. 3134-3142 (Jul. 1, 1999).
Coulie, et al., "Cytolytic T-cell Responses of cancer patients vaccinated with a MAGE antigen," *Immunol Rev.*, vol. 188, pp. 33-42 (Oct 2002).
Dobashi, et al., Involvement of TMEM22 overexpression in the growth of renal cell carcinoma cells, *Oncol Rep.*, vol. 21(2), pp. 305-312 (Feb. 2009).
Fujie, et al., "A Mage-1-Encoded HLA-A24-Binding Synthetic Peptide Induces Specific Anti-tumor Cytotoxic T Lymphocytes," *Int J Cancer*, vol. 80(2), pp. 169-172 (Jan. 18, 1999).
Harris, "Structure and Function of the p53 Tumor Suppressor Gene: Clues for Rational Cancer Therapeutic Strategies," *J Natl Cancer Inst.*, vol. 88(20), pp. 1442-1455 (Oct. 16, 1996).
Hirota, et al., Genome-wide gene expression profiles of clear cell renal cell carcinoma: Identification of molecular targets for treatment of renal cell carcinoma, *Int J Oncol.*, vol. 29(4), pp. 799-827 (Oct. 2006).
Kikuchi, et al., "Identification of a Sart-1-Derived Peptide Capable of Inducing HLA-A24-Restricted and Tumor-Specific Cytotoxic T Lymphocytes," *Int J Cancer*, vol. 81(3), pp. 459-466 (May 5, 1999).
Oiso, et al., "A Newly Identified Mage-3-Derived Epitope Recognized by HLA-A24-Restricted Cytotoxic T Lymphocytes," *Int J Cancer*, vol. 81(3), pp. 387-394 (May 5, 1999).

(Continued)

*Primary Examiner* — Prema Mertz
(74) *Attorney, Agent, or Firm* — Kilpatrick Townsend & Stockton LLP

(57) ABSTRACT

Isolated peptides composed of the amino acid sequence of SEQ ID NO: 33 or fragments thereof that bind to HLA antigens and have cytotoxic T lymphocyte (CTL) inducibility and thus are suitable for use in the context of cancer immunotherapy, more particularly cancer vaccines are described herein. The present invention further provides peptides that include one, two, or several amino acid insertions, substitutions or additions to the aforementioned peptides or fragments, but yet retain the requisite cytotoxic T cell inducibility. Further provided are nucleic acids encoding any of these aforementioned peptides as well as pharmaceutical agents, substances and compositions including any of the aforementioned peptides or nucleic acids. The peptides, nucleic acids, pharmaceutical agents, substances and compositions of this invention find particular utility in the treatment of cancers and tumors.

8 Claims, 9 Drawing Sheets

(56) References Cited

OTHER PUBLICATIONS

Rosenberg, et al., "Cancer immunotherapy: moving beyond current vaccines," *Nat Med.*, vol. 10(9), pp. 909-915 (Sep. 2004).

Tanaka, et al., "Induction of Antitumor Cytotoxic T Lymphocytes with a MAGE-3-encoded Synthetic Peptide Presented by Human Leukocytes Antigen-A24," *Cancer Res.*, vol. 57(20), pp. 4465-4468 (Oct. 15, 1997).

Van Der Burg, et al., "Immunogenicity of Peptides Bound to MHC Class I Molecules Depends on the MHC-Peptide Complex Stability," *J Immunol.*, vol. 156(9), pp. 3308-3314 (May 1, 1996).

Vissers, et al., "The Renal Cell Carcinoma-associated Antigen G250 Encodes a Human Leukocyte Antigen (HLA)-A2.1-restricted Epitope Recognized by Cytotoxic T Lymphocytes," *Cancer Res.*, vol. 59(21), pp. 5554-5559 (Nov. 1, 1999).

U.S. Appl. No. 11/913,147, which is a U.S. National Stage of PCT/JP2006/314946, 136 pages, filed on Jul. 21, 2006.

International Search Report for PCT/JP2010/007228, 3 pages, mailed Mar. 15, 2011.

Adams, et al., "Prediction of binding to MHC class I molecules," *J Immunol Methods*, vol. 185(2), pp. 181-190 (Sep. 25, 1995).

Dionne, et al., "Functional characterization of CTL against gp100 altered peptide ligands," *Cancer Immunol Immunother.*, vol. 52(4), pp. 199-206 (Apr. 2003, Epub Feb. 18, 2003).

Dionne, et al., "Her-2/neu altered peptide ligand-induced CTL responses: implications for peptides with increased HLA affinity and T-cell-receptor interaction," *Cancer Immunol Immunother.*, vol. 53(4), pp. 307-314 (Apr. 2004, Epub Nov. 5, 2003).

Falk, et al., "Allele-specific motifs revealed by sequencing of self-peptides eluted from MHC molecules," *Nature*, vol. 351(6324), pp. 290-296 (May 23, 1991).

Hoffmann, et al., "The Ability of Variant Peptides to Reverse the Nonresponsiveness of T Lymphocytes to the Wild-Type Sequence $p53_{264-272}$ Epitope," *J Immunol.*, vol. 168(3), pp. 1338-1347 (Feb. 1, 2002).

Kondo, et al., "Prominent Roles of Secondary Anchor Residues in Peptide Binding to HLA-A24 Human Class I Molecules," *J Immunol.*, vol. 155(9), pp. 4307-4312 (Nov. 1, 1995).

Kubo, et al., "Definition of Specific Peptide Motifs for Four Major HLA-A Alleles," *J Immunol.*, vol. 152(8), pp. 3913-3924 (Apr. 15, 1994).

Parker, et al., "Scheme for Ranking Potential HLA-A2 Binding Peptides Based on Independent Binding of Individual Peptide Side-Chains," *J Immunol.*, vol. 152(1), pp. 163-175 (Jan. 1, 1994).

Rammensee, et al., "MHC ligands and peptide motifs: first listing," *Immunogenetics*, vol. 41(4), pp. 178-228 (1995).

Schueler-Furman, et al., "Structure-based prediction of binding peptides to MHC class I molecules: Application to a broad range of MHC alleles," *Protein Sci.*, vol. 9(9), pp. 1838-1846 (Sep. 2000).

Zaremba, et al., "Identification of an Enhancer Agonist Cytotoxic T Lymphocytes Peptide from Human Carcinoembryonic Antigen," *Cancer Res.*, vol. 57(20), pp. 4570-4577 (Oct. 15, 1997).

Fig. 3
a TMEM22-A24-9-331 #8-150
b TMEM22-A24-9-204 #4-181
c TMEM22-A24-9-297 #8-176
d TMEM22-A24-10-204 #3-173
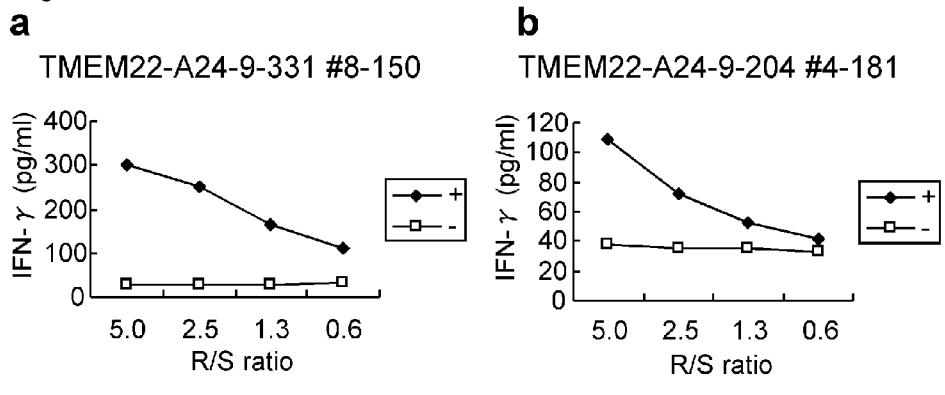
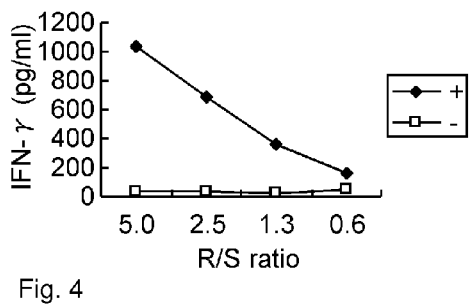
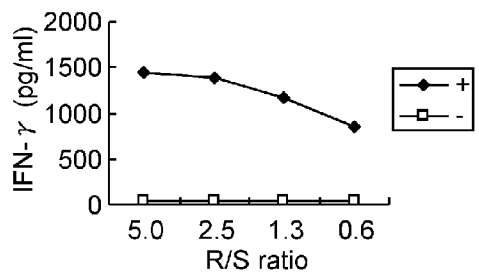
Fig. 4
TMEM22-A24-9-385 COS7
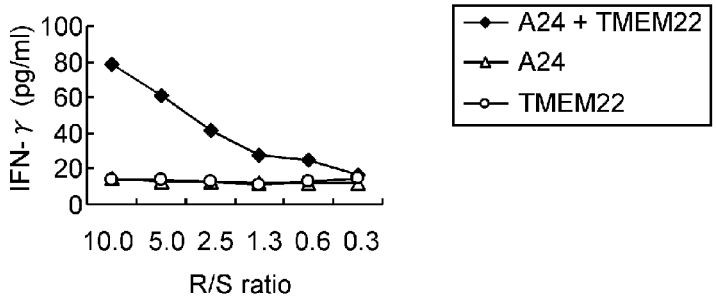

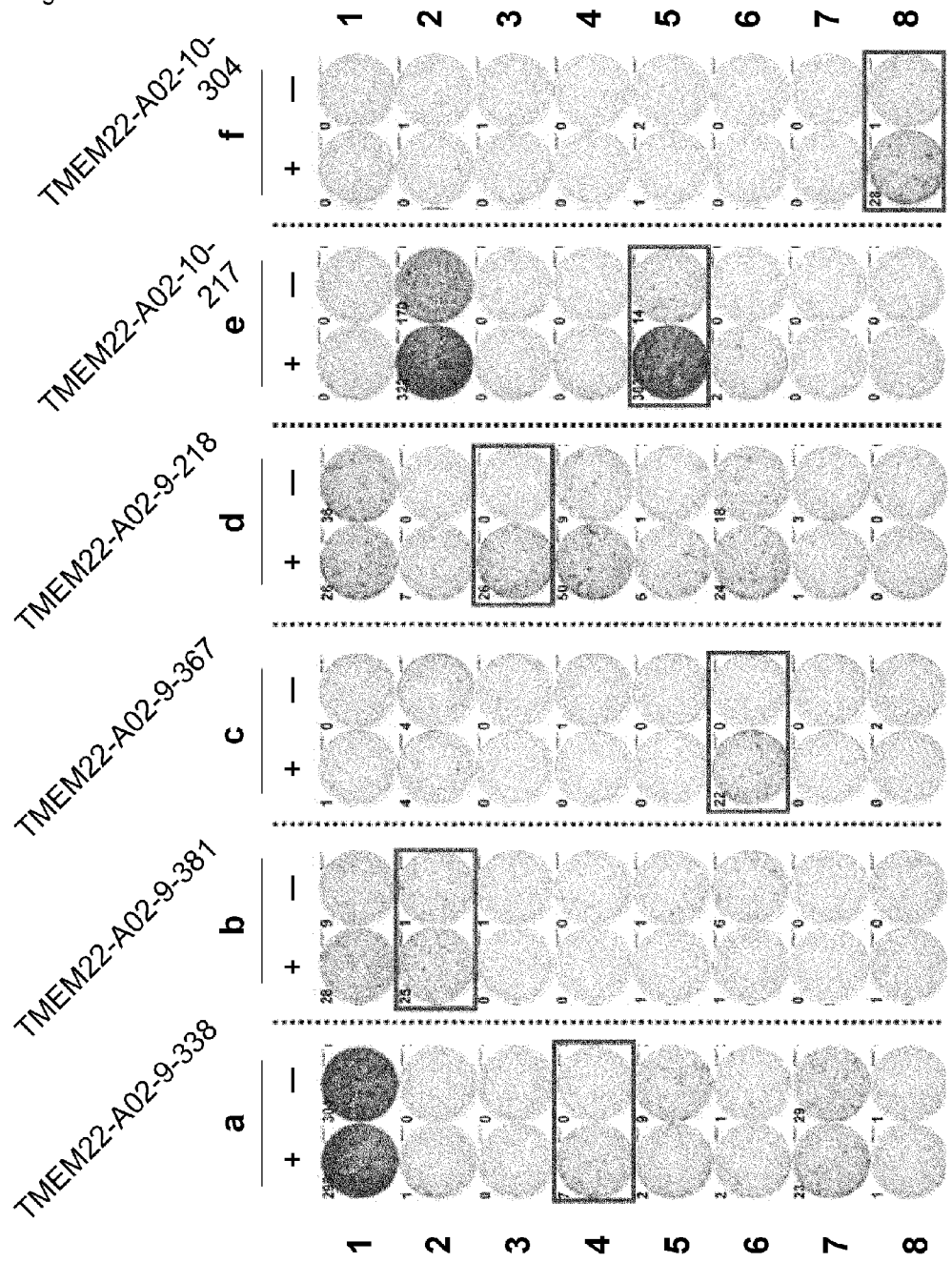
Fig. 5a-f

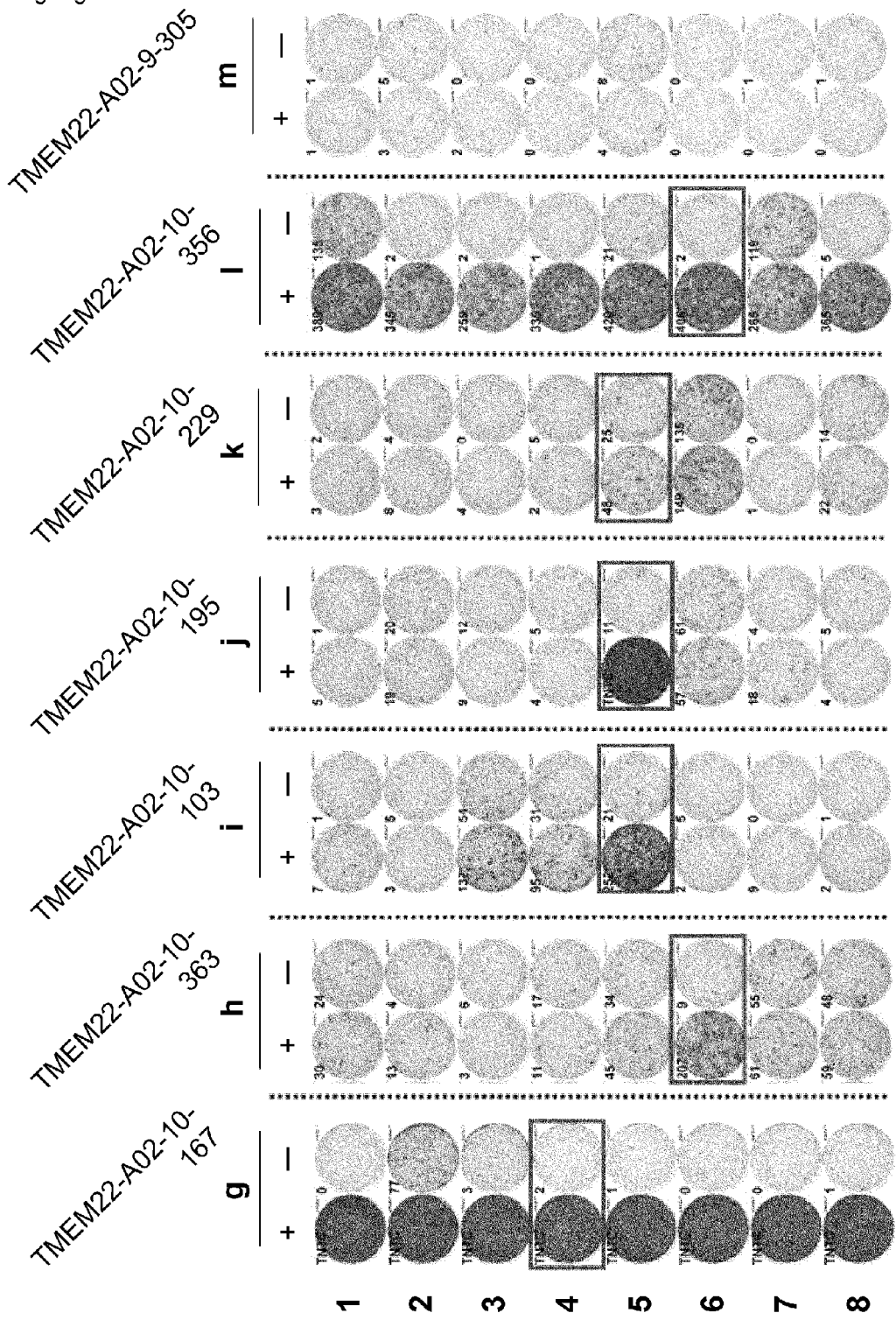
Fig. 5g-m

Fig. 6a-f
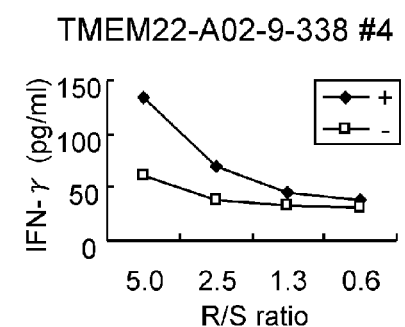
a TMEM22-A02-9-338 #4
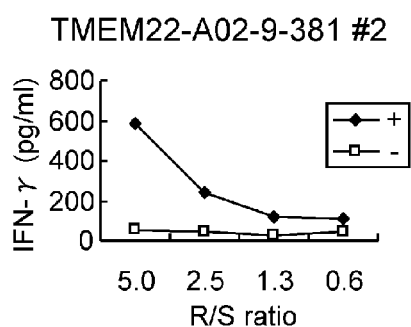
b TMEM22-A02-9-381 #2
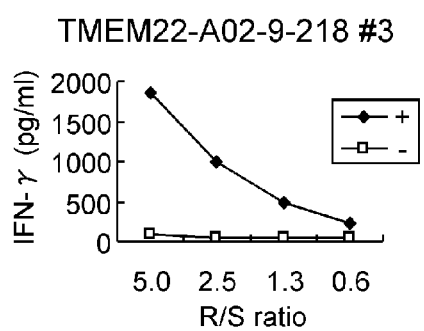
c TMEM22-A02-9-218 #3
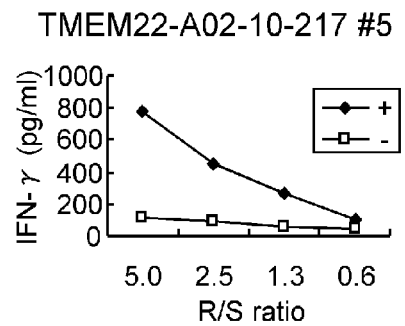
d TMEM22-A02-10-217 #5
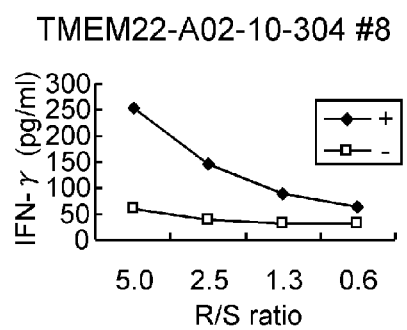
e TMEM22-A02-10-304 #8
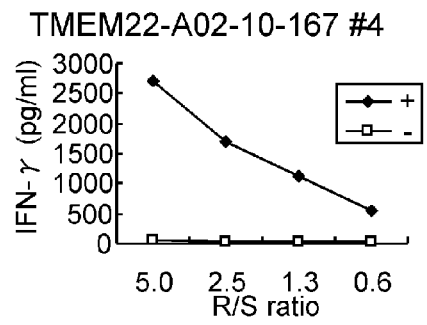
f TMEM22-A02-10-167 #4

Fig. 6g-j
g
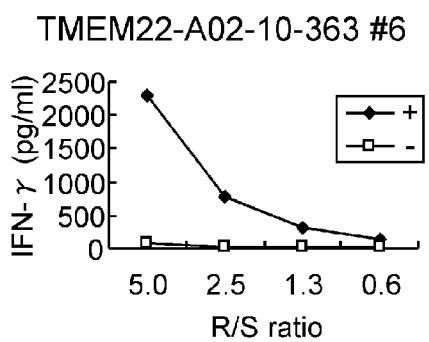
h
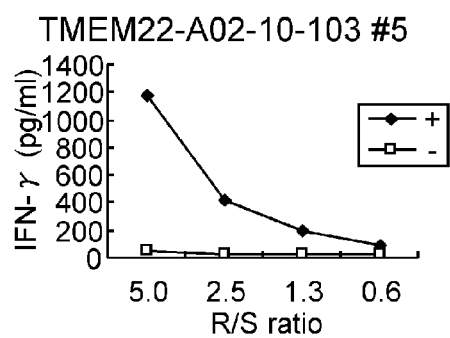
i
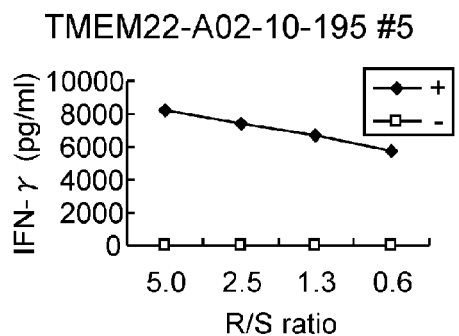
j
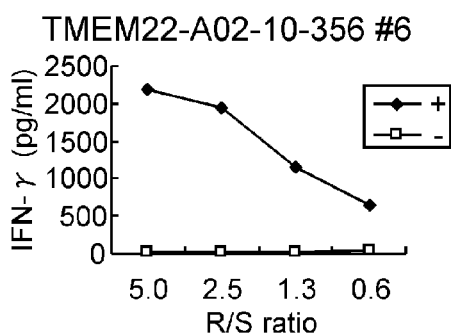

Fig. 7a-f
a
TMEM22-A02-9-381 #2-114
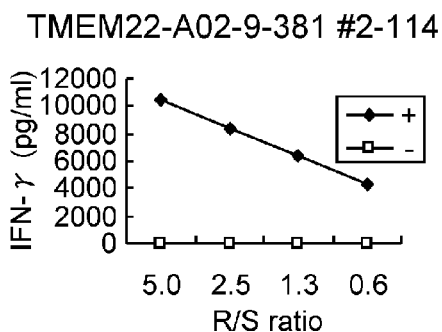
b
TMEM22-A02-9-218 #3-37
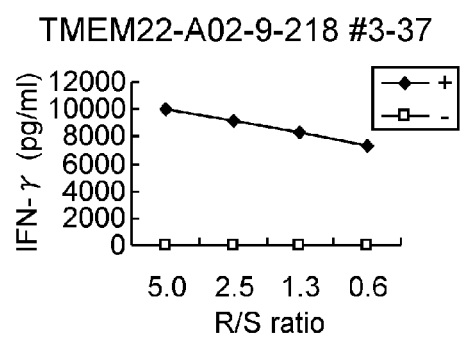
c
TMEM22-A02-10-217 #5-127
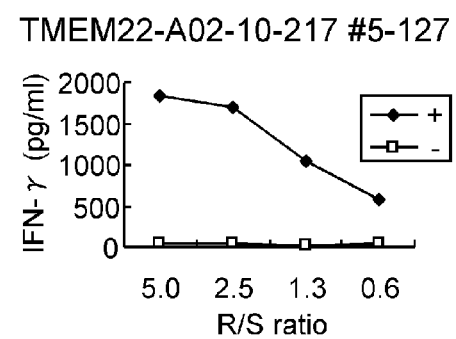
d
TMEM22-A02-10-304 #8-126
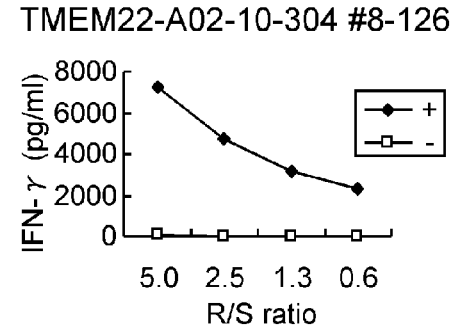
e
TMEM22-A02-10-167 #4-105
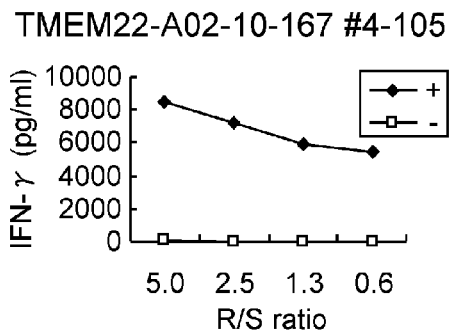
f
TMEM22-A02-10-363 #6-186
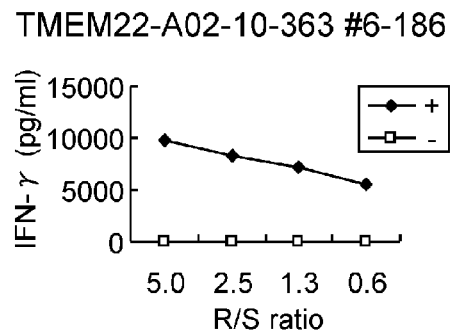

Fig. 7g-i
g
TMEM22-A02-10-103 #5-155
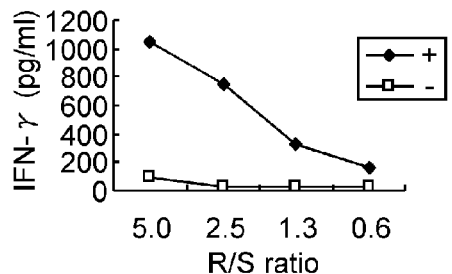
h
TMEM22-A02-10-195 #5-92
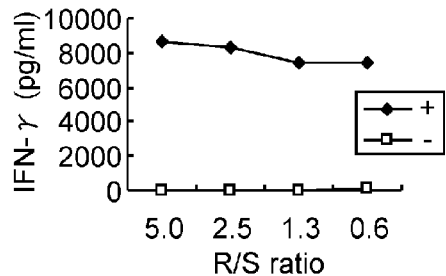
i
TMEM22-A02-10-356 #6-173
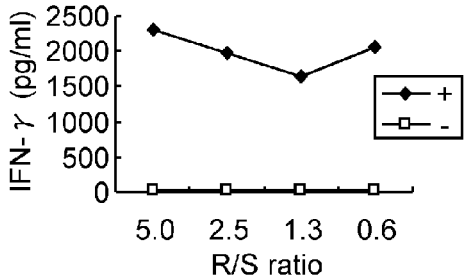
Fig. 8
TMEM22-A02-10-195
COS7
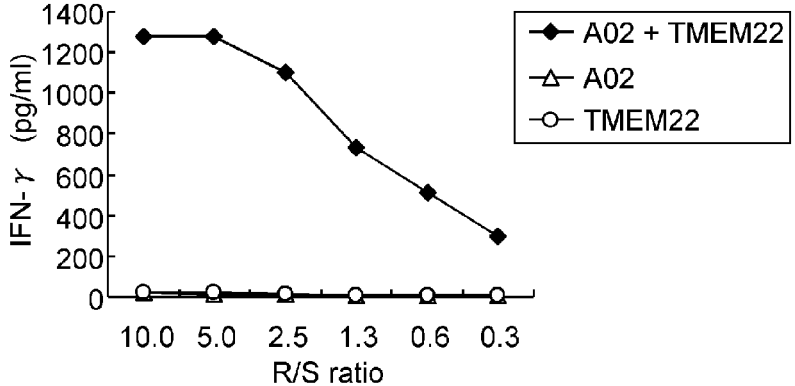

TMEM22 PEPTIDES AND VACCINES INCLUDING THE SAME

PRIORITY

This application is a U.S. National Phase of PCT/JP2010/007228, filed Dec. 13, 2010, which claims the benefit of U.S. Provisional Application No. 61/286,213, filed on Dec. 14, 2009, U.S. Provisional Application No. 61/287,650, filed on Dec. 17, 2009, and U.S. Provisional Application No. 61/326,380, filed on Apr. 21, 2010, the contents of each of the aforementioned applications are hereby incorporated herein by reference in their entirety for all purposes.

TECHNICAL FIELD

The present invention relates to the field of biological science, more specifically to the field of cancer therapy. In particular, the present invention relates to novel peptides that are extremely effective as cancer vaccines as well as drugs for treating and preventing tumors.

REFERENCE TO A SEQUENCE LISTING

This application includes a Sequence Listing as a text file named "87331-021710US-842286_SEQLIST.txt" created Aug. 20, 2012, and containing 27,710 bytes. The material contained in this text file is incorporated by reference in its entirety for all purposes.

BACKGROUND ART

It has been demonstrated that CD8 positive CTLs recognize epitope peptides derived from tumor-associated antigens (TAAs) found on the major histocompatibility complex (MHC) class I molecule, and then kill the tumor cells. Since the discovery of melanoma antigen (MAGE) family as the first example of TAAs, many other TAAs have been discovered through immunological approaches (NPLs 1, 2). Some of these TAAs are currently undergoing clinical development as immunotherapeutic targets.

Favorable TAAs are indispensable for proliferation and survival of cancer cells. The use of such TAAs as targets for immunotherapy may minimize the well-described risk of immune escape of cancer cells attributable to deletion, mutation, or down-regulation of TAAs as a consequence of therapeutically driven immune selection. Accordingly, the identification of new TAAs capable of inducing potent and specific anti-tumor immune responses warrants further development and clinical investigation of peptide vaccination strategies for various types of cancer is ongoing (NPLs 3 to 10). To date, several clinical trials using these TAA derived peptides have been reported. Unfortunately, many of the current cancer vaccine trials have shown only a low objective response rate (NPLs 11 to 13). Therefore, identification of novel TAAs useful as immunotherapeutic targets is still required.

To that end, through gene expression profiling with a genome-wide cDNA microarray containing 23,648 genes, TMEM22 (GenBank Accession No. NM_025246, NM_001097599, NM_001097600), transmembrane protein 22, has been identified as a transmembrane protein associated with cell growth of renal cell carcinoma (RCC) (NPL 14). Northern blot analysis has confirmed the expression TMEM22 to be specifically up-regulated in a great majority of RCC clinical samples and cell lines examined, with only barely detectable expression in normal human tissues examined. Furthermore, down-regulation of TMEM22 expression by specific siRNA has been shown to result in significant reduction of RCC cell growth (NPL 15). However, the pathophysiological role and biological function of TMEM-22 in the context of cancer cells have not yet been reported.

CITATION LIST

Non Patent Literature

[NPL 1] Boon T, Int J Cancer 1993, 54(2): 177-80
[NPL 2] Boon T & van der Bruggen P, J Exp Med 1996, 183(3): 725-9
[NPL 3] Harris C C, J Natl Cancer Inst 1996, 88(20): 1442-55
[NPL 4] Butterfield L H et al., Cancer Res 1999, 59(13): 3134-42
[NPL 5] Vissers J L et al., Cancer Res 1999, 59(21): 5554-9
[NPL 6] van der Burg S H et al., J Immunol 1996, 156(9): 3308-14
[NPL 7] Tanaka F et al., Cancer Res 1997, 57(20): 4465-8
[NPL 8] Fujie T et al., Int J Cancer 1999, 80(2): 169-72
[NPL 9] Kikuchi M et al., Int J Cancer 1999, 81(3): 459-66
[NPL 10] Oiso M et al., Int J Cancer 1999, 81(3): 387-94
[NPL 11] Belli F et al., J Clin Oncol 2002, 20(20): 4169-80
[NPL 12] Coulie P G et al., Immunol Rev 2002, 188: 33-42
[NPL 13] Rosenberg S A et al., Nat Med 2004, 10(9): 909-15
[NPL 14] Hirota E et al., Int J. Oncol. 2006; 29(4):799-827
[NPL 15] Dobashi S et al., Oncol Rep. 2009; 21(2):305-12

SUMMARY OF INVENTION

The present invention is based, in part, on the discovery of novel peptides that may serve as suitable targets of immunotherapy. Because TAAs are generally perceived for the immune system as "self" and therefore often have no immunogenicity, the discovery of appropriate targets is of extreme importance. Recognizing that TMEM22 (as described, for example, in SEQ ID NOs: 91 and 92, also indicated in GenBank Accession No. NM_025246, NM_001097599, NM_001097600) has been identified as up-regulated in tissues of cancers including but not limited to acute myelogenous leukemia (AML), bladder cancer, cholangiocellular carcinoma (CCC), esophagus cancer, lymphoma, prostate cancer, renal cell carcinoma (RCC) and small cell lung cancer (SCLC), the present invention focuses on TMEM22 as a candidate target of immunotherapy.

To that end, the present invention is directed, at least in part, to the identification of specific epitope peptides of TMEM22 that possess the ability to induce cytotoxic T lymphocytes (CTLs) specific to TMEM22. As discussed in detail below, peripheral blood mononuclear cells (PBMCs) obtained from a healthy donor were stimulated using HLA-A*2402 or HLA-A*0201 binding candidate peptides derived from TMEM22. CTL lines with specific cytotoxicity against HLA-A24 or HLA-A2 positive target cells pulsed with each of candidate peptides were then established. Taken together, these results demonstrate that these peptides are HLA-A24 or HLA-A2 restricted epitope peptides that can induce potent and specific immune responses against cells expressing TMEM22. The results further demonstrate that TMEM22 is strongly immunogenic and that the epitopes thereof are effective targets for tumor immunotherapy.

Accordingly, it is an object of the present invention to provide isolated TMEM22 (SEQ ID NO: 92) peptides or fragments thereof that bind to HLA antigen and have CTL inducibility. Such peptides can be used to induce CTL ex vivo or can be administered to a subject for inducing immune responses against cancers, examples of which include, but are not limited to, AML, bladder cancer, CCC, esophagus cancer, lymphoma, prostate cancer, RCC and SCLC. Preferred peptides are nonapeptides or decapeptides, more preferably peptides that show strong CTL inducibility and have an amino acid sequence selected from among SEQ ID NOs: 1, 2, 3, 4, 5, 6, 10, 12, 16, 18, 19, 22, 28, 31, 35, 38, 41, 48, 61, 62, 65, 67, 70, 74, 77 and 83.

The present invention also contemplates modified peptides, having an amino acid sequence of SEQ ID NOs: 1, 2, 3, 4, 5, 6, 10, 12, 16, 18, 19, 22, 28, 31, 35, 38, 41, 48, 61, 62, 65, 67, 70, 74, 77 and 83 wherein one, two or more amino acid(s) is/are substituted, deleted or added, so long as the modified peptides retain the requisite CTL inducibility of the original peptide.

Further, the present invention provides isolated polynucleotides encoding any of the peptides of the present invention. These polynucleotides can be used to induce antigen-expressing cells (APCs) with CTL inducibility or, like the peptides of the present invention, can be administered to a subject for inducing immune responses against cancers.

When administered to a subject, the present peptides are presented on the surface of APCs so as to induce CTLs targeting the respective peptides. Therefore, it is an object of the present invention to provide agents that induce CTLs, such agents including one or more peptides of the present invention or polynucleotides encoding such peptides. The present invention further contemplates pharmaceutical agents including one or more peptides of the present invention or polynucleotides encoding such peptides, such agents useful for the treatment and/or for the prophylaxis of cancers, examples of which include, but are not limited to, AML, bladder cancer, CCC, esophagus cancer, lymphoma, prostate cancer, RCC and SCLC, and/or for preventing postoperative recurrence thereof, but not limited. Thus, it is yet another object of the present invention to provide pharmaceutical agents formulated for the treatment and/or prevention of cancer, and/or prevention of postoperative recurrence thereof and including any of the peptides or polynucleotides of the present invention. Instead of or in addition to the present peptides or polynucleotides, the pharmaceutical agents of the present invention may optionally include, as the active ingredient, APCs or exosomes that present any of the peptides of the present invention.

The peptides and polynucleotides of the present invention may be used to induce APCs that present on the surface a complex of an HLA antigen and a present peptide, for example, by contacting APCs derived from a subject with the present peptide or introducing a polynucleotide encoding the present peptide into APCs. Such APCs have high CTL inducibility against the target peptides and thus are useful for cancer immunotherapy. Accordingly, it is another object of the present invention to provide methods for inducing APCs with CTL inducibility as well as APCs obtained by such methods.

It is a further object of the present invention to provide a method for inducing CTL that includes the step of co-culturing CD8-positive cells with APCs or exosomes presenting a peptide of the present invention on its surface or the step of introducing a gene that includes a polynucleotide encoding a T cell receptor (TCR) subunit binding to the present peptide. CTLs obtained by the present methods also find utility in the treatment and/or prevention of cancers, examples of which include, but are not limited to, AML, bladder cancer, CCC, esophagus cancer, lymphoma, prostate cancer, RCC and SCLC. Therefore, it is another object of the present invention to provide CTLs obtained by the present methods.

Moreover, a further object of the present invention is to provide methods for inducing an immune response against cancer, in a subject in need thereof, such methods including the step of administering to the subject agents or compositions that contain TMEM22 or fragments thereof, polynucleotides encoding TMEM22 or the fragments thereof, and exosomes or APCs presenting TMEM22 or the fragments thereof.

The applicability of the present invention may extends to any of a number of diseases relating to or arising from TMEM22 overexpression including cancer, examples of which include, but are not limited to, AML, bladder cancer, CCC, esophagus cancer, lymphoma, prostate cancer, RCC and SCLC.

In addition to the above, other objects and features of the invention will become more fully apparent when the following detailed description is read in conjunction with the accompanying figures and examples. However, it is to be understood that both the foregoing summary of the invention and the following detailed description are of exemplified embodiments, and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

BRIEF DESCRIPTION OF DRAWINGS

Various aspects and applications of the present invention will become apparent to the skilled artisan upon consideration of the brief description of the figures. and the detailed description of the present invention and its preferred embodiments which follows.

FIG. 3 depicts line graphs showing the IFN-gamma production of the CTL clones established by limiting dilution from the CTL lines stimulated with TMEM22-A24-9-331 (SEQ ID NO: 4) (a), TMEM22-A24-9-204 (SEQ ID NO: 6) (b), TMEM22-A24-9-297 (SEQ ID NO: 10) (c) and TMEM22-A24-10-204 (SEQ ID NO: 22) (d). The results demonstrate that the CTL clones established by stimulation with each peptide showed potent IFN-gamma production as compared with the control. In the figure, "+" indicates the IFN-gamma production against target cells pulsed with the each peptide and "−" indicates the IFN-gamma production against target cells not pulsed with any peptides.

FIG. 4 depicts line graphs showing specific CTL activity against the target cells that exogenously express TMEM22 and HLA-A*2402. COS7 cells transfected with HLA-A*2402 or with the full length of TMEM22 gene were prepared as controls. The CTL line established with TMEM22-A24-9-385 (SEQ ID NO: 5) showed specific CTL activity against COS7 cells transfected with both TMEM22 and HLA-A*2402 (lozenge). On the other hand, no significant specific CTL activity was detected against target cells expressing either HLA-A*2402 (triangle) or TMEM22 (circle).

FIG. 5a-f depicts photographs showing the results of IFN-gamma ELISPOT assay on CTLs that were induced with peptides derived from TMEM22. The CTLs in the well number #4 with TMEM22-A02-9-338 (SEQ ID NO: 35) (a), #2 with TMEM22-A02-9-381 (SEQ ID NO: 38) (b), #6 with TMEM22-A02-9-367 (SEQ ID NO: 41) (c), #3 with TMEM22-A02-9-218 (SEQ ID NO: 48) (d), #5 with TMEM22-A02-10-217 (SEQ ID NO: 61) (e), and #8 with TMEM22-A02-10-304 (SEQ ID NO: 62) (f) showed potent IFN-gamma production as compared with the control, respectively. The square on the well of these pictures indicates that the cells from corresponding well were expanded to establish CTL lines. In contrast, as typical case of negative data, specific IFN-gamma production was not shown from the CTL stimulated with TMEM22-A02-9-305 (SEQ ID NO: 33) (m). In the figures, "+" indicates the IFN-gamma production against target cells pulsed with the appropriate peptide, and "−" indicates the IFN-gamma production against target cells not pulsed with any peptides.

FIG. 5g-m depicts photographs showing the results of IFN-gamma ELISPOT assay on CTLs that were induced with peptides derived from TMEM22. The CTLs in the well number #4 with TMEM22-A02-10-167 (SEQ ID NO: 65) (g), #6 with TMEM22-A02-10-363 (SEQ ID NO: 67) (h), #5 with TMEM22-A02-10-103 (SEQ ID NO: 70) (i), #5 with TMEM22-A02-10-195 (SEQ ID NO: 74) (j), #5 with TMEM22-A02-10-229 (SEQ ID NO: 77) (k) and #6 with TMEM22-A02-10-356 (SEQ ID NO: 83) (l) showed potent IFN-gamma production as compared with the control, respectively. The square on the well of these pictures indicates that the cells from cor-responding well were expanded to establish CTL lines. In contrast, as typical case of negative data, specific IFN-gamma production was not shown from the CTL stimulated with TMEM22-A02-9-305 (SEQ ID NO: 33) (m). In the figures, "+" indicates the IFN-gamma production against target cells pulsed with the appropriate peptide, and "−" indicates the IFN-gamma production against target cells not pulsed with any peptides.

FIG. 6a-f depicts line graphs showing the IFN-gamma production of the CTL lines stimulated with TMEM22-A02-9-338 (SEQ ID NO: 35) (a), TMEM22-A02-9-381 (SEQ ID NO: 38) (b), TMEM22-A02-9-218 (SEQ ID NO: 48) (c), TMEM22-A02-10-217 (SEQ ID NO: 61) (d), TMEM22-A02-10-304 (SEQ ID NO: 62) (e), and TMEM22-A02-10-167 (SEQ ID NO: 65) (f) detected by IFN-gamma ELISA assay. The results demonstrate that CTL lines established by stimulation with each peptide showed potent IFN-gamma production as compared with the control. In the figures, "+" indicates the IFN-gamma production against target cells pulsed with the appropriate peptide, and "−" indicates the IFN-gamma production against target cells not pulsed with any peptides.

FIG. 6g-j depicts line graphs showing the IFN-gamma production of the CTL lines stimulated with TMEM22-A02-10-363 (SEQ ID NO: 67) (g), TMEM22-A02-10-103 (SEQ ID NO: 70) (h), TMEM22-A02-10-195 (SEQ ID NO: 74) (i) and TMEM22-A02-10-356 (SEQ ID NO: 83) (j) detected by IFN-gamma ELISA assay. The results demonstrate that CTL lines established by stimulation with each peptide showed potent IFN-gamma production as compared with the control. In the figures, "+" indicates the IFN-gamma production against target cells pulsed with the appropriate peptide, and "−" indicates the IFN-gamma production against target cells not pulsed with any peptides.

FIG. 7a-f depicts line graphs showing the IFN-gamma production of the CTL clones established by limiting dilution from the CTL lines stimulated with TMEM22-A02-9-381 (SEQ ID NO: 38) (a), TMEM22-A02-9-218 (SEQ ID NO: 48) (b), TMEM22-A02-10-217 (SEQ ID NO: 61) (c), TMEM22-A02-10-304 (SEQ ID NO: 62) (d), TMEM22-A02-10-167 (SEQ ID NO: 65) (e), and TMEM22-A02-10-363 (SEQ ID NO: 67) (f). The results demonstrate that the CTL clones established by stimulation with each peptide showed potent IFN-gamma production as compared with the control. In the figure, "+" indicates the IFN-gamma production against target cells pulsed with the appropriate peptide and "−" indicates the IFN-gamma production against target cells not pulsed with any peptides.

FIG. 7g-i depicts line graphs showing the IFN-gamma production of the CTL clones established by limiting dilution from the CTL lines stimulated with TMEM22-A02-10-103 (SEQ ID NO: 70) (g), TMEM22-A02-10-195 (SEQ ID NO: 74) (h) and TMEM22-A02-10-356 (SEQ ID NO: 83) (i). The results demonstrate that the CTL clones established by stimulation with each peptide showed potent IFN-gamma production as compared with the control. In the figure, "+" indicates the IFN-gamma production against target cells pulsed with the appropriate peptide and "−" indicates the IFN-gamma production against target cells not pulsed with any peptides.

FIG. 8 depicts line graphs showing specific CTL activity against the target cells that exogenously express TMEM22 and HLA-A*0201. COS7 cells transfected with HLA-A*0201 or the full length TMEM22 gene were prepared as the controls. The CTL clone established with TMEM22-A02-10-195 (SEQ ID NO: 74) showed specific CTL activity against COS7 cells transfected with both TMEM22 and HLA-A*0201 (black lozenge). On the other hand, no significant specific CTL activity was detected against target cells expressing either HLA-A*0201 (triangle) or TMEM22 (circle).

DESCRIPTION OF EMBODIMENTS

Figure 1:
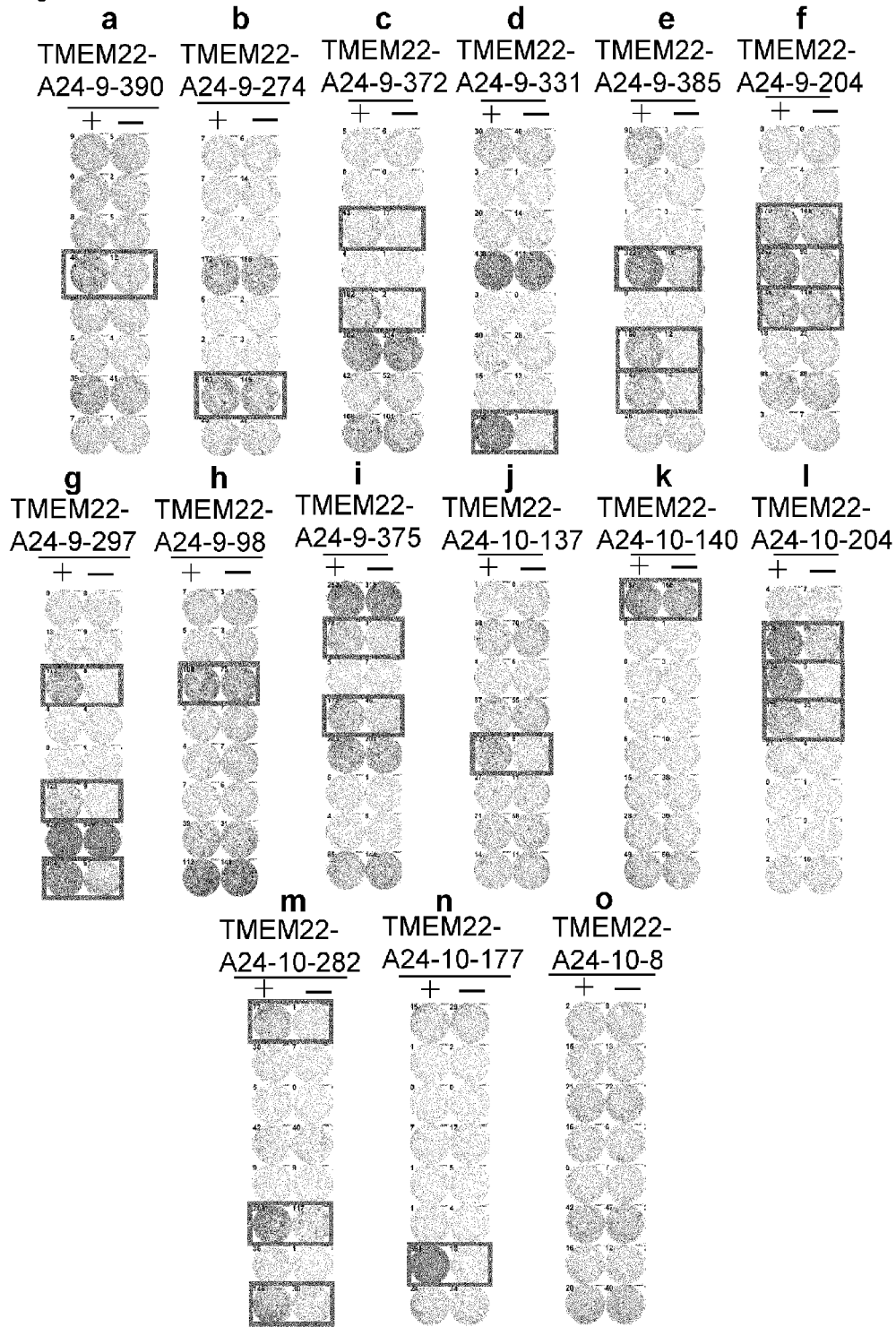
FIG. 1 depicts photographs showing the results of IFN-gamma ELISPOT assays on CTLs that were induced with peptides derived from TMEM22. The CTLs in well number #4 were stimulated with TMEM22-A24-9-390 (SEQ ID NO: 1) (a), #7 with TMEM22-A24-9-274 (SEQ ID NO: 2) (b), #3 and #5 with TMEM22-A24-9-372 (SEQ ID NO: 3) (c), #8 with TMEM22-A24-9-331 (SEQ ID NO: 4) (d), #4, #6 and #7 with TMEM22-A24-9-385 (SEQ ID NO: 5) (e), #3, #4 and #5 with TMEM22-A24-9-204 (SEQ ID NO: 6) (f), #3, #6 and #8 with TMEM22-A24-9-297 (SEQ ID NO: 10) (g), #3 with TMEM22-A24-9-98 (SEQ ID NO: 12) (h), #2 and #4 with TMEM22-A24-9-375 (SEQ ID NO: 16) (i), #5 with TMEM22-A24-10-137 (SEQ ID NO: 18) (j), #1 with TMEM22-A24-10-140 (SEQ ID NO: 19) (k), #2, #3 and #4 with TMEM22-A24-10-204 (SEQ ID NO: 22) (l), #1, #6, #8 with TMEM22-A24-10-282 (SEQ ID NO: 28) (m) and #7 with TMEM22-A24-10-177 (SEQ ID NO: 31) (n) showed potent IFN-gamma production as compared with the control, respectively. The square on the well of these pictures indicates that the cells from corresponding well were expanded to establish CTL lines. In contrast, as typical case of negative data, specific IFN-gamma production was not shown from the CTL stimulated with TMEM22-A24-10-8 (SEQ ID NO: 17) against peptide-pulsed target cells (o). The square on the well of these pictures indicated that the cells from corresponding well were expanded to establish CTL lines. In the figures, "+" indicates the IFN-gamma production against target cells pulsed with the appropriate peptide, and "−" indicates the IFN-gamma production against target cells not pulsed with any peptides.

Although any methods and materials similar or equivalent to those described herein can be used in the practice or testing of embodiments of the present invention, the preferred methods, devices, and materials are now described. However, before the present materials and methods are described, it is to be understood that the present invention is not limited to the particular sizes, shapes, dimensions, materials, methodologies, protocols, etc. described herein, as these may vary in accordance with routine experimentation and optimization. It is also to be understood that the terminology used in the description is for the purpose of describing the particular versions or embodiments only, and is not intended to limit the scope of the present invention which will be limited only by the appended claims.

The disclosure of each publication, patent or patent application mentioned in this specification is specifically incorporated by reference herein in its entirety. However, nothing herein is to be construed as an admission that the invention is not entitled to antedate such disclosure by virtue or prior invention.

Unless otherwise defined, all technical and scientific terms used herein have the same meaning as commonly understood by one of ordinary skill in the art to which the present invention belongs. In case of conflict, the present specification, including definitions, will control. In addition, the materials, methods, and examples are illustrative only and not intended to be limiting.

I. Definitions

The words "a", "an", and "the" as used herein mean "at least one" unless otherwise specifically indicated.

The terms "polypeptide", "peptide" and "protein" are used interchangeably herein to refer to a polymer of amino acid residues. The terms apply to amino acid polymers in which one or more amino acid residue is a modified residue, or a non-naturally occurring residue, such as an artificial chemical mimetic of a corresponding naturally occurring amino acid, as well as to naturally occurring amino acid polymers.

The term "oligopeptide" sometimes used in the present specification is used to refer to peptides of the present invention which are 20 residues or fewer, typically 15 residues or fewer in length and is typically composed of between about 8 and about 11 residues, often 9 or 10 residues.

The term "amino acid" as used herein refers to naturally occurring and synthetic amino acids, as well as amino acid analogs and amino acid mimetics that similarly function to the naturally occurring amino acids. Naturally occurring amino acids are those encoded by the genetic code, as well as those modified after translation in cells (e.g., hydroxyproline, gamma-carboxyglutamate, and O-phosphoserine). The phrase "amino acid analog" refers to compounds that have the same basic chemical structure (an alpha carbon bound to a hydrogen, a carboxy group, an amino group, and an R group) as a naturally occurring amino acid but have a modified R group or modified backbones (e.g., homoserine, norleucine, methionine, sulfoxide, methionine methyl sulfonium). The phrase "amino acid mimetic" refers to chemical compounds that have different structures but similar functions to general amino acids.

Amino acids may be referred to herein by their commonly known three letter symbols or the one-letter symbols recommended by the IUPAC-IUB Biochemical Nomenclature Commission.

The terms "gene", "polynucleotides", "nucleotides" and "nucleic acids" are used interchangeably herein and, unless otherwise specifically indicated are similarly to the amino acids referred to by their commonly accepted single-letter codes.

The terms "composition", "substance" and "agent" are used interchangeably herein to refer to a product that includes the specified ingredients in the specified amounts, as well as any product that results, directly or indirectly, from combination of the specified ingredients in the specified amounts. Such term in relation to "pharmaceutical composition", is intended to encompass a product including the active ingredient(s), and any inert ingredient(s) that make up the carrier, as well as any product that results, directly or indirectly, from combination, complexation or aggregation of any two or more of the ingredients, or from dissociation of one or more of the ingredients, or from other types of reactions or interactions of one or more of the ingredients. Accordingly, in the context of the present invention, the term "pharmaceutical composition" refers to any composition made by admixing a compound of the present invention and a pharmaceutically or physiologically acceptable carrier. The phrase "pharmaceutically acceptable carrier" or "physiologically acceptable carrier", as used herein, means a pharmaceutically or physiologically acceptable material, composition, substance or vehicle, including but not limited to, a liquid or solid filler, diluent, excipient, solvent or encapsulating material, involved in carrying or transporting the subject scaffolded polypharmacophores from one organ, or portion of the body, to another organ, or portion of the body.

The term "active ingredient" herein refers to a substance in an agent or composition that is biologically or physiologically active. Particularly, in a pharmaceutical agent or composition, "active ingredient" refers to a substance that shows an objective pharmacological effect. For example, in case of pharmaceutical agents or compositions for use in the treatment or prevention of cancer, active ingredients in the agents or compositions may lead to at least one biological or physiologically action on cancer cells and/or tissues directly or indirectly. Preferably, such action may include reducing or inhibiting cancer cell growth, damaging or killing cancer cells and/or tissues, and so on. Typically, indirect effect of active ingredients is inductions of CTLs recognizing or killing cancer cells. Before formulated, "active ingredient" is also referred to as "bulk", "drug substance" or "technical product".

The pharmaceutical agents or compositions of the present invention find particular use as vaccines. In the context of the present invention, the phrase "vaccine" (also referred to as an "immunogenic composition") refers to a substance that has the function to induce anti-tumor immunity upon inoculation into animals.

Unless otherwise defined, the term "cancer" refers to the cancers overexpressing TMEM22 gene, examples of which include, but are not limited to acute myelogenous leukemia (AML), bladder cancer, cholangiocellular carcinoma (CCC), esophagus cancer, lymphoma, prostate cancer, renal cell carcinoma (RCC) and small cell lung cancer (SCLC).

Unless otherwise defined, the terms "cytotoxic T lymphocyte", "cytotoxic T cell" and "CTL" are used interchangeably herein and unless otherwise specifically indicated, refer to a sub-group of T lymphocytes that are capable of recognizing non-self cells (e.g., tumor cells, virus-infected cells) and inducing the death of such cells.

Unless otherwise defined, the term "HLA-A24", as used herein, representatively refers to the subtypes such as HLA-A*2402.

Unless otherwise defined, the term "HLA-A2", as used herein, representatively refers to the subtypes such as HLA-A*0201 and HLA-A*0206.

Unless otherwise defined, the term "kit" as used herein, is used in reference to a combination of reagents and other materials. It is contemplated herein that the kit may include microarray, chip, marker, and so on. It is not intended that the term "kit" be limited to a particular combination of reagents and/or materials.

As used herein, in the context of a subject or patient, the phrase "HLA-A2 positive" refers to that the subject or patient homozygously or heterozygously possess HLA-A2 antigen gene, and HLA-A2 antigen is expressed in cells of the subject or patient as an HLA antigen.

Similarly, as used herein, in the context of a subject or patient, the phrase "HLA-A24 positive" also refers to that the subject or patient homozygously or heterozygously possess HLA-A24 antigen gene, and HLA-A24 antigen is expressed in cells of the subject or patient as an HLA antigen.

To the extent that the methods and compositions of the present invention find utility in the context of the "treatment" of cancer, a treatment is deemed "efficacious" if it leads to clinical benefit such as, reduction in expression of TMEM22 gene, or a decrease in size, prevalence, or metastatic potential of the cancer in the subject. When the treatment is applied prophylactically, "efficacious" means that it retards or prevents cancers from forming or prevents or alleviates a clinical symptom of cancer. Efficaciousness is determined in association with any known method for diagnosing or treating the particular tumor type.

To the extent that the methods and compositions of the present invention find utility in the context of the "prevention" and "prophylaxis" of cancer, such terms are interchangeably used herein to refer to any activity that reduces the burden of mortality or morbidity from disease. Prevention and prophylaxis can occur "at primary, secondary and tertiary prevention levels." While primary prevention and prophylaxis avoid the development of a disease, secondary and tertiary levels of prevention and prophylaxis encompass activities aimed at the prevention and prophylaxis of the progression of a disease and the emergence of symptoms as well as reducing the negative impact of an already established disease by restoring function and reducing disease-related complications. Alternatively, prevention and prophylaxis can include a wide range of prophylactic therapies aimed at alleviating the severity of the particular disorder, e.g. reducing the proliferation and metastasis of tumors.

In the context of the present invention, the treatment and/or prophylaxis of cancer and/or the prevention of postoperative recurrence thereof include any of the following steps, such as the surgical removal of cancer cells, the inhibition of the growth of cancerous cells, the involution or regression of a tumor, the induction of remission and suppression of occurrence of cancer, the tumor regression, and the reduction or inhibition of metastasis. Effective treatment and/or the prophylaxis of cancer decreases mortality and improves the prognosis of individuals having cancer, decreases the levels of tumor markers in the blood, and alleviates detectable symptoms accompanying cancer. For example, reduction or improvement of symptoms constitutes effectively treating and/or the prophylaxis include 10%, 20%, 30% or more reduction, or stable disease.

In the context of the present invention, the term "antibody" refers to immunoglobulins and fragments thereof that are specifically reactive to a designated protein or peptide thereof. An antibody can include human antibodies, primatized antibodies, chimeric antibodies, bispecific antibodies, humanized antibodies, antibodies fused to other proteins or radiolabels, and antibody fragments. Furthermore, an antibody herein is used in the broadest sense and specifically covers intact monoclonal antibodies, polyclonal antibodies, multispecific antibodies (e.g. bispecific antibodies) formed from at least two intact antibodies, and antibody fragments so long as they exhibit the desired biological activity. An "antibody" indicates all classes (e.g. IgA, IgD, IgE, IgG and IgM).

II. Peptides

To demonstrate that peptides derived from TMEM22 function as an antigen recognized by CTLs, peptides derived from TMEM22 (SEQ ID NO: 92) were analyzed to determine whether they were antigen epitopes restricted by HLA-A24 or A2 which are commonly encountered HLA alleles (Date Y et al., Tissue Antigens 47: 93-101, 1996; Kondo A et al., J Immunol 155: 4307-12, 1995; Kubo R T et al., J Immunol 152: 3913-24, 1994).

Candidates of HLA-A24 binding peptides derived from TMEM22 were identified based on their binding affinities to HLA-A24. The following peptides were identified as candidate peptides:

```
TMEM22-A24-9-390,      (SEQ ID NO: 1)
TMEM22-A24-9-274,      (SEQ ID NO: 2)
TMEM22-A24-9-372,      (SEQ ID NO: 3)
TMEM22-A24-9-331,      (SEQ ID NO: 4)
TMEM22-A24-9-385,      (SEQ ID NO: 5)
TMEM22-A24-9-204,      (SEQ ID NO: 6)
TMEM22-A24-9-368,      (SEQ ID NO: 7)
TMEM22-A24-9-37,       (SEQ ID NO: 9)
TMEM22-A24-9-297       (SEQ ID NO: 10)
TMEM22-A24-9-137,      (SEQ ID NO: 11)
TMEM22-A24-9-98,       (SEQ ID NO: 12)
TMEM22-A24-9-197,      (SEQ ID NO: 13)
TMEM22-A24-9-283,      (SEQ ID NO: 14)
TMEM22-A24-9-142,      (SEQ ID NO: 15)
TMEM22-A24-9-375,      (SEQ ID NO: 16)
TMEM22-A24-10-137,     (SEQ ID NO: 18)
TMEM22-A24-10-140,     (SEQ ID NO: 19)
TMEM22-A24-10-153,     (SEQ ID NO: 20)
```

```
TMEM22-A24-10-170,    (SEQ ID NO: 21)
TMEM22-A24-10-204,    (SEQ ID NO: 22)
TMEM22-A24-10-257,    (SEQ ID NO: 23)
TMEM22-A24-10-319,    (SEQ ID NO: 24)
TMEM22-A24-10-355,    (SEQ ID NO: 25)
TMEM22-A24-10-372,    (SEQ ID NO: 26)
TMEM22-A24-10-402,    (SEQ ID NO: 27)
TMEM22-A24-10-282,    (SEQ ID NO: 28)
TMEM22-A24-10-297,    (SEQ ID NO: 29)
TMEM22-A24-10-104,    (SEQ ID NO: 30)
and
TMEM22-A24-10-177.    (SEQ ID NO: 31)
```

Moreover, after in vitro stimulation of T-cells by dendritic cells (DCs) loaded with these peptides, CTLs were successfully established using each of the following peptides:

```
TMEM22-A24-9-390,     (SEQ ID NO: 1)
TMEM22-A24-9-274,     (SEQ ID NO: 2)
TMEM22-A24-9-372,     (SEQ ID NO: 3)
TMEM22-A24-9-331,     (SEQ ID NO: 4)
TMEM22-A24-9-385,     (SEQ ID NO: 5)
TMEM22-A24-9-204,     (SEQ ID NO: 6)
TMEM22-A24-9-297,     (SEQ ID NO: 10)
TMEM22-A24-9-375,     (SEQ ID NO: 16)
TMEM22-A24-10-137,    (SEQ ID NO: 18)
TMEM22-A24-10-204,    (SEQ ID NO: 22)
TMEM22-A24-10-282,    (SEQ ID NO: 28)
and
TMEM22-A24-10-177.    (SEQ ID NO: 31)
```

Candidates of HLA-A2 binding peptides derived from TMEM22 were identified based on their binding affinities to HLA-A2. The following peptides were identified as candidate peptides:

```
TMEM22-A2-9-196,      (SEQ ID NO: 32)
TMEM22-A2-9-262,      (SEQ ID NO: 34)
TMEM22-A2-9-338,      (SEQ ID NO: 35)
TMEM22-A2-9-213,      (SEQ ID NO: 36)
TMEM22-A2-9-379,      (SEQ ID NO: 37)
TMEM22-A2-9-381,      (SEQ ID NO: 38)
TMEM22-A2-9-364,      (SEQ ID NO: 39)
TMEM22-A2-9-320,      (SEQ ID NO: 40)
TMEM22-A2-9-367,      (SEQ ID NO: 41)
TMEM22-A2-9-99,       (SEQ ID NO: 42)
TMEM22-A2-9-380,      (SEQ ID NO: 43)
TMEM22-A2-9-337,      (SEQ ID NO: 44)
TMEM22-A2-9-302,      (SEQ ID NO: 45)
TMEM22-A2-9-112,      (SEQ ID NO: 46)
TMEM22-A2-9-143,      (SEQ ID NO: 47)
TMEM22-A2-9-218,      (SEQ ID NO: 48)
TMEM22-A2-9-225,      (SEQ ID NO: 49)
TMEM22-A2-9-265,      (SEQ ID NO: 50)
TMEM22-A2-9-357,      (SEQ ID NO: 51)
TMEM22-A2-9-230,      (SEQ ID NO: 52)
TMEM22-A2-9-345,      (SEQ ID NO: 53)
TMEM22-A2-9-360,      (SEQ ID NO: 54)
TMEM22-A2-9-217,      (SEQ ID NO: 55)
TMEM22-A2-9-211,      (SEQ ID NO: 56)
TMEM22-A2-9-234,      (SEQ ID NO: 57)
TMEM22-A2-9-123,      (SEQ ID NO: 58)
TMEM22-A2-9-247,      (SEQ ID NO: 59)
TMEM22-A2-9-105,      (SEQ ID NO: 60)
TMEM22-A2-10-217,     (SEQ ID NO: 61)
TMEM22-A2-10-304,     (SEQ ID NO: 62)
TMEM22-A2-10-212,     (SEQ ID NO: 63)
TMEM22-A2-10-320,     (SEQ ID NO: 64)
TMEM22-A2-10-167,     (SEQ ID NO: 65)
TMEM22-A2-10-338,     (SEQ ID NO: 66)
TMEM22-A2-10-363,     (SEQ ID NO: 67)
TMEM22-A2-10-296,     (SEQ ID NO: 68)
TMEM22-A2-10-112,     (SEQ ID NO: 69)
TMEM22-A2-10-103,     (SEQ ID NO: 70)
TMEM22-A2-10-136,     (SEQ ID NO: 71)
TMEM22-A2-10-265,     (SEQ ID NO: 72)
TMEM22-A2-10-337,     (SEQ ID NO: 73)
TMEM22-A2-10-195,     (SEQ ID NO: 74)
TMEM22-A2-10-205,     (SEQ ID NO: 75)
TMEM22-A2-10-269,     (SEQ ID NO: 76)
TMEM22-A2-10-229,     (SEQ ID NO: 77)
TMEM22-A2-10-148,     (SEQ ID NO: 78)
TMEM22-A2-10-133,     (SEQ ID NO: 79)
TMEM22-A2-10-359,     (SEQ ID NO: 80)
TMEM22-A2-10-380,     (SEQ ID NO: 81)
TMEM22-A2-10-224,     (SEQ ID NO: 82)
```

-continued

| | |
|---|---|
| TMEM22-A2-10-356, | (SEQ ID NO: 83) |
| TMEM22-A2-10-379, | (SEQ ID NO: 84) |
| TMEM22-A2-10-291, | (SEQ ID NO: 85) |
| TMEM22-A2-10-301, | (SEQ ID NO: 86) |
| TMEM22-A2-10-378, | (SEQ ID NO: 87) |
| TMEM22-A2-10-302, | (SEQ ID NO: 88) |
| TMEM22-A2-10-287 and | (SEQ ID NO: 89) |
| TMEM22-A2-10-130. | (SEQ ID NO: 90) |

Moreover, after in vitro stimulation of T-cells by dendritic cells (DCs) pulsed (loaded) with these peptides, CTLs were successfully established using each of the following peptides;

| | |
|---|---|
| TMEM22-A2-9-338, | (SEQ ID NO: 35) |
| TMEM22-A2-9-381, | (SEQ ID NO: 38) |
| TMEM22-A2-9-367, | (SEQ ID NO: 41) |
| TMEM22-A2-9-218, | (SEQ ID NO: 48) |
| TMEM22-A2-10-217, | (SEQ ID NO: 61) |
| TMEM22-A2-10-304, | (SEQ ID NO: 62) |
| TMEM22-A2-10-167, | (SEQ ID NO: 65) |
| TMEM22-A2-10-363, | (SEQ ID NO: 67) |
| TMEM22-A2-10-103, | (SEQ ID NO: 70) |
| TMEM22-A2-10-195, | (SEQ ID NO: 74) |
| TMEM22-A2-10-229 and | (SEQ ID NO: 77) |
| TMEM22-A2-10-356. | (SEQ ID NO: 83) |

These established CTLs show potent specific CTL activity against target cells pulsed with respective peptides. The results herein demonstrate that TMEM22 is an antigen recognized by CTL and that the peptides are epitope peptides of TMEM22 restricted by HLA-A24 or HLA-A2.

Since the TMEM22 gene is over expressed in cancer cells and tissues, including, but not limited to, those of AML, bladder cancer, CCC, esophagus cancer, lymphoma, prostate cancer, RCC and SCLC but is not expressed in most normal organs, it is a good target for immunotherapy. Thus, the present invention provides nonapeptides (peptides composed of nine amino acid residues) and decapeptides (peptides composed of ten amino acid residues) corresponding to CTL-recognized epitopes of TMEM22. Preferred examples of nonapeptides and decapeptides of the present invention include those peptides having an amino acid sequence selected from among SEQ ID NOs: 1, 2, 3, 4, 5, 6, 10, 12, 16, 18, 19, 22, 28, 31, 35, 38, 41, 48, 61, 62, 65, 67, 70, 74, 77 and 83.

Generally, software programs presently available on the Internet, such as those described in Parker K C et al., J Immunol 1994 Jan. 1, 152(1): 163-75, Buus et al. (Tissue Antigens., 62:378-84, 2003) and Nielsen et al. (Protein Sci., 12:1007-17, 2003, Bioinformatics, 20(9):1388-97, 2004), can be used to calculate the binding affinities between various peptides and HLA antigens in silico. Binding affinity with HLA antigens can be measured as described, for example, in the references to Parker K C et al., J Immunol 1994 Jan. 1, 152(1): 163-75; and Kuzushima K et al., Blood 2001, 98(6): 1872-81. Methods for determining binding affinity are described, for example, in the Journal of Immunological Methods, 1995, 185: 181-190 and Protein Science, 2000, 9: 1838-1846. Therefore, one can use such software programs to select those fragments derived from TMEM22 that have high binding affinity with HLA antigens. Accordingly, the present invention encompasses peptides composed of any fragments derived from TMEM22 that bind with HLA antigens identified using such known programs. The peptide of the present invention may be full length peptide of TMEM22.

The peptides of the present invention can be flanked with additional amino acid residues so long as the resulting peptide retains its CTL inducibility. The particular amino acid residues flanking the present peptides may be composed of any kind of amino acid, so long as they do not impair the CTL inducibility of the original peptide. Thus, the present invention encompasses peptides that include the peptides derived from TMEM22 and have binding affinity to HLA antigens. Such peptides are typically less than about 40 amino acids, often less than about 20 amino acids, usually less than about 15 amino acids.

In general, the modification of one, two or more amino acids in a peptide will not influence the function of the peptide, and in some cases will even enhance the desired function of the original protein. In fact, modified peptides (i.e., peptides composed of an amino acid sequence in which one, two or several amino acid residues have been modified (i.e., substituted, deleted, added or inserted as compared to an original reference sequence) have been known to retain the biological activity of the original peptide (Mark et al., Proc Natl Acad Sci USA 1984, 81: 5662-6; Zoller and Smith, Nucleic Acids Res 1982, 10: 6487-500; Dalbadie-McFarland et al., Proc Natl Acad Sci USA 1982, 79: 6409-13). Thus, in one embodiment, the peptides of the present invention may have both CTL inducibility and an amino acid sequence selected from among SEQ ID NOs: 1, 2, 3, 4, 5, 6, 10, 12, 16, 18, 19, 22, 28, 31, 35, 38, 41, 48, 61, 62, 65, 67, 70, 74, 77 and 83, wherein one, two or even more amino acids are added, inserted and/or substituted.

Those skill in the art recognize that individual additions or substitutions to an amino acid sequence which alters a single amino acid or a small percentage of amino acids tend to result in the conservation of the properties of the original amino acid side-chain. As such, they are often referred to as "conservative substitutions" or "conservative modifications", wherein the alteration of a protein results in a modified protein having a function analogous to the original protein. Conservative substitution tables providing functionally similar amino acids are well known in the art. Examples of amino acid side chain characteristics that are desirable to conserve include, for example, hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). In addition, the following eight groups each contain amino acids that are accepted in the art as conservative substitutions for one another:

1) Alanine (A), Glycine (G);
2) Aspartic acid (D), Glutamic acid (E);
3) Asparagine (N), Glutamine (Q);
4) Arginine (R), Lysine (K);

5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins 1984).

Such conservatively modified peptides are also considered to be peptides of the present invention. However, peptides of the present invention are not restricted thereto and can include non-conservative modifications, so long as the resulting modified peptide retains the CTL inducibility of the original peptide. Furthermore, modified peptides should not exclude CTL inducible peptides of polymorphic variants, interspecies homologues, and alleles of TMEM22.

Amino acid residues may be inserted, substituted or added to the peptides of the present invention or, alternatively, amino acid residues may be deleted therefrom to achieve a higher binding affinity. To retain the requisite CTL inducibility one preferably modifies (insert, delete, add and/or substitute) only a small number (for example, 1, 2 or several) or a small percentage of amino acids. Herein, the term "several" means 5 or fewer amino acids, for example, 4, 3 or fewer. The percentage of amino acids to be modified is preferably 20% or less, more preferably 15% of less, even more preferably 10% or less or 1 to 5%.

When used in the context of immunotherapy, the present peptides should be presented on the surface of a cell or exosome, preferably as a complex with an HLA antigen. In addition to peptides that are naturally displayed, since the regularity of the sequences of peptides displayed by binding to HLA antigens is already known (J Immunol 1994, 152: 3913; Immunogenetics 1995, 41: 178; J Immunol 1994, 155: 4307), modifications based on such regularity can be introduced into the immunogenic peptides of the invention.

For example, it may be desirable to substitute the second amino acid from the N-terminus substituted with phenylalanine, tyrosine, methionine, or tryptophan, and/or the amino acid at the C-terminus with phenylalanine, leucine, isoleucine, tryptophan, or methionine in order to increase the HLA-A24 binding. Thus, peptides having the amino acid sequences selected from among SEQ ID NOs: 1, 2, 3, 4, 5, 6, 10, 12, 16, 18, 19, 22, 28 and 31 wherein the second amino acid from the N-terminus of the amino acid sequence of SEQ ID NOs is substituted with phenylalanine, tyrosine, methionine, or tryptophan, and peptides, and/or wherein the C-terminus of the amino acid sequence of the SEQ ID NOs is substituted with phenylalanine, leucine, isoleucine, tryptophan, or methionine are encompassed by the present invention.

Alternatively, in peptides showing high HLA-A2 binding affinity, it may be desirable to substitute the second amino acid from the N-terminus with leucine or methionine or the amino acid at the C-terminus with valine or leucine. Thus, peptides having amino acid sequences selected from among SEQ ID NOs: 35, 38, 41, 48, 61, 62, 65, 67, 70, 74, 77 and 83 wherein the second amino acid from the N-terminus of the amino acid sequence of said SEQ ID NO is substituted with leucine or methionine, and peptides, and/or wherein the C-terminus of the amino acid sequence of said SEQ ID NO is substituted with valine or leucine are encompassed by the present invention.

Substitutions may be introduced not only at the terminal amino acids but also at the position of potential T cell receptor (TCR) recognition of peptides. Several studies have demonstrated that a peptide with amino acid substitutions may have equal to or better function than that of the original, for example, CAP1, p53$_{(264-272)}$, Her-2/neu$_{(369-377)}$ or gp100$_{(209-217)}$ (Zaremba et al. Cancer Res. 57, 4570-4577, 1997, T. K. Hoffmann et al. J. Immunol. (2002) Feb. 1; 168 (3):1338-47., S. O. Dionne et al. Cancer Immunol immunother. (2003) 52: 199-206 and S. O. Dionne et al. Cancer Immunology, Immunotherapy (2004) 53, 307-314).

The present invention also contemplates the addition of one, two or several amino acids to the N and/or C-terminus of the described peptides. Such modified peptides having high HLA antigen binding affinity and retained CTL inducibility are also included in the present invention.

However, when the peptide sequence is identical to a portion of the amino acid sequence of an endogenous or exogenous protein having a different function, side effects such as autoimmune disorders and/or allergic symptoms against specific substances may be induced. Therefore, it is preferable to first perform homology searches using available databases to avoid situations in which the sequence of the peptide matches the amino acid sequence of another protein. When it becomes clear from the homology searches that there exists not even a peptide with 1 or 2 amino acid differences as compared to the objective peptide, the objective peptide can be modified in order to increase its binding affinity with HLA antigens, and/or increase its CTL inducibility without any danger of such side effects.

Although peptides having high binding affinity to the HLA antigens as described above are expected to be highly effective, the candidate peptides, which are selected according to the presence of high binding affinity as an indicator, are further examined for the presence of CTL inducibility. Herein, the phrase "CTL inducibility" indicates the ability of the peptide to induce CTLs when presented on antigen-presenting cells (APCs). Further, "CTL inducibility" includes the ability of the peptide to induce CTL activation, CTL proliferation, promote CTL lysis of target cells, and to increase CTL IFN-gamma production.

Confirmation of CTL inducibility is accomplished by inducing APCs carrying human MHC antigens (for example, B-lymphocytes, macrophages, and dendritic cells (DCs)), or more specifically DCs derived from human peripheral blood mononuclear leukocytes, and after stimulation with the peptides, mixing with CD8-positive cells, and then measuring the IFN-gamma produced and released by CTL against the target cells. As the reaction system, transgenic animals that have been produced to express a human HLA antigen (for example, those described in BenMohamed L, Krishnan R, Longmate J, Auge C, Low L, Primus J, Diamond D J, Hum Immunol 2000 August, 61(8): 764-79, Related Articles, Books, Linkout Induction of CTL response by a minimal epitope vaccine in HLA A*0201/DR1 transgenic mice: dependence on HLA class II restricted T(H) response) can be used. For example, the target cells can be radio-labeled with $^{51}$Cr and such, and cytotoxic activity can be calculated from radioactivity released from the target cells. Alternatively, CTL inducibility can be assessed by measuring IFN-gamma produced and released by CTL in the presence of APCs that carry immobilized peptides, and visualizing the inhibition zone on the media using anti-IFN-gamma monoclonal antibodies.

As a result of examining the CTL inducibility of the peptides as described above, it was discovered that nonapeptides or decapeptides selected from among peptides having the amino acid sequences indicated by SEQ ID NOs: 1, 2, 3, 4, 5, 6, 10, 12, 16, 18, 19, 22, 28, 31 35, 38, 41, 48, 61, 62, 65, 67, 70, 74, 77 and 83 showed particularly high CTL inducibility as well as high binding affinity to an HLA antigen. Thus, these peptides are exemplified as preferred embodiments of the present invention.

Furthermore, the results of homology analyses showed that such peptides do not have significant homology with peptides derived from any other known human gene products. This lowers the possibility of unknown or undesired immune responses arising when used for immunotherapy. Therefore, also from this aspect, these peptides are useful for eliciting immunity against TMEM22 in cancer patients. Thus, the peptides of the present invention, preferably, peptides consisting of the amino acid sequence selected from among SEQ ID NOs: 1, 2, 3, 4, 5, 6, 10, 12, 16, 18, 19, 22, 28, 31, 35, 38, 41, 48, 61, 62, 65, 67, 70, 74, 77 and 83.

In addition to the above-described modifications, the peptides of the present invention may also be linked to other peptides, so long as the resulting linked peptide retains the requisite CTL inducibility. Examples of suitable "other" peptides include: the peptides of the present invention or the CTL inducible peptides derived from other TAAs. The linkers between the peptides are well known in the art, for example, AAY (P. M. Daftarian et al., J Trans Med 2007, 5:26), AAA, NKRK (R. P. M. Sutmuller et al., J. Immunol. 2000, 165: 7308-7315) or K (S. Ota et al., Can Res. 62, 1471-1476, K. S. Kawamura et al., J. Immunol. 2002, 168: 5709-5715).

For example, non-TMEM22 tumor associated antigen peptides also can be used substantially simultaneously to increase the immune response via HLA class I and/or class II. It is well established that cancer cells can express more than one tumor associated gene. Thus it is within the scope of routine experimentation for one of ordinary skill in the art to determine whether a particular subject expresses additional tumor associated genes, and then to include HLA class I and/or HLA class II binding peptides derived from expression products of such genes in TMEM22 compositions or vaccines according to the present invention.

Examples of HLA class I and HLA class II binding peptides will be known to one of ordinary skill in the art (for example, see Coulie, Stem Cells 13:393-403, 1995), and can be used in the invention in a like manner as those disclosed herein. One of ordinary skill in the art can prepare polypeptides including one or more TMEM22 peptides and one or more of the non-TMEM22 peptides, or nucleic acids encoding such polypeptides, according to standard procedures of molecular biology.

The above linked peptides are referred to herein as "polytopes", i.e., groups of two or more potentially immunogenic or immune response stimulating peptides which can be joined together in various arrangements (e.g., concatenated, overlapping). The polypore (or nucleic acid encoding the polytope) can be administered in a standard immunization protocol, e.g., to animals, to test the effectiveness of the polytope in stimulating, enhancing and/or provoking an immune response.

The peptides can be joined together directly or via the use of flanking sequences to form polytopes, and the use of polytopes as vaccines is well known in the art (see, e.g., Thomson et al., Proc. Natl. Acad. Sci. USA 92(13):5845-5849, 1995; Gilbert et al., Nature Biotechnol. 15(12):1280-1284, 1997; Thomson et al., J. Immunol. 157(2):822-826, 1996; Tarn et al., J. Exp. Med. 171(1):299-306, 1990). Polytopes containing various numbers and combinations of epitopes can be prepared and tested for recognition by CTLs and for efficacy in increasing an immune response.

Furthermore, the described peptides can be further linked to other substances, so long as they retain the CTL inducibility of the original peptide. Exemplary substances include: peptides, lipids, sugar and sugar chains, acetyl groups, natural and synthetic polymers, etc. The present peptides can contain modifications such as glycosylation, side chain oxidation, and/or phosphorylation; so long as the modifications do not destroy the biological activity of the original peptide. These kinds of modifications may confer additional functions (e.g., targeting function, and delivery function) and/or stabilize the peptides.

For example, to increase the in vivo stability of a polypeptide, it is known in the art to introduce D-amino acids, amino acid mimetics or unnatural amino acids; this concept can also be adopted to the present polypeptides. The stability of a polypeptide can be assayed in a number of ways. For instance, peptidases and various biological media, such as human plasma and serum, can be used to test stability (see, e.g., Verhoef et al., Eur J Drug Metab Pharmacokin 1986, 11: 291-302).

Moreover, as noted above, among the modified peptides that are substituted, deleted or added by one, two or several amino acid residues, those having same or higher activity as compared to original peptides can be screened for or selected. The present invention, therefore, also provides the method of screening for or selecting modified peptides having same or higher activity as compared to originals. For example, the method may include the steps of:

a: substituting, deleting or adding at least one amino acid residue of a peptide of the present invention,
b: determining the activity of the peptide, and
c: selecting the peptide having same or higher activity as compared to the original.

Herein, the activity may include MHC binding activity, APC or CTL inducibility and cytotoxic activity.

When the peptides of the present intention include a cystein residue, the peptides tend to form dimers via a disulfide bond between SH groups of the cyctein residues. Therefore, dimers of the peptide of the present invention are also included in the peptides of the present invention.

Herein, the peptides of the present invention can also be described as "TMEM22 peptide(s)" or "TMEM22 polypeptide(s)".

III. Preparation of TMEM22 Peptides

The peptides of the invention can be prepared using well known techniques. For example, the peptides can be prepared synthetically, using recombinant DNA technology or chemical synthesis. The peptides of the invention can be synthesized individually or as longer polypeptides composed of two or more peptides. The peptides can then be isolated i.e., purified or isolated so as to be substantially free of other naturally occurring host cell proteins and fragments thereof, or any other chemical substances.

The peptides of the present invention may contain modifications, such as glycosylation, side chain oxidation, or phosphorylation provided such modifications do not destroy the biological activity of the original peptide. Other illustrative modifications include incorporation of D-amino acids or other amino acid mimetics that may be used, for example, to increase the serum half life of the peptides.

A peptide of the present invention can be obtained through chemical synthesis based on the selected amino acid sequence. Examples of conventional peptide synthesis methods that can be adapted to the synthesis include, but are not limited to:

(i) Peptide Synthesis, Interscience, New York, 1966;
(ii) The Proteins, Vol. 2, Academic Press, New York, 1976;
(iii) Peptide Synthesis (in Japanese), Maruzen Co., 1975;
(iv) Basics and Experiment of Peptide Synthesis (in Japanese), Maruzen Co., 1985;
(v) Development of Pharmaceuticals (second volume) (in Japanese), Vol. 14 (peptide synthesis), Hirokawa, 1991;

(vi) WO99/67288; and
(vii) Barany G. & Merrifield R. B., Peptides Vol. 2, "Solid Phase Peptide Synthesis", Academic Press, New York, 1980, 100-118.

Alternatively, the present peptides can be obtained adapting any known genetic engineering methods for producing peptides (e.g., Morrison J, J Bacteriology 1977, 132: 349-51; Clark-Curtiss & Curtiss, Methods in Enzymology (eds. Wu et al.) 1983, 101: 347-62). For example, first, a suitable vector harboring a polynucleotide encoding the objective peptide in an expressible form (e.g., downstream of a regulatory sequence corresponding to a promoter sequence) is prepared and transformed into a suitable host cell. The host cell is then cultured to produce the peptide of interest. The peptide can also be produced in vitro adapting an in vitro translation system.

IV. Polynucleotides

The present invention also provides a polynucleotide which encodes any of the afore-mentioned peptides of the present invention. These include polynucleotides derived from the natural occurring TMEM22 gene (GenBank Accession No. NM_025246, NM_001097599, NM_001097600 (for example, SEQ ID NO: 91)) as well as those having a conservatively modified nucleotide sequence thereof. Herein, the phrase "conservatively modified nucleotide sequence" refers to sequences which encode identical or essentially identical amino acid sequences. Due to the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a peptide also describes every possible silent variation of the nucleic acid. One of ordinary skill in the art will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a peptide is implicitly described in each disclosed sequence.

The polynucleotide of the present invention can be composed of DNA, RNA, and derivatives thereof. A DNA is suitably composed of bases such as A, T, C, and G, and T is replaced by U in an RNA. One of skill will recognize that non-naturally occurring bases be included in polynucleotides, as well.

The polynucleotide of the present invention can encode multiple peptides of the present invention with or without intervening amino acid sequences in between. For example, the intervening amino acid sequence can provide a cleavage site (e.g., enzyme recognition sequence) of the polynucleotide or the translated peptides. Furthermore, the polynucleotide can include any additional sequences to the coding sequence encoding the peptide of the present invention. For example, the polynucleotide can be a recombinant polynucleotide that includes regulatory sequences required for the expression of the peptide or can be an expression vector (plasmid) with marker genes and such. In general, such recombinant polynucleotides can be prepared by the manipulation of polynucleotides through conventional recombinant techniques using, for example, polymerases and endonucleases.

Both recombinant and chemical synthesis techniques can be used to produce the polynucleotides of the present invention. For example, a polynucleotide can be produced by insertion into an appropriate vector, which can be expressed when transfected into a competent cell. Alternatively, a polynucleotide can be amplified using PCR techniques or expression in suitable hosts (see, e.g., Sambrook et al., Molecular Cloning: A Laboratory Manual, Cold Spring Harbor Laboratory, New York, 1989). Alternatively, a polynucleotide can be synthesized using the solid phase techniques, as described in Beaucage S L & Iyer R P, Tetrahedron 1992, 48: 2223-311; Matthes et al., EMBO J. 1984, 3: 801-5.

V. Exosomes

The present invention further provides intracellular vesicles called exosomes, which present complexes formed between the peptides of this invention and HLA antigens on their surface. Exosomes can be prepared, for example, using the methods detailed in Japanese Patent Application Kohyo Publications Nos. Hei 11-510507 and WO99/03499, and can be prepared using APCs obtained from patients who are subject to treatment and/or prevention. The exosomes of this invention can be inoculated as vaccines, in a fashion similar to the peptides of this invention.

The type of HLA antigens contained in the complexes must match that of the subject requiring treatment and/or prevention. For example, in the Japanese population, HLA-A24 and HLA-A2 (particularly, HLA-A*2402, HLA-A*0201 and HLA-A*0206) are prevalent and therefore would be appropriate for treatment of a Japanese patient. The use of the A24 type or the A2 type that is highly expressed among the Japanese and Caucasian is favorable for obtaining effective results, and subtypes such as HLA-A*2402, HLA-A*0201 and HLA-A*0206 also find use. Typically, in the clinic, the type of HLA antigen of the patient requiring treatment is investigated in advance, which enables the appropriate selection of peptides having high levels of binding affinity to the particular antigen, or having CTL inducibility by antigen presentation. Furthermore, in order to obtain peptides having both high binding affinity and CTL inducibility, substitution, insertion and/or addition of 1, 2, or several amino acids can be performed based on the amino acid sequence of the naturally occurring TMEM22 partial peptide.

When using the A24 type HLA antigen for the exosome of the present invention, the peptides having a sequence of any one of SEQ ID NOs: 1, 2, 3, 4, 5, 6, 10, 12, 16, 18, 19, 22, 28 and 31 find use.

Alternatively, when using the A2 type HLA antigen for the exosome of the present invention, peptides having a sequence selected from among SEQ ID NOs: 35, 38, 41, 48, 61, 62, 65, 67, 70, 74, 77 and 83 find use.

VI. Antigen-presenting Cells (APCs)

The present invention also provides isolated APCs that present complexes formed between HLA antigens and the peptides of this invention on its surface. The APCs can be derived from patients who are subject to treatment and/or prevention, and can be administered as vaccines by themselves or in combination with other drugs including the peptides of this invention, exosomes, or CTLs.

The APCs are not limited to a particular kind of cells and include dendritic cells (DCs), Langerhans cells, macrophages, B cells, and activated T cells, which are known to present proteinaceous antigens on their cell surface so as to be recognized by lymphocytes. Since DC is a representative APC having the strongest CTL inducing action among APCs, DCs find use as the APCs of the present invention.

For example, the APCs of the present invention can be obtained by inducing DCs from peripheral blood monocytes and then contacting (stimulating) them with the peptides of this invention in vitro, ex vivo or in vivo. When the peptides of this invention are administered to the subjects, APCs that present the peptides of this invention are induced in the body of the subject. Therefore, the APCs of this invention can be obtained by collecting the APCs from the subject after administering the peptides of this invention to the subject. Alternatively, the APCs of this invention can be obtained by contacting APCs collected from a subject with the peptide of this invention.

The APCs of the present invention can be administered alone or in combination with other drugs including the peptides, exosomes or CTLs of this invention to a subject for inducing immune response against cancer in the subject. For example, the ex vivo ad-ministration can include steps of:
 a: collecting APCs from a first subject,
 b: contacting the APCs of step a, with the peptide and
 c: administering the APCs of step b to a second subject.

The first subject and the second subject can be the same individual, or may be different individuals. Alternatively, according to the present invention, use of the peptides of the present invention for manufacturing a pharmaceutical composition inducing antigen-presenting cells is provided. In addition, the present invention provides a method or process for manufacturing a pharmaceutical composition inducing antigen-presenting cells. Further, the present invention also provides the peptides of the present invention for inducing antigen-presenting cells. The APCs obtained by step b can be administered as a vaccine for treating and/or preventing cancer, examples of which include but are not limited to, AML, bladder cancer, CCC, esophagus cancer, lymphoma, prostate cancer, RCC and SCLC.

The present invention also provides a method or process for manufacturing a pharmaceutical composition for inducing APCs, wherein the method includes the step of admixing or formulating the peptide of the invention with a pharmaceutically acceptable carrier.

According to an aspect of the present invention, the APCs have a high level of CTL inducibility. In the term of "high level of CTL inducibility", the high level is relative to the level of that by APC contacting with no peptide or peptides which cannot induce the CTL. Such APCs having a high level of CTL inducibility can be prepared by a method which includes the step of transferring a polynucleotide encoding the peptide of this invention to APCs in vitro as well as the method mentioned above. The introduced genes can be in the form of DNAs or RNAs. Examples of methods for introduction include, without particular limitations, various methods conventionally performed in this field, such as lipofection, electroporation, and calcium phosphate method. More specifically, it can be performed as described in Cancer Res 1996, 56: 5672-7; J Immunol 1998, 161: 5607-13; J Exp Med 1996, 184: 465-72; Published Japanese Translation of International Publication No. 2000-509281. By transferring the gene into APCs, the gene undergoes transcription, translation, and such in the cell, and then the obtained protein is processed by MHC Class I or Class II, and proceeds through a presentation pathway to present peptides.

VII. Cytotoxic T Lymphocytes (CTLs)

A CTL induced against any of the peptides of the present invention strengthens the immune response targeting cancer cells in vivo and thus can be used as vaccines in a fashion similar to the peptides per se. Thus, the present invention also provides isolated CTLs that are specifically induced or activated by any of the present peptides.

Such CTLs can be obtained by (1) administering the peptide(s) of the present invention to a subject, collecting CTLs from the subject; or (2) contacting (stimulating) subject-derived APCs, and CD8-positive cells, or peripheral blood mononuclear leukocytes in vitro with the peptide(s) of the present invention and then isolating CTLs; or (3) contacting CD8-positive cells or peripheral blood mononuclear leukocytes in vitro with APCs or exosomes presenting a complex of an HLA antigen and the present peptide on its surface and then isolating CTLs; or (4) introducing a gene including a polynucleotide encoding a T cell receptor (TCR) subunit binding to the peptide of this invention to the CTLs. The aforementioned APCs and exosomes can be prepared by methods described above and the method of (4) is detailed bellow in section "VIII. T cell receptor (TCR)".

The CTLs of this invention can be derived from patients who are subject to treatment and/or prevention, and can be administered by themselves or in combination with other drugs including the peptides of this invention or exosomes for the purpose of regulating effects. The obtained CTLs act specifically against target cells presenting the peptides of this invention, for example, the same peptides used for induction. The target cells can be cells that endogenously express TMEM22, such as cancer cells, or cells that are transfected with the TMEM22 gene; and cells that present a peptide of this invention on the cell surface due to stimulation by the peptide can also serve as targets of activated CTL attack.

VIII. T Cell Receptor (TCR)

The present invention also provides a composition containing nucleic acids encoding polypeptides that are capable of forming a subunit of a T cell receptor (TCR), and methods of using the same. The TCR subunits have the ability to form TCRs that confer specificity to T cells against tumor cells expressing TMEM22. By using the known methods in the art, the nucleic acids of alpha- and beta-chains as the TCR subunits of the CTL induced with one or more peptides of this invention can be identified (WO2007/032255 and Morgan et al., J Immunol, 171, 3288 (2003)). For example, the PCR method is preferred to analyze the TCR. The PCR primers for the analysis can be, for example, 5'-R primers (5'-gtctaccaggcattcgcttcat-3') as 5' side primers (SEQ ID NO: 93) and 3-TRa-C primers (5'-tcagctggaccacagccgcagcgt-3') specific to TCR alpha chain C region (SEQ ID NO: 94), 3-TRb-C1 primers (5'-tcagaaatcctttctcttgac-3') specific to TCR beta chain C1 region (SEQ ID NO: 95) or 3-TRbeta-C2 primers (5'-ctagcctctggaatcctttctctt-3') specific to TCR beta chain C2 region (SEQ ID NO: 96) as 3' side primers, but not limited. The derivative TCRs can bind target cells displaying the TMEM22 peptide with high avidity, and optionally mediate efficient killing of target cells presenting the TMEM22 peptide in vivo and in vitro.

The nucleic acids encoding the TCR subunits can be incorporated into suitable vectors e.g. retroviral vectors. These vectors are well known in the art. The nucleic acids or the vectors containing them usefully can be transferred into a T cell, for example, a T cell from a patient. Advantageously, the invention provides an off-the-shelf composition allowing rapid modification of a patient's own T cells (or those of another mammal) to rapidly and easily produce modified T cells having excellent cancer cell killing properties.

The specific TCR is a receptor capable of specifically recognizing a complex of a peptide of the present invention and HLA molecule, giving a T cell specific activity against the target cell when the TCR on the surface of the T cell. A specific recognition of the above complex may be confirmed by any known methods, and preferred methods include, for example, tetramer analysis using HLA molecule and peptide of the invention, and ELISPOT assay. By performing the ELISPOT assay, it can be confirmed that a T cell expressing the TCR on the cell surface recognizes a cell by the TCR, and that the signal is transmitted intracellularly. The confirmation that the above-mentioned complex can give a T cell cytotoxic activity when the complex exists on the T cell surface may also be carried out by a known method. A preferred method includes, for example, the determination of cytotoxic activity against an HLA positive target cell, such as chromium release assay.

Also, the present invention provides CTLs which are prepared by transduction with the nucleic acids encoding the TCR subunits polypeptides that bind to the TMEM22 peptide of, e.g., SEQ ID NOs: 1, 2, 3, 4, 5, 6, 10, 12, 16, 18, 19, 22, 28 and 31 in the context of HLA-A24, and also the peptides of SEQ ID NOs: 35, 38, 41, 48, 61, 62, 65, 67, 70, 74, 77 and 83 in the context of HLA-A2.

The transduced CTLs are capable of homing to cancer cells in vivo, and can be expanded by well known in vitro culturing methods (e.g., Kawakami et al., J. Immunol., 142, 3452-3461 (1989)). The CTLs of the invention can be used to form an immunogenic composition useful in treating or the prevention of cancer in a patient in need of therapy or protection (WO2006/031221).

IX. Pharmaceutical Agents, Substances, or Compositions

Since TMEM22 expression is specifically elevated in cancers including AML, bladder cancer, CCC, esophagus cancer, lymphoma, prostate cancer, RCC and SCLC, as compared with normal tissue, the peptides of the present invention or polynucleotides encoding such peptides can be used for the treatment and/or for the prophylaxis of cancer or tumor, and/or prevention of postoperative recurrence thereof. Thus, the present invention provides a pharmaceutical agent, substance or composition for treating and/or for the prophylaxis of cancer or tumor, and/or prevention of post-operative recurrence thereof, which includes as an active ingredient one or more of the peptides of the present invention, or polynucleotides encoding the peptides. Alternatively, the present peptides can be expressed on the surface of any of the foregoing exosomes or cells, such as APCs for the use as pharmaceutical agents, substances or compositions. In addition, the aforementioned CTLs which target any of the peptides of the invention can also be used as the active ingredient of the present pharmaceutical agents, substances or compositions.

The present pharmaceutical agents, substances or compositions find use as a vaccine. In the present invention, the phrase "vaccine" (also referred to as an immunogenic composition) refers to a substance that has the function to induce anti-tumor immunity upon inoculation into animals.

The pharmaceutical agents, substances or compositions of the present invention can be used to treat and/or prevent cancers, and/or prevention of postoperative recurrence thereof in subjects or patients including human and any other mammal including, but not limited to, mouse, rat, guinea-pig, rabbit, cat, dog, sheep, goat, pig, cattle, horse, monkey, baboon, and chimpanzee, particularly a commercially important animal or a domesticated animal.

In another embodiment, the present invention also provides the use of an active ingredient in manufacturing a pharmaceutical composition or agent for treating cancer or tumor, said active ingredient selected from among:
  (a) a peptide of the present invention;
  (b) a nucleic acid encoding such a peptide as disclosed herein in an expressible form;
  (c) an APC or an exosome presenting a peptide of the present invention on its surface; and
  (d) a cytotoxic T cell of the present invention.

Alternatively, the present invention further provides an active ingredient for use in treating cancer, or tumor, said active ingredient selected from among:
  (a) a peptide of the present invention;
  (b) a nucleic acid encoding such a peptide as disclosed herein in an expressible form;
  (c) an APC or an exosome presenting a peptide of the present invention on its surface; and
  (d) a cytotoxic T cell of the present invention.

Alternatively, the present invention further provides a method or process for manufacturing a pharmaceutical composition or agent for treating cancer or tumor, wherein the method or process includes the step of formulating a pharmaceutically or physiologically acceptable carrier with an active ingredient selected from among:
  (a) a peptide of the present invention;
  (b) a nucleic acid encoding such a peptide as disclosed herein in an expressible form;
  (c) an APC or an exosome presenting a peptide of the present invention on its surface; and
  (d) a cytotoxic T cell of the present invention.

In another embodiment, the present invention also provides a method or process for manufacturing a pharmaceutical composition or agent for treating cancer or tumor, wherein the method or process includes the steps of admixing an active ingredient with a pharmaceutically or physiologically acceptable carrier, wherein the active ingredient is selected from among:
  (a) a peptide of the present invention;
  (b) a nucleic acid encoding such a peptide as disclosed herein in an expressible form;
  (c) an APC or an exosome presenting a peptide of the present invention on its surface; and
  (d) a cytotoxic T cell of the present invention.

Alternatively, the pharmaceutical composition or agent or the present invention may be used for either or both the prophylaxis of cancer or tumor and prevention of post-operative recurrence thereof.

The present pharmaceutical agents, substances or compositions find use as a vaccine. As noted above, in the context of the present invention, the phrase "vaccine" (also referred to as an "immunogenic composition") refers to a substance that has the function to induce anti-tumor immunity upon inoculation into animals.

The pharmaceutical agents, substances or compositions of the present invention can be used to treat and/or prevent cancers or tumors, and/or prevention of postoperative recurrence thereof in subjects or patients including human and any other mammal including, but not limited to, mouse, rat, guinea-pig, rabbit, cat, dog, sheep, goat, pig, cattle, horse, monkey, baboon, and chimpanzee, particularly a commercially important animal or a domesticated animal.

According to the present invention, peptides having an amino acid sequence selected from among SEQ ID NOs: 1, 2, 3, 4, 5, 6, 10, 12, 16, 18, 19, 22, 28 and 31 have been found to be HLA-A24 restricted epitope peptides or candidates and also SEQ ID NOs: 35, 38, 41, 48, 61, 62, 65, 67, 70, 74, 77 and 83 have been found of be HLA-A2 restricted epitope peptides or the candidates that can induce potent and specific immune response. Therefore, the present pharmaceutical agents, substances or compositions which include any of these peptides having the amino acid sequences of SEQ ID NOs: 1, 2, 3, 4, 5, 6, 10, 12, 16, 18, 19, 22, 28, 31 and 35, 38, 41, 48, 61, 62, 65, 67, 70, 74, 77, 83 are particularly suited for the administration to subjects whose HLA antigen is HLA-A24 and HLA-A2 respectively. The same applies to pharmaceutical agents, substances and compositions which include polynucleotides encoding any of these peptides (i.e., the polynucleotides of this invention).

Cancers or tumors to be treated by the pharmaceutical agents, substances or compositions of the present invention are not limited and include all kinds of cancers or tumors wherein TMEM22 is involved (e.g., is overexpressed), including, but not limited to, AML, bladder cancer, CCC, esophagus cancer, lymphoma, prostate cancer, RCC and SCLC.

The present pharmaceutical agents, substances or compositions can contain in addition to the aforementioned active ingredients, other peptides which have the ability to induce CTLs against cancerous cells, other polynucleotides encoding the other peptides, other cells that present the other peptides, or such. Herein, the other peptides that have the ability to induce CTLs against cancerous cells are exemplified by cancer specific antigens (e.g., identified TAAs), but are not limited thereto.

If needed, the pharmaceutical agents, substances or compositions of the present invention can optionally include other therapeutic substances as an active ingredient, so long as the substance does not inhibit the antitumoral effect of the active ingredient, e.g., any of the present peptides. For example, formulations can include anti-inflammatory agents, pain killers, chemotherapeutics, and the like. In addition to including other therapeutic substances in the medicament itself, the medicaments of the present invention can also be administered sequentially or concurrently with the one or more other pharmacologic agents. The amounts of medicament and pharmacologic agent depend, for example, on what type of pharmacologic agent(s) is/are used, the disease being treated, and the scheduling and routes of administration.

It should be understood that in addition to the ingredients particularly mentioned herein, the pharmaceutical agents, substances or compositions of this invention can include other agents conventional in the art having regard to the type of formulation in question.

In one embodiment of the present invention, the present pharmaceutical agents, substances or compositions can be included in articles of manufacture and kits containing materials useful for treating the pathological conditions of the disease to be treated, e.g., cancer. The article of manufacture can include a container of any of the present pharmaceutical agents, substances or compositions with a label. Suitable containers include bottles, vials, and test tubes. The containers can be formed from a variety of materials, such as glass or plastic. The label on the container should indicate the agent is used for treating or prevention of one or more conditions of the disease. The label can also indicate directions for administration and so on.

In addition to the container described above, a kit including a pharmaceutical agent, substance or composition of the present invention can optionally further include a second container housing a pharmaceutically-acceptable diluent. It can further include other materials desirable from a commercial and user standpoint, including other buffers, diluents, filters, needles, syringes, and package inserts with instructions for use.

The pharmaceutical agents, substances or compositions can, if desired, be presented in a pack or dispenser device which can contain one or more unit dosage forms containing the active ingredient. The pack can, for example, include metal or plastic foil, such as a blister pack. The pack or dispenser device can be accompanied by instructions for administration.

(1) Pharmaceutical Agents, Substances or Compositions Containing the Peptides as the Active Ingredient The peptides of this invention can be administered directly as a pharmaceutical agent, substances or composition, or if necessary, may be formulated by conventional formulation methods. In the latter case, in addition to the peptides of this invention, carriers, excipients, and such that are ordinarily used for drugs can be included as appropriate without particular limitations. Examples of such carriers are sterilized water, physiological saline, phosphate buffer, culture fluid and such. Furthermore, the pharmaceutical agents, substances or compositions can contain as necessary, stabilizers, suspensions, preservatives, surfactants and such. The pharmaceutical agents, substances or compositions of this invention can be used for anticancer purposes.

The peptides of this invention can be prepared as a combination composed of two or more of the peptides of the present invention, to induce CTLs in vivo. The peptide combination can take the form of a cocktail or can be conjugated to each other using standard techniques. For example, the peptides can be chemically linked or expressed as a single fusion polypeptide sequence. The peptides in the combination can be the same or different. By administering the peptides of this invention, the peptides are presented at a high density by the HLA antigens on APCs, then CTLs that specifically react toward the complex formed between the displayed peptide and the HLA antigen are induced. Alternatively, APCs that present any of the peptides of this invention on their cell surface, which may be obtained by stimulating APCs (e.g., DCs) derived from a subject with the peptides of this invention may be administered to the subjects, and as a result, CTLs are induced in the subject and aggressiveness towards the cancer cells can be increased.

The pharmaceutical agents, substances or compositions for the treatment and/or prevention of cancer or tumor, which include a peptide of this invention as the active ingredient, can also include an adjuvant known to effectively induce cellular immunity. Alternatively, the pharmaceutical agents, substances or compositions can be administered with other active ingredients or administered by formulation into granules. An adjuvant refers to a compound that enhances the immune response against the protein when administered together (or successively) with the protein having immunological activity. Adjuvants contemplated herein include those described in the literature (Clin Microbiol Rev 1994, 7: 277-89). Example of suitable adjuvants include aluminum phosphate, aluminum hydroxide, alum, cholera toxin, *salmonella* toxin, and such, but are not limited thereto.

Furthermore, liposome formulations, granular formulations in which the peptide is bound to few-micrometers diameter beads, and formulations in which a lipid is bound to the peptide may be conveniently used.

In another embodiment of the present invention, the peptides of the present invention may also be administered in the form of a pharmaceutically acceptable salt. Preferable examples of the salts include salts with an alkali metal, salts with a metal, salts with an organic base, salts with an organic acid and salts with an inorganic acid. As used herein, "pharmaceutically acceptable salt" refers to those salts which retain the biological effectiveness and properties of the compound and which are obtained by reaction with inorganic acids or bases such as hydrochloric acid, hydrobromic acid, sulfuric acid, nitric acid, phosphoric acid, methanesulfonic acid, ethanesulfonic acid, p-toluenesulfonic acid, salicylic acid and the like. Examples of preferred salts include salts with an alkali metal, salts with a metal, salts with an organic base, salts with an organic acid and salts with an inorganic acid.

In some embodiments, the pharmaceutical agents, substances or compositions of the present invention may further include a component which primes CTLs. Lipids have been identified as agents capable of priming CTLs in vivo against viral antigens. For example, palmitic acid residues can be attached to the epsilon- and alpha-amino groups of a lysine residue and then linked to a peptide of the present invention. The lipidated peptide can then be administered either directly in a micelle or particle, incorporated into a liposome, or emulsified in an adjuvant. As another example of lipid priming of CTL responses, E. coli lipoproteins, such as tripalmitoyl-S-glycerylcysteinyl-seryl-serine (P3CSS) can be used to prime CTL when covalently attached to an appropriate peptide (see, e.g., Deres et al., Nature 1989, 342: 561-4).

The method of administration can be oral, intradermal, subcutaneous, intravenous injection, or such, and systemic administration or local administration to the vicinity of the targeted sites. The administration can be performed by single administration or boosted by multiple administrations. The dose of the peptides of this invention can be adjusted appropriately according to the disease to be treated, age of the patient, weight, method of administration, and such, and is ordinarily 0.001 mg to 1000 mg, for example, 0.1 mg to 10 mg, and can be administered once in a few days to few months. One skilled in the art can appropriately select a suitable dose.

(2) Pharmaceutical Agents, Substances or Compositions Containing Polynucleotides as the Active Ingredient The pharmaceutical agents, substances or compositions of the present invention can also contain nucleic acids encoding the peptides disclosed herein in an expressible form. Herein, the phrase "in an expressible form" means that the polynucleotide, when introduced into a cell, will be expressed in vivo as a polypeptide that induces anti-tumor immunity. In an exemplified embodiment, the nucleic acid sequence of the polynucleotide of interest includes regulatory elements necessary for expression of the polynucleotide. The polynucleotide(s) can be equipped so to achieve stable insertion into the genome of the target cell (see, e.g., Thomas K R & Capecchi M R, Cell 1987, 51: 503-12 for a description of homologous recombination cassette vectors). See, e.g., Wolff et al., Science 1990, 247: 1465-8; U.S. Pat. Nos. 5,580,859; 5,589,466; 5,804,566; 5,739,118; 5,736,524; 5,679,647; and WO 98/04720. Examples of DNA-based delivery technologies include "naked DNA", facilitated (bupivacaine, polymers, peptide-mediated) delivery, cationic lipid complexes, and particle-mediated ("gene gun") or pressure-mediated delivery (see, e.g., U.S. Pat. No. 5,922,687).

The peptides of the invention can also be expressed by viral or bacterial vectors. Examples of expression vectors include attenuated viral hosts, such as vaccinia or fowlpox. This approach involves the use of vaccinia virus, e.g., as a vector to express nucleotide sequences that encode the peptide. Upon introduction into a host, the recombinant vaccinia virus expresses the immunogenic peptide, and thereby elicits an immune response. Vaccinia vectors and methods useful in immunization protocols are described in, e.g., U.S. Pat. No. 4,722,848. Another vector is BCG (Bacille Calmette Guerin). BCG vectors are described in Stover et al., Nature 1991, 351: 456-60. A wide variety of other vectors useful for therapeutic administration or immunization e.g., adeno and adeno-associated virus vectors, retroviral vectors, Salmonella typhi vectors, detoxified anthrax toxin vectors, and the like, will be apparent. See, e.g., Shata et al., Mol Med Today 2000, 6: 66-71; Shedlock et al., J Leukoc Biol 2000, 68: 793-806; Hipp et al., In Vivo 2000, 14: 571-85.

Delivery of a polynucleotide into a subject can be either direct, in which case the subject is directly exposed to a polynucleotide-carrying vector, or indirect, in which case, cells are first transformed with the polynucleotide of interest in vitro, then the cells are transplanted into the subject. Theses two approaches are known, respectively, as in vivo and ex vivo gene therapies.

For general reviews of the methods of gene therapy, see Goldspiel et al., Clinical Pharmacy 1993, 12: 488-505; Wu and Wu, Biotherapy 1991, 3: 87-95; Tolstoshev, Ann Rev Pharmacol Toxicol 1993, 33: 573-96; Mulligan, Science 1993, 260: 926-32; Morgan & Anderson, Ann Rev Biochem 1993, 62: 191-217; Trends in Biotechnology 1993, 11(5): 155-215). Methods commonly known in the art of recombinant DNA technology which can also be used for the present invention are described in eds. Ausubel et al., Current Protocols in Molecular Biology, John Wiley & Sons, NY, 1993; and Krieger, Gene Transfer and Expression, A Laboratory Manual, Stockton Press, NY, 1990.

The method of administration can be oral, intradermal, subcutaneous, intravenous injection, or such, and systemic administration or local administration to the vicinity of the targeted sites finds use. The administration can be performed by single administration or boosted by multiple administrations. The dose of the polynucleotide in the suitable carrier or cells transformed with the polynucleotide encoding the peptides of this invention can be adjusted appropriately according to the disease to be treated, age of the patient, weight, method of administration, and such, and is ordinarily 0.001 mg to 1000 mg, for example, 0.001 mg to 1000 mg, for example, 0.1 mg to 10 mg, and can be administered once every a few days to once every few months. One skilled in the art can appropriately select the suitable dose.

X. Methods Using the Peptides, Exosomes, APCs and CTLs

The peptides and polynucleotides of the present invention can be used for inducing APCs and CTLs. The exosomes and APCs of the present invention can be also used for inducing CTLs. The peptides, polynucleotides, exosomes and APCs can be used in combination with any other compounds, so long as the additional compounds do not inhibit CTL inducibility. Thus, any of the aforementioned pharmaceutical agents, substances or compositions of the present invention can be used for inducing CTLs. In addition thereto, those including the peptides and polynucleotides can be also used for inducing APCs as discussed explained below.

(1) Method of Inducing Antigen-presenting Cells (APCs)

The present invention provides methods of inducing APCs with high CTL inducibility using the peptides or polynucleotides of this invention.

The methods of the present invention include the step of contacting APCs with the peptides of this invention in vitro, ex vivo or in vivo. For example, the method contacting APCs with the peptides ex vivo can include the steps of:

a: collecting APCs from a subject, and
b: contacting the APCs of step a with the peptide.

The APCs are not limited to a particular kind of cells and include DCs, Langerhans cells, macrophages, B cells, and activated T cells, which are known to present proteinaceous antigens on their cell surface so as to be recognized by lymphocytes. DCs can be preferably used due to its strongest CTL inducibility among the APCs. Any peptides of the present invention can be used as the peptide of step b by themselves or in combination with other peptides of this invention.

Alternatively, the peptides of the present invention may be administered to a subject to contact the peptides with APCs in vivo. Consequently, APCs with high CTL inducibility can be induced in the body of the subject. Thus, the present invention also contemplates a method of administering the peptides of this invention to a subject to induce APCs in vivo. It is also possible to administer polynucleotides encoding the peptides of this invention to a subject in an expressible form, so that the peptides of this invention are expressed and contacted with APCs in vivo, to consequently induce APCs with high CTL inducibility in the body of the subject. Thus, the present invention also contemplates a method of administering the polynucleotides of this invention to a subject to induce APCs in vivo. The phrase "expressible form" is defined above in section "IX. Pharmaceutical agents, substances (2) Pharmaceutical agents, substances containing polynucleotides as the active ingredient".

Furthermore, the present invention includes introducing the polynucleotide of this invention into an APC to induce APCs with CTL inducibility. For example, the method may include the steps of:

a: collecting APCs from a subject, and
b: introducing a polynucleotide encoding a peptide of this invention.

Step b can be performed as described above in section "VI. Antigen-presenting cells". Alternatively, the present invention provides a method for preparing an antigen-presenting cell (APC) which specifically induces CTL activity against TMEM22, wherein the method can include one of the following steps:

(a) contacting an APC with a peptide of the present invention in vitro, ex vivo or in vivo; and
(b) introducing a polynucleotide encoding a peptide of the present invention into an APC.

(2) Method of Inducing CTLs

The present invention also provides methods for inducing CTLs using the peptides, polynucleotides, or exosomes or APCs of this invention.

The present invention also provides methods for inducing CTLs using a polynucleotide encoding a polypeptide that is capable of forming a T cell receptor (TCR) subunit recognizing a complex of the peptides of the present invention and HLA antigens. Preferably, the methods for inducing CTLs include at least one step selected from among:

(a) contacting a CD8-positive T cell with an antigen-presenting cell and/or an exosome that presents on its surface a complex of an HLA antigen and a peptide of the preset invention; and
(b) introducing a polynucleotide encoding a polypeptide that is capable of forming a TCR subunit recognizing a complex of a peptide of the present invention and an HLA antigen into a CD8 positive cell.

When the peptides, the polynucleotides, APCs, or exosomes of the present invention are administered to a subject, CTLs are induced in the body of the subject, and the strength of the immune response targeting the cancer cells is enhanced. Thus, the present invention also contemplates a method which includes the step of administering the peptides, the polynucleotides, the APCs or exosomes of this invention to a subject to induce CTLs.

Alternatively, CTLs can be also induced by their ex vivo use. In such case, after the induction of CTLs, the activated CTLs would be returned to the subject. For example, a method of the present invention to induce CTLs can include steps of:

(a) collecting APCs from a subject;
(b) contacting the APCs of step a) with the peptide; and
(c) co-culturing the APCs of step b with CD8-positive cells.

The APCs to be co-cultured with the CD8-positive cells in above step c can also be prepared by transferring a gene that includes a polynucleotide of this invention into APCs as described above in section "VI. Antigen-presenting cells", though the present invention is not limited thereto and encompasses any APC that effectively presents on its surface a complex of an HLA antigen and a peptide of this invention.

Instead of such APCs, the exosomes that presents on its surface a complex of an HLA antigen and the peptide of this invention can be also used. Namely, the present invention also contemplates a method wherein exosomes presenting on its surface a complex of an HLA antigen and the peptide of this invention are co-cultured with CD8-positive cells. Such exosomes may be prepared by the methods described above in section "V. Exosomes".

Furthermore, CTL can be induced by introducing a gene that includes a polynucleotide encoding the TCR subunit binding to the peptide of this invention into CD8-positive cells. Such transduction can be performed as described above in section "VIII. T cell receptor (TCR)".

In addition, the present invention provides a method or process for manufacturing a pharmaceutical agent, substances or composition inducing CTLs, wherein the method includes the step of admixing or formulating the peptide of the present invention with a pharmaceutically acceptable carrier.

(3) Method of Inducing Immune Response

Moreover, the present invention provides methods for an inducing immune response against diseases related to TMEM22. Suitable disease include cancer, examples of which include, but are not limited to, AML, bladder cancer, CCC, esophagus cancer, lymphoma, prostate cancer, RCC and SCLC.

The methods include the step of administering agents or compositions containing any of the peptides of the present invention or polynucleotides encoding them. The present inventive method also contemplates the administration of exosomes or APCs presenting any of the peptides of the present invention. For details, see the item of "IX. Pharmaceutical agents, substances or compositions", particularly the part describing the use of the pharmaceutical agents, substances and compositions of the present invention as vaccines. In addition, the exosomes and APCs that can be employed for the present methods for inducing immune response are described in detail under the items of "V. Exosomes", "VI. Antigen-presenting cells (APCs)", and (1) and (2) of "X. Methods using the peptides, exosomes, APCs and CTLs", supra.

The present invention also provides a method or process for manufacturing a pharmaceutical agent, substance or composition inducing immune response, wherein the method includes the step of admixing or formulating the peptide of the present invention with a pharmaceutically acceptable carrier.

Alternatively, the method of the present invention may include the step of administrating a vaccine or a pharmaceutical composition, which contains:

(a) a peptide of the present invention;
(b) a nucleic acid encoding such a peptide as disclosed herein in an expressible form;
(c) an APC or an exosome presenting a peptide of the present invention on its surface; or
(d) a cytotoxic T cell of the present invention.

In the context of the present invention, cancer overexpressing TMEM22 can be treated with these active ingredients. Examples of such cancer include, but are not limited to, AML, bladder cancer, CCC, esophagus cancer, lymphoma, prostate cancer, RCC and SCLC. Accordingly, prior to the administration of the vaccines or pharmaceutical compositions containing the active ingredients, it is preferable to confirm whether the expression level of TMEM22 in the cancer cells or tissues to be treated is enhanced compared with normal cells of the same organ. Thus, in one embodiment, the present invention provides a method for treating cancer (over) expressing TMEM22, which method may include the steps of:

i) determining the expression level of TMEM22 in cancer cells or tissue obtained from a subject with the cancer to be treated;

ii) comparing the expression level of TMEM22 with normal control; and iii) administrating at least one component selected from among (a) to (d) described above to a subject with cancer overexpressing TMEM22 compared with normal control.

Alternatively, the present invention also provides a vaccine or pharmaceutical composition that includes at least one component selected from among (a) to (d) described above, for use in administrating to a subject having cancer overexpressing TMEM22. In other words, the present invention further provides a method for identifying a subject to be treated with a TMEM22 polypeptide of the present invention, such method including the step of determining an expression level of TMEM22 in subject-derived cancer cells or tissue, wherein an increase of the level compared to a normal control level of the gene indicates that the subject has cancer which may be treated with the TMEM22 polypeptide of the present invention. The methods of treating cancer of the present invention are described in more detail below.

Any subject-derived cell or tissue can be used for the determination of TMEM22 expression so long as it includes the objective transcription or translation product of TMEM22. Examples of suitable samples include, but are not limited to, bodily tissues and fluids, such as blood, sputum and urine. Preferably, the subject-derived cell or tissue sample contains a cell population including an epithelial cell, more preferably a cancerous epithelial cell or an epithelial cell derived from tissue suspected to be cancerous. Further, if necessary, the cell may be purified from the obtained bodily tissues and fluids, and then used as the subjected-derived sample.

In the context of the present invention, a control level determined from a biological sample that is known to be non-cancerous is referred to as a "normal control level". On the other hand, if the control level is determined from a cancerous biological sample, it is referred to as a "cancerous control level". Difference between a sample expression level and a control level can be normalized to the expression level of control nucleic acids, e.g., housekeeping genes, whose expression levels are known not to differ depending on the cancerous or non-cancerous state of the cell. Exemplary control genes include, but are not limited to, beta-actin, glyceraldehyde 3 phosphate dehydrogenase, and ribosomal protein P1.

A subject to be treated by the present method is preferably a mammal. Exemplary mammals include, but are not limited to, e.g., human, non-human primate, mouse, rat, dog, cat, horse, and cow.

According to the present invention, the expression level of TMEM22 in the cancer cells or tissues obtained from a subject is determined. The expression level can be determined at the transcription (nucleic acid) product level, using methods known in the art. For example, the mRNA of TMEM22 may be quantified using probes by hybridization methods (e.g., Northern hybridization). The detection may be carried out on a chip or an array. The use of an array is preferable for detecting the expression level of TMEM22. Those skilled in the art can prepare such probes utilizing the sequence information of TMEM22. For example, the cDNA of TMEM22 may be used as the probes. If necessary, the probes may be labeled with a suitable label, such as dyes, fluorescent substances and isotopes, and the expression level of the gene may be detected as the intensity of the hybridized labels.

Furthermore, the transcription product of TMEM22 may be quantified using primers by amplification-based detection methods (e.g., RT-PCR). Such primers can also be prepared based on the available sequence information of the gene.

Specifically, a probe or primer used for the present method hybridizes under stringent, moderately stringent, or low stringent conditions to the mRNA of TMEM22. As used herein, the phrase "stringent (hybridization) conditions" refers to conditions under which a probe or primer will hybridize to its target sequence, but not to other sequences. Stringent conditions are sequence-dependent and will be different under different circumstances. Specific hybridization of longer sequences is observed at higher temperatures than shorter sequences. Generally, the temperature of a stringent condition is selected to be about 5 degrees C. lower than the thermal melting point (Tm) for a specific sequence at a defined ionic strength and pH. The Tm is the temperature (under a defined ionic strength, pH and nucleic acid concentration) at which 50% of the probes complementary to their target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30 degrees C. for short probes or primers (e.g., 10 to 50 nucleotides) and at least about 60 degrees C. for longer probes or primers. Stringent conditions may also be achieved with the addition of destabilizing agents, such as formamide. The probes or primers may be of specific sizes. The sizes may range from at least 10 nucleotides, at least 12 nucleotides, at least 15 nucleotides, at least 20 nucleotides, at least 25 nucleotides, at least 30 nucleotides and the probes and primers may range in size from 5-10 nucleotides, 10-15 nucleotides, 15-20 nucleotides, 20-25 nucleotides and 25-30 nucleotides.

Alternatively, the translation product may be detected for the diagnosis of the present invention. For example, the quantity of TMEM22 protein (SEQ ID NO: 92) may be determined. Methods for determining the quantity of the protein as the translation product include immunoassay methods that use an antibody specifically recognizing the protein. The antibody may be monoclonal or polyclonal. Furthermore, any fragment or modification (e.g., chimeric antibody, scFv, Fab, F(ab')2, Fv, etc.) of the antibody may be used for the detection, so long as the fragment or modified antibody retains the binding ability to TMEM22 protein. Methods to prepare these kinds of antibodies for the detection of proteins are well known in the art, and any method may be employed in the present invention to prepare such antibodies and equivalents thereof.

As another method to detect the expression level of TMEM22 gene based on its translation product, the intensity of staining may be observed via immunohistochemical analysis using an antibody against TMEM22 protein. Namely, in this measurement, strong staining indicates increased presence of the protein/level and, at the same time, high expression level of TMEM22 gene.

The expression level of a target gene, e.g., including TMEM22 gene, in cancer cells can be determined to be increased if the level increases from the control level (e.g., the level in normal cells) of the corresponding the target gene by, for example, 10%, 25%, or 50%; or increases to more than 1.1 fold, more than 1.5 fold, more than 2.0 fold, more than 5.0 fold, more than 10.0 fold, or more.

The control level may be determined at the same time as the cancer cells by using a sample(s) previously collected and stored from a subject/subjects whose disease state(s) (cancerous or non-cancerous) is/are known. In addition, normal cells obtained from non-cancerous regions of an organ that has the cancer to be treated may be used as normal control. Alternatively, the control level may be determined by a statistical method based on the results obtained by analyzing previously determined expression level(s) of TMEM22 gene in samples from subjects whose disease states are known. Furthermore, the control level can be derived from a database of expression patterns from previously tested cells. Moreover, according to an aspect of the present invention, the expression level of TMEM22 gene in a biological sample may be compared to multiple control levels, determined from multiple reference samples. It is preferred to use a control level determined from a reference sample derived from a tissue type similar to that of the subject-derived biological sample. Moreover, it is preferred, to use the standard value of the expression levels of TMEM22 gene in a population with a known disease state. The standard value may be obtained by any method known in the art. For example, a range of mean+/−2 S.D. or mean+/−3 S.D. may be used as the standard value.

In the context of the present invention, a control level determined from a biological sample that is known to be non-cancerous is referred to as a "normal control level". On the other hand, if the control level is determined from a cancerous biological sample, it is referred to as a "cancerous control level".

When the expression level of TMEM22 gene is increased as compared to the normal control level or is similar/equivalent to the cancerous control level, the subject may be diagnosed with cancer to be treated.

The present invention also provides a method of (i) diagnosing whether a subject has the cancer to be treated, and/or (ii) selecting a subject for cancer treatment, which method includes the steps of:

(a) determining the expression level of TMEM22 in cancer cells or tissue(s) obtained from a subject who is suspected to have the cancer to be treated;

(b) comparing the expression level of TMEM22 with a normal control level;

(c) diagnosing the subject as having the cancer to be treated, if the expression level of TMEM22 is increased as compared to the normal control level; and (d) selecting the subject for cancer treatment, if the subject is diagnosed as having the cancer to be treated, in step (c).

Alternatively, such a method includes the steps of:

(a) determining the expression level of TMEM22 in cancer cells or tissue(s) obtained from a subject who is suspected to have the cancer to be treated;

(b) comparing the expression level of TMEM22 with a cancerous control level;

(c) diagnosing the subject as having the cancer to be treated, if the expression level of TMEM22 is similar or equivalent to the cancerous control level; and (d) selecting the subject for cancer treatment, if the subject is diagnosed as having the cancer to be treated, in step (c).

The present invention also provides a kit for determining a subject suffering from cancer which can be treated with the TMEM22 polypeptide of the present invention, which may also be useful in assessing the prognosis of cancer and/or monitoring the efficacy of a cancer therapy, particularly a cancer immunotherapy. Illustrative examples of suitable cancers include, but are not limited to, AML, bladder cancer, CCC, esophagus cancer, lymphoma, prostate cancer, RCC and SCLC. More particularly, the kit preferably includes at least one reagent for detecting the expression of the TMEM22 gene in a subject-derived cancer cell, such reagent selected from among:

(a) a reagent for detecting mRNA of the TMEM22 gene;
(b) a reagent for detecting the TMEM22 protein; and
(c) a reagent for detecting the biological activity of the TMEM22 protein.

Examples of reagents suitable for detecting mRNA of the TMEM22 gene include nucleic acids that specifically bind to or identify the TMEM22 mRNA, such as oligonucleotides that have a complementary sequence to a portion of the TMEM22 mRNA. These kinds of oligonucleotides are exemplified by primers and probes that are specific to the TMEM22 mRNA. These kinds of oligonucleotides may be prepared based on methods well known in the art. If needed, the reagent for detecting the TMEM22 mRNA may be immobilized on a solid matrix. Moreover, more than one reagent for detecting the TMEM22 mRNA may be included in the kit.

On the other hand, examples of reagents suitable for detecting the TMEM22 protein include antibodies to the TMEM22 protein. The antibody may be monoclonal or polyclonal. Furthermore, any fragment or modification (e.g., chimeric antibody, scFv, Fab, F(ab')2, Fv, etc.) of the antibody may be used as the reagent, so long as the fragment or modified antibody retains the binding ability to the TMEM22 protein. Methods to prepare these kinds of antibodies for the detection of proteins are well known in the art, and any method may be employed in the present invention to prepare such antibodies and equivalents thereof. Furthermore, the antibody may be labeled with signal generating molecules via direct linkage or an indirect labeling technique. Labels and methods for labeling antibodies and detecting the binding of antibodies to their targets are well known in the art, and any labels and methods may be employed for the present invention. Moreover, more than one reagent for detecting the TMEM22 protein may be included in the kit.

The kit may contain more than one of the aforementioned reagents. The kit can further include a solid matrix and reagent for binding a probe against a TMEM22 gene or antibody against a TMEM22 peptide, a medium and container for culturing cells, positive and negative control reagents, and a secondary antibody for detecting an antibody against a TMEM22 peptide. For example, tissue samples obtained from subjects without cancer or suffering from cancer or not may serve as useful control reagents. A kit of the present invention may further include other materials desirable from a commercial and user standpoint, including buffers, diluents, filters, needles, syringes, and package inserts (e.g., written, tape, CD-ROM, etc.) with instructions for use. These reagents and such may be retained in a container with a label. Suitable containers include bottles, vials, and test tubes. The containers may be formed from a variety of materials, such as glass or plastic.

In an embodiment of the present invention, when the reagent is a probe against the TMEM22 mRNA, the reagent may be immobilized on a solid matrix, such as a porous strip, to form at least one detection site. The measurement or detection region of the porous strip may include a plurality of sites, each containing a nucleic acid (probe). A test strip may also contain sites for negative and/or positive controls. Alternatively, control sites may be located on a strip separated from the test strip. Optionally, the different detection sites may contain different amounts of immobilized nucleic acids, i.e., a higher amount in the first detection site and lesser amounts in subsequent sites. Upon the addition of a test sample, the number of sites displaying a detectable signal provides a quantitative indication of the amount of TMEM22 mRNA present in the sample. The detection sites may be configured in any suitably detectable shape and are typically in the shape of a bar or dot spanning the width of a test strip.

The kit of the present invention may further include a positive control sample or TMEM22 standard sample. The positive control sample of the present invention may be prepared by collecting TMEM22 positive samples and then assaying their TMEM22 levels. Alternatively, a purified TMEM22 protein or polynucleotide may be added to cells that do not express TMEM22 to form the positive sample or the TMEM22 sample. In the present invention, purified TMEM22 may be a recombinant protein. The TMEM22 level of the positive control sample is, for example, more than the cut off value.

In one embodiment, the present invention further provides a diagnostic kit including, a protein or a partial protein thereof capable of specifically recognizing the antibody of the present invention or the fragment thereof.

Examples of the partial peptide of the protein of the present invention include polypeptides composed of at least 8, preferably 15, and more preferably 20 contiguous amino acids in the amino acid sequence of the protein of the present invention. Cancer can be diagnosed by detecting an antibody in a sample (e.g., blood, tissue) using a protein or a peptide (polypeptide) of the present invention. The method for preparing the protein of the present invention and peptides are as described above.

The methods for diagnosing cancer of the present invention can be performed by determining the difference between the amount of anti-TMEM22 antibody and that in the corresponding control sample as describe above. The subject is suspected to be suffering from cancer, if cells or tissues of the subject contain antibodies against the expression products (TMEM22) of the gene and the quantity of the anti-TMEM22 antibody is determined to be more than the cut off value in level compared to that in normal control.

In another embodiment, a diagnostic kit of the present invention may include the peptide of the present invention and an HLA molecule binding thereto. The method for detecting antigen specific CTLs using antigenic peptides and HLA molecules has already been established (for example, Altman J D et al., Science. 1996, 274(5284): 94-6). Thus, the complex of the peptide of the present invention and the HLA molecule can be applied to the detection method to detect tumor antigen specific CTLs, thereby enabling earlier detection, recurrence and/or metastasis of cancer. Further, it can be employed for the selection of subjects applicable with the pharmaceuticals including the peptide of the present invention as an active ingredient, or the assessment of the treatment effect of the pharmaceuticals.

Particularly, according to the known method (see, for example, Altman J D et al., Science. 1996, 274(5284): 94-6), the oligomer complex, such as tetramer, of the radiolabeled HLA molecule and the peptide of the present invention can be prepared. With using the complex, the diagnosis can be done, for example, by quantifying the antigen-peptide specific CTLs in the peripheral blood lymphocytes derived from the subject suspected to be suffering from cancer.

The present invention further provides a method or diagnostic agents for evaluating immunological response of subject by using peptide epitopes as described herein. In one embodiment of the invention, HLA restricted peptides as described herein may be used as reagents for evaluating or predicting an immune response of a subject. The immune response to be evaluated may be induced by contacting an immunogen with immunocompetent cells in vitro or in vivo. In preferred embodiments, the immuno-competent cells for evaluating an immunological response, may be selected from among peripheral blood, peripheral blood lymphocyte (PBL), and peripheral blood mononuclear cell (PBMC). Methods for collecting or isolating such immunocompetent cells are well known in the arts. In some embodiments, any substances or compositions that may result in the production of antigen specific CTLs that recognize and bind to the peptide epitope(s) may be employed as the reagent. The peptide reagents may need not to be used as the immunogen. Assay systems that are used for such an analysis include relatively recent technical developments such as tetramers, staining for intra-cellular lymphokines and interferon release assays, or ELISPOT assays. In a preferred embodiment, immunocompetent cells to be contacted with peptide reagent may be antigen presenting cells including dendritic cells.

For example, peptides of the present invention may be used in tetramer staining assays to assess peripheral blood mononuclear cells for the presence of antigen-specific CTLs following exposure to a tumor cell antigen or an immunogen. The HLA tetrameric complex may be used to directly visualize antigen specific CTLs (see, e.g., Ogg et al., Science 279: 2103-2106, 1998; and Altman et al, Science 174: 94-96, 1996) and determine the frequency of the antigen-specific CTL population in a sample of peripheral blood mononuclear cells. A tetramer reagent using a peptide of the invention may be generated as described below.

A peptide that binds to an HLA molecule is refolded in the presence of the corresponding HLA heavy chain and beta 2-microglobulin to generate a trimolecular complex. In the complex, carboxyl terminal of the heavy chain is biotinylated at a site that was previously engineered into the protein. Then, streptavidin is added to the complex to form tetramer composed of the trimolecular complex and streptavidin. By means of fluorescently labeled streptavidin, the tetramer can be used to stain antigen specific cells. The cells can then be identified, for example, by flow cytometry. Such an analysis may be used for diagnostic or prognostic purposes. Cells identified by the procedure can also be used for therapeutic purposes.

The present invention also provides reagents to evaluate immune recall responses (see, e.g., Bertoni et al, J. Clin. Invest. 100: 503-513, 1997 and Penna et al., J. Exp. Med. 174: 1565-1570, 1991) including peptides of the present invention. For example, patient PBMC samples from individuals with cancer to be treated can be analyzed for the presence of antigen-specific CTLs using specific peptides. A blood sample containing mononuclear cells can be evaluated by cultivating the PBMCs and stimulating the cells with a peptide of the invention. After an appropriate cultivation period, the expanded cell population can be analyzed, for example, for CTL activity.

The peptides may also be used as reagents to evaluate the efficacy of a vaccine. PBMCs obtained from a patient vaccinated with an immunogen may be analyzed using, for example, either of the methods described above. The patient is HLA typed, and peptide epitope reagents that recognize the allele specific molecules present in the patient are selected for the analysis. The immunogenicity of the vaccine may be indicated by the presence of epitope-specific CTLs in the PBMC sample. The peptides of the invention may also be used to make antibodies, using techniques well known in the art (see, e.g., CURRENT PROTOCOLS IN IMMUNOLOGY, Wiley/Greene, N.Y.; and Antibodies A Laboratory Manual, Harlow and Lane, Cold Spring Harbor Laboratory Press, 1989), which may find use as reagents to diagnose, detect or monitor cancer. Such antibodies may include those that recognize a peptide in the context of an HLA molecule, i.e., antibodies that bind to a peptide-MHC complex.

The peptides and compositions of the present invention have a number of additional uses, some of which are described herein For instance, the present invention provides a method for diagnosing or detecting a disorder characterized by expression of a TMEM22 immunogenic polypeptide. These methods involve determining expression of a TMEM22 HLA binding peptide, or a complex of a TMEM22 HLA binding peptide and an HLA class I molecule in a biological sample. The expression of a peptide or complex of peptide and HLA class I molecule can be determined or detected by assaying with a binding partner for the peptide or complex. In an preferred embodiment, a binding partner for the peptide or complex may be an antibody recognizes and specifically bind to the peptide. The expression of TMEM22 in a biological sample, such as a tumor biopsy, can also be tested by standard PCR amplification protocols using TMEM22 primers. An example of tumor expression is presented herein and further disclosure of exemplary conditions and primers for TMEM22 amplification can be found in WO2003/27322.

Preferably, the diagnostic methods involve contacting a biological sample isolated from a subject with an agent specific for the TMEM22 HLA binding peptide to detect the presence of the TMEM22 HLA binding peptide in the biological sample. As used herein, "contacting" means placing the biological sample in sufficient proximity to the agent and under the appropriate conditions of, e.g., concentration, temperature, time, ionic strength, to allow the specific interaction between the agent and TMEM22 HLA binding peptide that are present in the biological sample. In general, the conditions for contacting the agent with the biological sample are conditions known by those of ordinary skill in the art to facilitate a specific interaction between a molecule and its cognate (e.g., a protein and its receptor cognate, an antibody and its protein antigen cognate, a nucleic acid and its complementary sequence cognate) in a biological sample. Exemplary conditions for facilitating a specific interaction between a molecule and its cognate are described in U.S. Pat. No. 5,108,921, issued to Low et al.

The diagnostic method of the present invention can be performed in either or both of in vivo and in vitro. Accordingly, biological sample can be located in vivo or in vitro in the present invention. For example, the biological sample can be a tissue in vivo and the agent specific for the TMEM22 immunogenic polypeptide can be used to detect the presence of such molecules in the tissue. Alternatively, the biological sample can be collected or isolated in vitro (e.g., a blood sample, tumor biopsy, tissue extract). In a particularly preferred embodiment, the biological sample can be a cell-containing sample, more preferably a sample containing tumor cells collected from a subject to be diagnosed or treated.

Alternatively, the diagnosis can be done, by a method which allows direct quantification of antigen-specific T cells by staining with Fluorescein-labeled HLA multimeric complexes (e.g., Altman, J. D. et al., 1996, Science 274: 94; Altman, J. D. et al., 1993, Proc. Natl. Acad. Sci. USA 90: 10330). Staining for intracellular lymphokines, and interferon-gamma release assays or ELISPOT assays also has been provided. Multimer staining, intracellular lymphokine staining and ELISPOT assays all appear to be at least 10-fold more sensitive than more conventional assays (Murali-Krishna, K. et al., 1998, Immunity 8: 177; Lalvani, A. et al., 1997, J. Exp. Med. 186: 859; Dunbar, P. R. et al., 1998, Curr. Biol. 8: 413). Pentamers (e.g., US 2004-209295A), dextramers (e.g., WO 02/072631), and streptamers (e.g., Nature medicine 6. 631-637 (2002)) may also be used.

For instance, in some embodiments, the present invention provides a method for diagnosing or evaluating an immunological response of a subject administered at least one of TMEM22 peptides of the present invention, the method including the steps of:

(a) contacting an immunogen with immunocompetent cells under the condition suitable of induction of CTL specific to the immunogen;

(b) detecting or determining induction level of the CTL induced in step (a); and (c) correlating the immunological response of the subject with the CTL induction level.

In the present invention, the immunogen is at least one of (a) a TMEM22 peptide selected from among the amino acid sequences of SEQ ID NOs: 1 to 16, 18 to 32 and 34 to 90, peptides having such amino acid sequences, and peptides having in which such amino acid sequences have been modified with 1, 2 or more amino acid substitution(s). In the meantime, conditions suitable of induction of immunogen specific CTL are well known in the art. For example, immunocompetent cells may be cultured in vitro under the presence of immunogen(s) to induce immunogen specific CTL. In order to induce immunogen specific CTLs, any stimulating factors may be added to the cell culture. For example, IL-2 is preferable stimulating factors for the CTL induction.

In some embodiments, the step of monitoring or evaluating immunological response of a subject to be treated with peptide cancer therapy may be performed before, during and/or after the treatment. In general, during a protocol of cancer therapy, immunogenic peptides are administered repeatedly to a subject to be treated. For example, immunogenic peptides may be administered every week for 3-10 weeks. Accordingly, the immunological response of the subject can be evaluated or monitored during the cancer therapy protocol. Alternatively, the step of evaluation or monitoring of immunological response to the cancer therapy may at the completion of the therapy protocol.

According to the present invention, enhanced induction of immunogen specific CTL as compared with a control indicates that the subject to be evaluated or diagnosed immunologically responded to the immunogen(s) which have been administered. Suitable controls for evaluating the immunological response may include, for example, a CTL induction level when the immunocompetent cells are contacted with no peptide, or control peptide(s) having amino acid sequences other than any TMEM22 peptides. (e.g. random amino acid sequence).

In a preferred embodiment, the immunological response of the subject is evaluated in a sequence specific manner, by comparison with an immunological response between each immunogen administered to the subject. In particular, even when a mixture of some kinds of TMEM22 peptides is administered to the subject, immunological response might vary depending on the peptides. In that case, by comparison of the immunological response between each peptide, peptides to which the subject show higher response can be identified.

XI. Antibodies

The present invention further provides antibodies that bind to the peptide of the present invention. Preferred antibodies specifically bind to the peptide of the present invention and will not bind (or will bind weakly) to non-peptide of the present invention. Alternatively, antibodies bind to the peptide of the invention as well as the homologs thereof. Antibodies against the peptide of the invention can find use in cancer diagnostic and prognostic assays, and imaging methodologies. Similarly, such antibodies can find use in the treatment, diagnosis, and/or prognosis of other cancers, to the extent TMEM22 is also expressed or overexpressed in cancer patient. Moreover, intracellularly expressed antibodies (e.g., single chain antibodies) may find therapeutic use in treating cancers in which the expression of TMEM22 is involved, examples of which include, but are not limited to, AML, bladder cancer, CCC, esophagus cancer, lymphoma, prostate cancer, RCC and SCLC.

The present invention also provides various immunological assay for the detection and/or quantification of the TMEM22 protein (SEQ ID NO: 92) or fragments thereof polypeptides having an amino acid sequences selected from among SEQ ID NOs: 1 to 16, 18 to 32 and 34 to 90. Such assays may include one or more anti-TMEM22 antibodies capable of recognizing and binding a TMEM22 protein or fragments thereof, as appropriate. In the context of the present invention, anti-TMEM22 antibodies binding to TMEM22 polypeptide preferably recognize a polypeptide having an amino acid sequences selected from among SEQ ID NOs: 1 to 16, 18 to 32 and 34 to 90. A binding specificity of antibody can be confirmed with inhibition test. That is, when the binding between an antibody to be analyzed and full-length of TMEM22 polypeptide is inhibited under presence of any fragment polypeptides having an amino acid sequence selected from among SEQ ID NOs: 1 to 16, 18 to 32 and 34 to 90, it is shown that this antibody specifically binds to the fragment. In the context of the present invention, such immunological assays are performed within various immunological assay formats well known in the art, including but not limited to, various types of radioimmunoassays, immunochromatograph technique, enzyme-linked immunosorbent assays (ELISA), enzyme-linked immunofluorescent assays (ELIFA), and the like.

Related immunological but non-antibody assays of the invention may also include T cell immunogenicity assays (inhibitory or stimulatory) as well as MHC binding assays. In addition, immunological imaging methods capable of detecting cancers expressing TMEM22 are also provided by the invention, including, but not limited to, radioscintigraphic imaging methods using labeled antibodies of the present invention. Such assays can find clinical use in the detection, monitoring, and prognosis of TMEM22 expressing cancers, examples of which include, but are not limited to, AML, bladder cancer, CCC, esophagus cancer, lymphoma, prostate cancer, RCC and SCLC.

The present invention also provides an antibody that binds to the peptide of the invention. The antibody of the invention can be used in any form, such as monoclonal or polyclonal antibodies, and include antiserum obtained by immunizing an animal such as a rabbit with the peptide of the invention, all classes of polyclonal and monoclonal antibodies, human antibodies and humanized antibodies produced by genetic recombination.

A peptide of the invention used as an antigen to obtain an antibody may be derived from any animal species, but preferably is derived from a mammal such as a human, mouse, or rat, more preferably from a human. A human-derived peptide may be obtained from the nucleotide or amino acid sequences disclosed herein.

According to the present invention, the peptide to be used as an immunization antigen may be a complete protein or a partial peptide of the protein. A partial peptide may include, for example, the amino (N)-terminal or carboxy (C)-terminal fragment of a peptide of the present invention.

Herein, an antibody is defined as a protein that reacts with either the full length or a fragment of a TMEM22 peptide. In a preferred embodiment, an antibody of the present invention can recognize fragment peptides of TMEM22 having an amino acid sequence selected from among SEQ ID NOs: 1 to 16, 18 to 32 and 34 to 90. Methods for synthesizing oligopeptide are well known in the arts. After the synthesis, peptides may be optionally purified prior to use as immunogen. In the present invention, the oligopeptide (e.g., 9- or 10mer) may be conjugated or linked with carriers to enhance the immunogenicity. Keyhole-limpet hemocyanin (KLH) is well known as the carrier. Method for conjugating KLH and peptide are also well known in the arts.

Alternatively, a gene encoding a peptide of the invention or fragment thereof may be inserted into a known expression vector, which is then used to transform a host cell as described herein. The desired peptide or fragment thereof may be recovered from the outside or inside of host cells by any standard method, and may subsequently be used as an antigen. Alternatively, whole cells expressing the peptide or their lysates or a chemically synthesized peptide may be used as the antigen.

Any mammalian animal may be immunized with the antigen, but preferably the compatibility with parental cells used for cell fusion is taken into account. In general, animals of Rodentia, Lagomorpha or Primate family may be used. Animals of the family Rodentia include, for example, mouse, rat and hamster. Animals of the family Lagomorpha include, for example, rabbit. Animals of the Primate family include, for example, a monkey of Catarrhini (old world monkey) such as *Macaca fascicularis*, rhesus monkey, sacred baboon and chimpanzees.

Methods for immunizing animals with antigens are known in the art. Intraperitoneal injection or subcutaneous injection of antigens is a standard method for the immunization of mammals. More specifically, antigens may be diluted and suspended in an appropriate amount of phosphate buffered saline (PBS), physiological saline, etc. If desired, the antigen suspension may be mixed with an appropriate amount of a standard adjuvant, such as Freund's complete adjuvant, made into emulsion and then administered to mammalian animals. Preferably, it is followed by several administrations of antigen mixed with an appropriately amount of Freund's incomplete adjuvant every 4 to 21 days. An appropriate carrier may also be used for immunization. After immunization as above, serum may be examined by a standard method for an increase in the amount of desired antibodies.

Polyclonal antibodies against the peptides of the present invention may be prepared by collecting blood from the immunized mammal examined for the increase of desired antibodies in the serum, and by separating serum from the blood by any conventional method. Polyclonal antibodies may include serum containing the polyclonal antibodies, as well as the fraction containing the polyclonal antibodies may be isolated from the serum. Immunoglobulin G or M can be prepared from a fraction which recognizes only the peptide of the present invention using, for example, an affinity column coupled with the peptide of the present invention, and further purifying this fraction using protein A or protein G column.

To prepare monoclonal antibodies, immune cells are collected from the mammal immunized with the antigen and checked for the increased level of desired antibodies in the serum as described above, and are subjected to cell fusion. The immune cells used for cell fusion may preferably be obtained from spleen. Other preferred parental cells to be fused with the above immunocyte include, for example, myeloma cells of mammalians, and more preferably myeloma cells having an acquired property for the selection of fused cells by drugs.

The above immunocyte and myeloma cells can be fused according to known methods, for example, the method of Milstein et al. (Galfre and Milstein, Methods Enzymol 73: 3-46 (1981)).

Resulting hybridomas obtained by the cell fusion may be selected by cultivating them in a standard selection medium, such as HAT medium (hypoxanthine, aminopterin and thymidine containing medium). The cell culture is typically continued in the HAT medium for several days to several weeks, the time being sufficient to allow all the other cells, with the exception of the desired hybridoma (non-fused cells), to die. Then, the standard limiting dilution may be performed to screen and clone a hybridoma cell producing the desired antibody.

In addition to the above method, in which a non-human animal is immunized with an antigen for preparing hybridoma, human lymphocytes such as those infected by EB virus may be immunized with a peptide, peptide expressing cells or their lysates in vitro. Then, the immunized lymphocytes are fused with human-derived myeloma cells that are capable of indefinitely dividing, such as U266, to yield a hybridoma producing a desired human antibody that is able to bind to the peptide can be obtained (Unexamined Published Japanese Patent Application No. Sho 63-17688).

The obtained hybridomas are subsequently transplanted into the abdominal cavity of a mouse and the ascites are extracted. The obtained monoclonal antibodies can be purified by, for example, ammonium sulfate precipitation, a protein A or protein G column, DEAE ion exchange chromatography or an affinity column to which the peptide of the present invention is coupled. The antibody of the present invention can be used not only for purification and detection of the peptide of the present invention, but also as a candidate for agonists and antagonists of the peptide of the present invention.

Alternatively, an immune cell, such as an immunized lymphocyte, producing antibodies may be immortalized by an oncogene and used for preparing monoclonal antibodies.

Monoclonal antibodies thus obtained can be also recombinantly prepared using genetic engineering techniques (see, for example, Borrebaeck and Larrick, Therapeutic Monoclonal Antibodies, published in the United Kingdom by MacMillan Publishers LTD (1990)). For example, a DNA encoding an antibody may be cloned from an immune cell, such as a hybridoma or an immunized lymphocyte producing the antibody, inserted into an appropriate vector, and introduced into host cells to prepare a recombinant antibody. The present invention also provides recombinant antibodies prepared as described above.

Furthermore, an antibody of the present invention may be a fragment of an antibody or modified antibody, so long as it binds to one or more of the peptides of the invention. For instance, the antibody fragment may be Fab, F(ab')$_2$, Fv or single chain Fv (scFv), in which Fv fragments from H and L chains are ligated by an appropriate linker (Huston et al., Proc Natl Acad Sci USA 85: 5879-83 (1988)). More specifically, an antibody fragment may be generated by treating an antibody with an enzyme, such as papain or pepsin. Alternatively, a gene encoding the antibody fragment may be constructed, inserted into an expression vector and expressed in an appropriate host cell (see, for example, Co et al., J Immunol 152: 2968-76 (1994); Better and Horwitz, Methods Enzymol 178: 476-96 (1989); Pluckthun and Skerra, Methods Enzymol 178: 497-515 (1989); Lamoyi, Methods Enzymol 121: 652-63 (1986); Rousseaux et al., Methods Enzymol 121: 663-9 (1986); Bird and Walker, Trends Biotechnol 9: 132-7 (1991)).

An antibody may be modified by conjugation with a variety of molecules, such as polyethylene glycol (PEG). The present invention provides for such modified antibodies. The modified antibody can be obtained by chemically modifying an antibody. These modification methods are conventional in the field.

Alternatively, an antibody of the present invention may be obtained as a chimeric antibody, between a variable region derived from nonhuman antibody and the constant region derived from human antibody, or as a humanized antibody, including the complementarity determining region (CDR) derived from nonhuman antibody, the frame work region (FR) and the constant region derived from human antibody. Such antibodies can be prepared according to known technology. Humanization can be performed by substituting rodent CDRs or CDR sequences for the corresponding sequences of a human antibody (see, e.g., Verhoeyen et al., Science 239: 1534-1536 (1988)). Accordingly, such humanized antibodies are chimeric antibodies, wherein substantially less than an intact human variable domain has been substituted by the corresponding sequence from a non-human species.

Fully human antibodies including human variable regions in addition to human framework and constant regions can also be used. Such antibodies can be produced using various techniques known in the art. For example, in vitro methods involve use of recombinant libraries of human antibody fragments displayed on bacteriophage (e.g., Hoogenboom & Winter, J. Mol. Biol. 227:381 (1991). Similarly, human antibodies can be made by introducing of human immunoglobulin loci into transgenic animals, e.g., mice in which the endogenous immunoglobulin genes have been partially or completely inactivated. This approach is described, e.g., in U.S. Pat. Nos. 6,150,584, 5,545,807; 5,545,806; 5,569,825; 5,625,126; 5,633,425; 5,661,016.

Antibodies obtained as above may be purified to homogeneity. For example, the separation and purification of the antibody can be performed according to the separation and purification methods used for general proteins. For example, the antibody may be separated and isolated by the appropriately selected and combined use of column chromatographies, such as affinity chromatography, filter, ultrafiltration, salting-out, dialysis, SDS polyacrylamide gel electrophoresis and isoelectric focusing (Antibodies: A Laboratory Manual. Ed Harlow and David Lane, Cold Spring Harbor Laboratory (1988)), but are not limited thereto. A protein A column and protein G column can be used as the affinity column. Exemplary protein A columns to be used include, for example, Hyper D, POROS and Sepharose F.F. (Pharmacia).

Exemplary chromatography, with the exception of affinity includes, for example, ion-exchange chromatography, hydrophobic chromatography, gel filtration, reverse phase chromatography, adsorption chromatography and the like (Strategies for Protein Purification and Characterization: A Laboratory Course Manual. Ed Daniel R. Marshak et al., Cold Spring Harbor Laboratory Press (1996)). The chromatographic procedures can be carried out by liquid-phase chromatography, such as HPLC and FPLC.

For example, measurement of absorbance, enzyme-linked immunosorbent assay (ELISA), enzyme immunoassay (EIA), radioimmunoassay (RIA) and/or immunofluorescence may be used to measure the antigen binding activity of the antibody of the invention. In ELISA, the antibody of the present invention is immobilized on a plate, a peptide of the invention is applied to the plate, and then a sample containing a desired antibody, such as culture supernatant of antibody producing cells or purified antibodies, is applied. Then, a secondary antibody that recognizes the primary antibody and is labeled with an enzyme, such as alkaline phosphatase, is applied, and the plate is incubated. Next, after washing, an enzyme substrate, such as p-nitrophenyl phosphate, is added to the plate, and the absorbance is measured to evaluate the antigen binding activity of the sample. A fragment of the peptide, such as a C-terminal or N-terminal fragment, may be used as the antigen to evaluate the binding activity of the antibody. BIAcore (Pharmacia) may be used to evaluate the activity of the antibody according to the present invention.

The above methods allow for the detection or measurement of a peptide of the invention, by exposing an antibody of the invention to a sample presumed to contain a peptide of the invention, and detecting or measuring the immune complex formed by the antibody and the peptide.

Because the method of detection or measurement of the peptide according to the invention can specifically detect or measure a peptide, the method can find use in a variety of experiments in which the peptide is used.

XII. Vectors and Host Cells

The present invention also provides a vector and host cell into which a nucleotide encoding the peptide of the present invention is introduced. A vector of the present invention can find use to keep a nucleotide, especially a DNA, of the present invention in host cell, to express the peptide of the present invention, or to administer the nucleotide of the present invention for gene therapy.

When *E. coli* is a host cell and the vector is amplified and produced in a large amount in *E. coli* (e.g., JM109, DH5 alpha, HB101 or XL1Blue), the vector should have "ori" to be amplified in *E. coli* and a marker gene for selecting transformed *E. coli* (e.g., a drug-resistance gene selected by a drug such as ampicillin, tetracycline, kanamycin, chloramphenicol or the like). For example, M13-series vectors, pUC-series vectors, pBR322, pBluescript, pCR-Script, etc., can be used. In addition, pGEM-T, pDIRECT and pT7 can also be used for subcloning and extracting cDNA as well as the vectors described above. When a vector is used to produce the protein of the present invention, an expression vector can find use.

For example, an expression vector to be expressed in *E. coli* should have the above characteristics to be amplified in *E. coli*. When *E. coli*, such as JM109, DH5 alpha, HB101 or XL1 Blue, are used as a host cell, the vector should have a promoter, for example, lacZ promoter (Ward et al., Nature 341: 544-6 (1989); FASEB J 6: 2422-7 (1992)), araB promoter (Better et al., Science 240: 1041-3 (1988)), T7 promoter or the like, that can efficiently express the desired gene in *E. coli*. In that respect, pGEX-5X-1 (Pharmacia), "QIAexpress system" (Qiagen), pEGFP and pET (in this case, the host is preferably BL21 which expresses T7 RNA polymerase), for example, can be used instead of the above vectors. Additionally, the vector may also contain a signal sequence for peptide secretion. An exemplary signal sequence that directs the peptide to be secreted to the periplasm of the *E. coli* is the pelB signal sequence (Lei et al., J Bacteriol 169: 4379 (1987)). Means for introducing of the vectors into the target host cells include, for example, the calcium chloride method, and the electroporation method.

In addition to *E. coli*, for example, expression vectors derived from mammals (for example, pcDNA3 (Invitrogen) and pEGF-BOS (Nucleic Acids Res 18(17): 5322 (1990)), pEF, pCDM8), expression vectors derived from insect cells (for example, "Bac-to-BAC baculovirus expression system" (GIBCO BRL), pBacPAK8), expression vectors derived from plants (e.g., pMH1, pMH2), expression vectors derived from animal viruses (e.g., pHSV, pMV, pAdexLcw), expression vectors derived from retroviruses (e.g., pZIpneo), expression vector derived from yeast (e.g., "*Pichia* Expression Kit" (Invitrogen), pNV11, SP-Q01) and expression vectors derived from *Bacillus subtilis* (e.g., pPL608, pKTH50) can be used for producing the polypeptide of the present invention.

In order to express the vector in animal cells, such as CHO, COS or NIH3T3 cells, the vector should have a promoter necessary for expression in such cells, for example, the SV40 promoter (Mulligan et al., Nature 277: 108 (1979)), the MMLV-LTR promoter, the EF1 alpha promoter (Mizushima et al., Nucleic Acids Res 18: 5322 (1990)), the CMV promoter and the like, and preferably a marker gene for selecting transformants (for example, a drug resistance gene selected by a drug (e.g., neomycin, G418)). Examples of known vectors with these characteristics include, for example, pMAM, pDR2, pBK-RSV, pBK-CMV, pOPRSV and pOP13.

The following examples are presented to illustrate the present invention and to assist one of ordinary skill in making and using the same. The examples are not intended in any way to otherwise limit the scope of the invention.

EXAMPLES

Materials and Methods

Cell Lines

TISI, HLA-A*2402-positive B-lymphoblastoid cell line, was purchased from the IHWG Cell and Gene Bank (Seattle, Wash.). T2, HLA-A*0201-positive B-lymphoblastoid cell line, and COS7, African green monkey kidney cell line, was purchased from ATCC.

Candidate Selection of Peptides Derived from TMEM22

9-mer and 10-mer peptides derived from TMEM22 that bind to HLA-A*2402 molecule were predicted using binding prediction software "BIMAS" (www-bimas.cit.nih.gov/molbio/hla_bind) (Parker et al. (J Immunol 1994, 152(1): 163-75), Kuzushima et al. (Blood 2001, 98(6): 1872-81)) and "NetMHC 3.0" (www.cbs.dtu.dk/services/NetMHC/) (Buus et al. (Tissue Antigens., 62:378-84, 2003), Nielsen et al. (Protein Sci., 12:1007-17, 2003, Bioinformatics, 20(9):1388-97, 2004)). Additionally, 9-mer and 10-mer peptides derived from TMEM22 that bind to HLA-A*0201 molecule were predicted using "NetMHC3.0". These peptides were synthesized by Bio Synthesis Inc. (Lewisville, Tex.) according to a standard solid phase synthesis method and purified by reversed phase high performance liquid chromatography (HPLC). The purity (>90%) and the identity of the peptides were determined by analytical HPLC and mass spectrometry analysis, respectively. Peptides were dissolved in dimethyl sulfoxide (DMSO) at 20 mg/ml and stored at −80 degrees C.

In vitro CTL Induction

Monocyte-derived dendritic cells (DCs) were used as antigen-presenting cells (APCs) to induce cytotoxic T lymphocyte (CTL) responses against peptides presented on human leukocyte antigen (HLA). DCs were generated in vitro as described elsewhere (Nakahara S et al., Cancer Res 2003 Jul. 15, 63(14): 4112-8). Specifically, peripheral blood mononuclear cells (PBMCs) isolated from a normal volunteer (HLA-A*2402 positive or HLA-A*0201 positive) by Ficoll-Plaque (Pharmacia) solution were separated by adherence to a plastic tissue culture dish (Becton Dickinson) so as to enrich them as the monocyte fraction. The monocyte-enriched population was cultured in the presence of 1000 U/ml of granulocyte-macrophage colony-stimulating factor (GM-CSF) (R&D System) and 1000 U/ml of interleukin (IL)-4 (R&D System) in AIM-V Medium (Invitrogen) containing 2% heat-inactivated autologous serum (AS). After 7 days of culture, the cytokine-induced DCs were pulsed with 20 microgram/ml of each of the synthesized peptides in the presence of 3 microgram/ml of beta 2-microglobulin for 3 hrs at 37 degrees C. in AIM-V Medium.

The generated cells appeared to express DC-associated molecules, such as CD80, CD83, CD86 and HLA class II, on their cell surfaces (data not shown). These peptide-pulsed DCs were then inactivated by X-irradiation (20 Gy) and mixed at a 1:20 ratio with autologous CD8+ T cells, obtained by positive selection with CD8 Positive Isolation Kit (Dynal). These cultures were set up in 48-well plates (Corning); each well contained $1.5 \times 10^4$ peptide-pulsed DCs, $3 \times 10^5$ CD8+ T cells and 10 ng/ml of IL-7 (R&D System) in 0.5 ml of AIM-V/2% AS medium. Three days later, these cultures were supplemented with IL-2 (CHIRON) to a final concentration of 20 IU/ml. On days 7 and 14, the T cells were further stimulated with the autologous peptide-pulsed DCs.

The DCs were prepared each time by the same way described above. CTL was tested against peptide-pulsed TISI cells (A24) or T2 cells (A2) after the 3rd round of peptide stimulation on day 21 (Tanaka H et al., Br J Cancer 2001 Jan. 5, 84(1): 94-9; Umano Y et al., Br J Cancer 2001 Apr. 20, 84(8): 1052-7; Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

CTL Expansion Procedure

CTLs were expanded in culture using the method similar to the one described by Riddell et al. (Walter E A et al., N Engl J Med 1995 Oct. 19, 333(16): 1038-44; Riddell S R et al., Nat Med 1996 February, 2(2): 216-23). A total of $5 \times 10^4$ CTLs were suspended in 25 ml of AIM-V/5% AS medium with 2 kinds of human B-lymphoblastoid cell lines, inactivated by Mitomycin C, in the presence of 40 ng/ml of anti-CD3 monoclonal antibody (Pharmingen). One day after initiating the cultures, 120 IU/ml of IL-2 were added to the cultures. The cultures were fed with fresh AIM-V/5% AS medium containing 30 IU/ml of IL-2 on days 5, 8 and 11 (Tanaka H et al., Br J Cancer 2001 Jan. 5, 84(1): 94-9; Umano Y et al., Br J Cancer 2001 Apr. 20, 84(8): 1052-7; Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

Establishment of CTL Clones

The dilutions were made to have 0.3, 1, and 3 CTLs/well in 96 round-bottomed micro titer plate (Nalge Nunc International). CTLs were cultured with $1 \times 10^4$ cells/well of 2 kinds of human B-lymphoblastoid cell lines, 30 ng/ml of anti-CD3 antibody, and 125 U/ml of IL-2 in a total of 150 microlitter/well of AIM-V Medium containing 5% AS. 50 microlitter/well of IL-2 were added to the medium 10 days later so to reach a final concentration of 125 U/ml IL-2. CTL activity was tested on the 14th day, and CTL clones were expanded using the same method as described above (Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

Specific CTL Activity

To examine specific CTL activity, interferon (IFN)-gamma enzyme-linked immunospot (ELISPOT) assay and IFN-gamma enzyme-linked immunosorbent assay (ELISA) were performed. Specifically, peptide-pulsed TISI (A24) or T2 (A2) ($1 \times 10^4$/well) was prepared as stimulator cells. Cultured cells in 48 wells were used as responder cells. IFN-gamma ELISPOT assay and IFN-gamma ELISA assay were performed under manufacture procedure.

Establishment of the Cells Forcibly Expressing Either or Both of the Target Gene and HLA-A24/HLA-A02

The cDNA encoding an open reading frame of target gene, HLA-A*2402 or HLA-A*0201 was amplified by PCR. The PCR-amplified products were cloned into the expression vector. The plasmids were transfected into COS7, which is the target genes and HLA-A24/A2-negative cell line, using lipofectamine 2000 (Invitrogen) according to the manufacturer's recommended procedures. After 2 days from transfection, the transfected cells were harvested with versene (Invitrogen) and used as the target cells ($5 \times 10^4$ cells/well) for CTL activity assay.

Results 1

Enhanced TMEM22 Expression in Cancers

The global gene expression profile data obtained from various cancers using cDNA-microarray revealed that TMEM22 (GenBank Accession No. NM_025246, NM_001097599, NM_001097600; for example, SEQ ID No: 91) expression was elevated. TMEM22 expression was validly elevated in 1 out of 6 AML, 1 out of 29 bladder cancers, 1 out of 1 CCC, 6 out of 41 esophagus cancers, 1 out of 1 lymphoma, 4 out of 6 prostate cancers, 9 out of 13 RCC and 13 out of 21 SCLCs (Table 1).

TABLE 1

Ratio of cases observed up-regulation of TMEM22 in cancerous tissue as compared with normal corresponding tissue

| Cancers | Ratio |
| --- | --- |
| AML | 1/6 |
| Bladder Cancer | 1/29 |
| CCC | 1/1 |
| Esophagus Cancer | 6/41 |
| Lymphoma | 1/1 |
| Prostate Cancer | 4/6 |
| RCC | 9/13 |
| SCLC | 13/21 |

Results 2

Prediction of HLA-A24 Binding Peptides Derived from TMEM22

Tables 2a and 2b show the HLA-A24 binding 9mer and 10mer peptides of TMEM22 in the order of high binding affinity. Peptides from SEQ ID NOs: 1 to 9 and 17 to 27 were predicted by BIMAS. Peptides from SEQ ID NOs: 10 to 16 and 28 to 31 were predicted by NetMHC 3.0. A total of 31 peptides with potential HLA-A24 binding ability were selected and examined to determine the epitope peptides.

TABLE 2a

HLA-A24 binding 9mer peptides derived from TMEM22

| SEQ ID NO | Start Position | amino acid sequence | score |
| --- | --- | --- | --- |
| 1 | 390 | GYKLYWRNL | 200 |
| 2 | 274 | VYRSIKEKI | 77 |
| 3 | 372 | IYDVFGGVI | 50 |
| 4 | 331 | AFLGVYYAL | 42 |
| 5 | 385 | VFVLAGYKL | 33 |

TABLE 2a-continued

HLA-A24 binding 9mer peptides derived from TMEM22

| SEQ ID NO | Start Position | amino acid sequence | |
|---|---|---|---|
| 6 | 204 | VFSAILAFL | 28 |
| 7 | 368 | IFPSIYDVF | 21 |
| 8 | 67 | AFFGTMDTL | 20 |
| 9 | 37 | GYEEINEGY | 12.6 |
| | | | Kd (nM) |
| 10 | 297 | IWGISTMFI | 49 |
| 11 | 137 | IFIRSVFQV | 95 |
| 12 | 98 | IFQSRKMWI | 169 |
| 13 | 197 | MWRATTTVF | 184 |
| 14 | 283 | SMWTALFTF | 209 |
| 15 | 142 | VFQVLSVLV | 371 |
| 16 | 375 | VFGGVIIMI | 444 |

TABLE 2b

HLA-A24 binding 10mer peptides derived from TMEM22

| SEQ ID NO | Start Position | amino acid sequence | |
|---|---|---|---|
| | | | score |
| 17 | 8 | KYPVkKRVKI | 165 |
| 18 | 137 | IFIRsVFQVL | 60.48 |
| 19 | 140 | RSVFqVLSVL | 16.8 |
| 20 | 153 | YYQEaPFGPS | 10.8 |
| 21 | 170 | FYGVcNVISI | 50 |
| 22 | 204 | VFSAiLAFLL | 24 |
| 23 | 257 | GYTMtVMAGL | 280 |
| 24 | 319 | SYLIaICVCS | 10.5 |
| 25 | 355 | IVVAmVLQLL | 10.08 |
| 26 | 372 | IYDVfGGVII | 50 |
| 27 | 402 | DYQEiLDSPI | 108 |
| | | | Kd (nM) |
| 28 | 282 | ISMWTALFTF | 83 |
| 29 | 297 | IWGISTMFIL | 149 |
| 30 | 104 | MWIVLFGSAL | 323 |
| 31 | 177 | ISITCAYTSF | 426 |

Start position indicates the number of amino acid residue from the N-terminus of TMEM22.
Binding score is derived from "BIMAS".
Dissociation constant [Kd (nM)] is derived from "NetMHC3.0".

CTL Induction with the Predicted Peptides from TMEM22 Restricted with HLA-A*2402 and Establishment for CTL Lines Stimulated with TMEM22 Derived Peptides CTLs for those peptides derived from TMEM22 were generated according to the protocols as described in "Materials and Methods". Peptide specific CTL activity was determined by IFN-gamma ELISPOT assay (FIGS. 1a-n). The following well numbers demonstrated potent IFN-gamma production as compared to the control wells: well number #4 stimulated with TMEM22-A24-9-390 (SEQ ID NO: 1) (a), #7 with TMEM22-A24-9-274 (SEQ ID NO: 2) (b), #3 and #5 with TMEM22-A24-9-372 (SEQ ID NO: 3) (c), #8 with TMEM22-A24-9-331 (SEQ ID NO: 4) (d), #4, #6 and #7 with TMEM22-A24-9-385 (SEQ ID NO: 5) (e), #3, #4 and #5 with TMEM22-A24-9-204 (SEQ ID NO: 6) (f), #3, #6 and #8 with TMEM22-A24-9-297 (SEQ ID NO: 10) (g), #3 with TMEM22-A24-9-98 (SEQ ID NO: 12) (h), #2 and #4 with TMEM22-A24-9-375 (SEQ ID NO: 16) (i), #5 with TMEM22-A24-10-137 (SEQ ID NO: 18) (j), #1 with TMEM22-A24-10-140 (SEQ ID NO: 19) (k), #2, #3 and #4 with TMEM22-A24-10-204 (SEQ ID NO: 22) (l), #1, #6, and #8 with TMEM22-A24-10-282 (SEQ ID NO: 28) (m) and #7 with TMEM22-A24-10-177 (SEQ ID NO: 31) (n). On the other hand, no potent IFN-gamma production could be detected by stimulation with other peptides shown in Table 2, despite those peptides had possible binding activity with HLA-A*2402. For example, as is typical of negative data, specific IFN-gamma production was not observed from the CTL stimulated with TMEM22-A24-10-8 (SEQ ID NO: 17) (FIG. 1(o)). The results indicate that 14 peptides derived from TMEM22 were screened as the peptides that could induce potent CTLs.

Establishment of CTL Lines and Clones Against TMEM22 Specific Peptides

Figure 2:
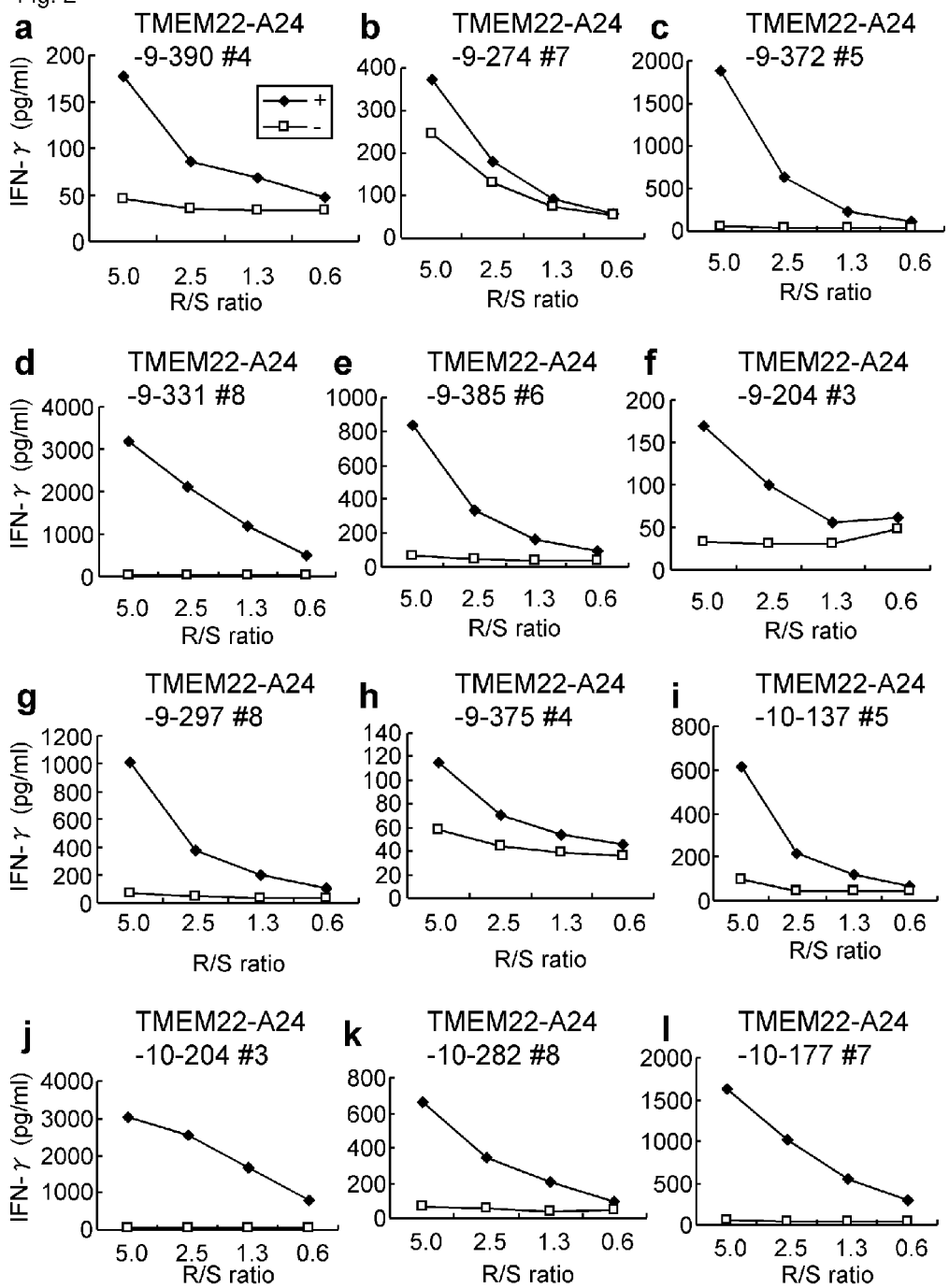
FIG. 2 depicts line graphs showing the IFN-gamma production of CTL lines stimulated with TMEM22-A24-9-390 (SEQ ID NO: 1) (a), TMEM22-A24-9-274 (SEQ ID NO: 2 (b), TMEM22-A24-9-372 (SEQ ID NO: 3) (c), TMEM22-A24-9-331 (SEQ ID NO: 4) (d) TMEM22-A24-9-385 (SEQ ID NO: 5) (e), TMEM22-A24-9-204 (SEQ ID NO: 6) (f), TMEM22-A24-9-297 (SEQ ID NO: 10) (g), TMEM22-A24-9-375 (SEQ ID NO: 16) (h), TMEM22-A24-10-137 (SEQ ID NO: 18) (i), TMEM22-A24-10-204 (SEQ ID NO: 22) (j) TMEM22-A24-10-282 (SEQ ID NO: 28) (k) and TMEM22-A24-10-177 (SEQ ID NO: 31) (l) detected by IFN-gamma ELISA assay. The results demonstrate that CTL lines established by stimulation with each peptide showed potent IFN-gamma production as compared with the control. In the figures, "+" indicates the IFN-gamma production against target cells pulsed with the appropriate peptide and "−" indicates the IFN-gamma production against target cells not pulsed with any peptides.

The cells that showed peptide specific CTL activity detected by IFN-gamma ELISPOT assay in the well number #4 with TMEM22-A24-9-390 (SEQ ID NO: 1), #7 with TMEM22-A24-9-274 (SEQ ID NO: 2), #5 with TMEM22-A24-9-372 (SEQ ID NO: 3), #8 with TMEM22-A24-9-331 (SEQ ID NO: 4), #6 with TMEM22-A24-9-385 (SEQ ID NO: 5), #3 with TMEM22-A24-9-204 (SEQ ID NO: 6), #8 with TMEM22-A24-9-297 (SEQ ID NO: 10), #4 with TMEM22-A24-9-375 (SEQ ID NO: 16), #5 with TMEM22-A24-10-137 (SEQ ID NO: 18), #3 with TMEM22-A24-10-204 (SEQ ID NO: 22), #8 with TMEM22-A24-10-282 (SEQ ID NO: 28) and #7 with TMEM22-A24-10-177 (SEQ ID NO: 31) were expanded and CTL lines were established by limiting dilution as described in the "Materials and Methods" section above. CTL activity of those CTL lines was determined by IFN-gamma ELISA assay (FIGS. 2a-1). All CTL lines demonstrated potent IFN-gamma production against the target cells pulsed with corresponding peptide as compared to target cells without peptide pulse. Furthermore, CTL clones were established by limiting dilution from CTL lines, and IFN-gamma production from CTL clones against target cells pulsed peptide were determined by IFN-gamma ELISA assay. Potent IFN-gamma productions were determined from CTL clones stimulated with TMEM22-A24-9-331 (SEQ ID NO: 4), TMEM22-A24-9-204 (SEQ ID NO: 6), TMEM22-A24-9-297 (SEQ ID NO: 10) and TMEM22-A24-10-204 (SEQ ID NO: 22) in FIGS. 3a-d.

Specific CTL Activity Against Target Cells Expressing TMEM22 and HLA-A*2402

The established CTL lines raised against these peptides were examined for their ability to recognize target cells that express TMEM22 and HLA-A*2402 gene. Specific CTL activity against COS7 cells which transfected with both the full length of TMEM22 and HLA-A*2402 gene (a specific model for the target cells that express TMEM22 and HLA-A*2402 gene) was tested using the CTL lines raised by corresponding peptide. COS7 cells transfected with either full length of TMEM22 gene or HLA-A* 2402 were prepared as controls. In FIG. 4, the CTLs stimulated with TMEM22-A24-9-385 (SEQ ID NO: 5) showed potent CTL activity against COS7 cells expressing both TMEM22 and HLA-A*2402. On the other hand, no significant specific CTL activity was detected against the controls. Thus, these data clearly demonstrated that peptide of TMEM22-A24-9-385 (SEQ ID NO: 5) was endogenously processed and presented on the target cells with HLA-A*2402 molecule and were recognized by the CTLs. These results indicate that this peptide derived from TMEM22 may be suitable as a cancer vaccine for patients with TMEM22 expressing tumors.

Homology Analysis of Antigen Peptides

The CTLs stimulated with TMEM22-A24-9-390 (SEQ ID NO: 1), TMEM22-A24-9-274 (SEQ ID NO: 2), TMEM22-A24-9-372 (SEQ ID NO: 3), TMEM22-A24-9-331 (SEQ ID NO: 4), TMEM22-A24-9-385 (SEQ ID NO: 5), TMEM22-A24-9-204 (SEQ ID NO: 6), TMEM22-A24-9-297 (SEQ ID NO: 10), TMEM22-A24-9-98 (SEQ ID NO: 12), TMEM22-A24-9-375 (SEQ ID NO: 16), TMEM22-A24-10-137 (SEQ ID NO: 18), TMEM22-A24-10-140 (SEQ ID NO: 19), TMEM22-A24-10-204 (SEQ ID NO: 22), TMEM22-A24-10-282 (SEQ ID NO: 28) and TMEM22-A24-10-177 (SEQ ID NO: 31) showed significant and specific CTL activity. This result may be due to the fact that the sequences of TMEM22-A24-9-390 (SEQ ID NO: 1), TMEM22-A24-9-274 (SEQ ID NO: 2), TMEM22-A24-9-372 (SEQ ID NO: 3), TMEM22-A24-9-331 (SEQ ID NO: 4), TMEM22-A24-9-385 (SEQ ID NO: 5), TMEM22-A24-9-204 (SEQ ID NO: 6), TMEM22-A24-9-297 (SEQ ID NO: 10), TMEM22-A24-9-98 (SEQ ID NO: 12), TMEM22-A24-9-375 (SEQ ID NO: 16), TMEM22-A24-10-137 (SEQ ID NO: 18), TMEM22-A24-10-140 (SEQ ID NO: 19), TMEM22-A24-10-204 (SEQ ID NO: 22), TMEM22-A24-10-282 (SEQ ID NO: 28) and TMEM22-A24-10-177 (SEQ ID NO: 31) are homologous to peptides derived from other molecules that are known to sensitize the human immune system. To exclude this possibility, homology analyses were performed for these peptide sequences using as queries the BLAST algorithm (http://www.ncbi.nlm.nih.gov/blast/blast.cgi) which revealed no sequence with significant homology. The results of homology analyses indicate that the sequences of TMEM22-A24-9-390 (SEQ ID NO: 1), TMEM22-A24-9-274 (SEQ ID NO: 2), TMEM22-A24-9-372 (SEQ ID NO: 3), TMEM22-A24-9-331 (SEQ ID NO: 4), TMEM22-A24-9-385 (SEQ ID NO: 5), TMEM22-A24-9-204 (SEQ ID NO: 6), TMEM22-A24-9-297 (SEQ ID NO: 10), TMEM22-A24-9-98 (SEQ ID NO: 12), TMEM22-A24-9-375 (SEQ ID NO: 16), TMEM22-A24-10-137 (SEQ ID NO: 18), TMEM22-A24-10-140 (SEQ ID NO: 19), TMEM22-A24-10-204 (SEQ ID NO: 22), TMEM22-A24-10-282 (SEQ ID NO: 28) and TMEM22-A24-10-177 (SEQ ID NO: 31) are unique and thus, there is little possibility, to our best knowledge, that these molecules raise unintended immunologic response to some unrelated molecule.

In conclusion, novel HLA-A24 epitope peptides derived from TMEM22 were identified. Furthermore, the results herein demonstrate that epitope peptide of TMEM22 may be suitable for use in cancer immunotherapy.

Results 3

Prediction of HLA-A02 Binding Peptides Derived from TMEM22

Tables 3a and 3b show the HLA-A02 binding 9mer and 10mer peptides of TMEM22 in the order of high binding affinity. A total of 59 peptides with potential HLA-A02 binding ability were selected and examined to determine the epitope peptides.

TABLE 3a

HLA-A02 binding 9mer peptides derived from TMEM22

| SEQ ID NO | Start Position | amino acid sequence | Kd (nM) |
|---|---|---|---|
| 32 | 196 | TMWRATTTV | 12 |
| 33 | 305 | ILQEPIIPL | 14 |
| 34 | 262 | VMAGLTTAL | 27 |
| 35 | 338 | ALDKFHPAL | 32 |
| 36 | 213 | LVDEKMAYV | 36 |
| 37 | 379 | VIIMISVFV | 49 |
| 38 | 381 | IMISVFVLA | 54 |
| 39 | 364 | LVLHIFPSI | 56 |
| 40 | 320 | YLIAICVCS | 61 |
| 41 | 367 | HIFPSIYDV | 66 |
| 42 | 99 | FQSRKMWIV | 70 |
| 43 | 380 | IIMISVFVL | 79 |
| 44 | 337 | YALDKFHPA | 87 |
| 45 | 302 | TMFILQEPI | 108 |
| 46 | 112 | ALAHGCVAL | 113 |
| 47 | 143 | FQVLSVLVV | 115 |
| 48 | 218 | MAYVDMATV | 119 |
| 49 | 225 | TVVCSILGV | 125 |
| 50 | 265 | GLTTALSMI | 164 |
| 51 | 357 | VAMVLQLLV | 196 |
| 52 | 230 | ILGVCLVMI | 259 |
| 53 | 345 | ALVSTVQHL | 261 |
| 54 | 360 | VLQLLVLHI | 357 |
| 55 | 217 | KMAYVDMAT | 527 |
| 56 | 211 | FLLVDEKMA | 882 |
| 57 | 234 | CLVMIPNIV | 1330 |
| 58 | 123 | RLVSDRSKV | 1792 |
| 59 | 247 | SLLNAWKEA | 2005 |
| 60 | 105 | WIVLFGSAL | 8810 |

TABLE 3b

HLA-A02 binding 10mer peptides derived from TMEM22

| SEQ ID NO | Start Position | amino acid sequence | Kd (nM) |
|---|---|---|---|
| 61 | 217 | KMAYvDMATV | 10 |
| 62 | 304 | FILQePIIPL | 10 |
| 63 | 212 | LLVDeKMAYV | 16 |
| 64 | 320 | YLIAiCVCST | 16 |
| 65 | 167 | RLFFyGVCNV | 18 |
| 66 | 338 | ALDKfHPALV | 18 |
| 67 | 363 | LLVLhIFPSI | 21 |
| 68 | 296 | TIWGiSTMFI | 45 |
| 69 | 112 | ALAHgCVALI | 50 |
| 70 | 103 | KMWIvLFGSA | 61 |
| 71 | 136 | LIFIrSVFQV | 66 |
| 72 | 265 | GLTTaLSMIV | 85 |
| 73 | 337 | YALDkFHPAL | 93 |
| 74 | 195 | TTMWRATTTV | 104 |
| 75 | 205 | FSAILAFLLV | 158 |
| 76 | 269 | ALSMIVYRSI | 169 |
| 77 | 229 | SILGvCLVMI | 174 |
| 78 | 148 | VLVVcYYQEA | 186 |
| 79 | 133 | SLELIFIRSV | 197 |
| 80 | 359 | MVLQlLVLHI | 210 |
| 81 | 380 | IIMISVFVLA | 218 |
| 82 | 224 | ATVVCSILGV | 219 |
| 83 | 356 | VVAMvLQLLV | 220 |
| 84 | 379 | VIIMiSVFVL | 226 |
| 85 | 291 | FGWTgTIWGI | 233 |
| 86 | 301 | STMFlLQEPI | 246 |
| 87 | 378 | GVIImISVFV | 257 |
| 88 | 302 | TMFIlQEPII | 257 |
| 89 | 287 | ALFTfGWTGT | 391 |
| 90 | 130 | KVPSlELIFI | 559 |

Start position indicates the number of amino acid residue from the N-terminus of TMEM22.
Dissociation constant [Kd (nM)] is derived from "NetMHC3.0".

CTL Induction with the Predicted Peptides from TMEM22 Restricted with HLA-A*0201

CTLs for those peptides derived from TMEM22 were generated according to the protocols as described in "Materials and Methods". Peptide specific CTL activity was determined by IFN-gamma ELISPOT assay (FIGS. 5a-1). The following well numbers demonstrated potent IFN-gamma production as compared to the control wells: well number #4 with TMEM22-A02-9-338 (SEQ ID NO: 35) (a), #2 with TMEM22-A02-9-381 (SEQ ID NO: 38) (b), #6 with TMEM22-A02-9-367 (SEQ ID NO: 41) (c), #3 with TMEM22-A02-9-218 (SEQ ID NO: 48) (d), #5 with TMEM22-A02-10-217 (SEQ ID NO: 61) (e), #8 with TMEM22-A02-10-304 (SEQ ID NO: 62) (f), #4 with TMEM22-A02-10-167 (SEQ ID NO: 65) (g), #6 with TMEM22-A02-10-363 (SEQ ID NO: 67) (h), #5 with TMEM22-A02-10-103 (SEQ ID NO: 70) (i), #5 with TMEM22-A02-10-195 (SEQ ID NO: 74) (j), #5 with TMEM22-A02-10-229 (SEQ ID NO: 77) (k) and #6 with TMEM22-A02-10-356 (SEQ ID NO: 83) (l). On the other hand, no specific CTL activity was determined by stimulation with other peptides shown in Tables 3a and 3b, despite those peptides had possible binding activity with HLA-A*0201. As is typical of negative data, specific IFN-gamma production was not observed from the CTL stimulated with TMEM22-A02-9-305 (SEQ ID NO: 33) (m). Thus, the results indicate that 12 peptides derived from TMEM22 were screened as the peptides that could induce potent CTLs.

Establishment of CTL Lines and Clones Against TMEM22 Derived Peptide

The cells that showed peptide specific CTL activity detected by IFN-gamma ELISPOT assay in the well number #4 with TMEM22-A02-9-338 (SEQ ID NO: 35) (a), #2 with TMEM22-A02-9-381 (SEQ ID NO: 38) (b), #3 with TMEM22-A02-9-218 (SEQ ID NO: 48) (c), #5 with TMEM22-A02-10-217 (SEQ ID NO: 61) (d), #8 with TMEM22-A02-10-304 (SEQ ID NO: 62) (e), #4 with TMEM22-A02-10-167 (SEQ ID NO: 65) (f), #6 with TMEM22-A02-10-363 (SEQ ID NO: 67) (g), #5 with TMEM22-A02-10-103 (SEQ ID NO: 70) (h), #5 with TMEM22-A02-10-195 (SEQ ID NO: 74) (i) and #6 with TMEM22-A02-10-356 (SEQ ID NO: 83) (j) were expanded and CTL lines were established by limiting dilution as described in "Materials and Methods" section above. CTL activity of these CTL lines was determined by IFN-gamma ELISA assay (FIGS. 6a-j). The CTL lines demonstrated potent IFN-gamma production against the target cells pulsed with the corresponding peptide as compared to target cells without peptide pulse. Furthermore, the CTL clones were established by limiting dilution from the CTL lines as described in "Materials and Methods", and IFN-gamma production from the CTL clones against target cells pulsed peptide was determined by IFN-gamma ELISA assay. Potent IFN-gamma productions were determined from the CTL clones stimulated with TMEM22-A02-9-381 (SEQ ID NO: 38) (a), TMEM22-A02-9-218 (SEQ ID NO: 48) (b), TMEM22-A02-10-217 (SEQ ID NO: 61) (c), TMEM22-A02-10-304 (SEQ ID NO: 62) (d), TMEM22-A02-10-167 (SEQ ID NO: 65) (e), TMEM22-A02-10-363 (SEQ ID NO: 67) (f), TMEM22-A02-10-103 (SEQ ID NO: 70) (g), TMEM22-A02-10-195 (SEQ ID NO: 74) (h) and TMEM22-A02-10-356 (SEQ ID NO: 83) (i). (FIGS. 7a-i).

Specific CTL Activity Against Target Cells Expressing TMEM22 and HLA-A*0201

The established CTL lines and clones raised against each peptide were examined for the ability to recognize target cells that express TMEM22 and HLA-A*0201 molecule. Specific CTL activity against COS7 cells which transfected with both the full length of TMEM22 and HLA-A*0201 gene (a specific model for the target cells that express TMEM22 and HLA-A*0201 gene) was tested by using the CTL lines and clones raised by corresponding peptide. COS7 cells transfected with either full length of TMEM22 or HLA-A* 0201 were prepared as the controls. In FIG. 8, the CTL clone stimulated with TMEM22-A02-10-195 (SEQ ID NO: 74) showed potent CTL activity against COS7 cells expressing both TMEM22 and HLA-A* 0201. On the other hand, no significant specific CTL activity was detected against the controls. Thus, these data clearly demonstrated that peptides of TMEM22-A02-10-195 (SEQ ID NO: 74) was endogenously processed and presented on the target cells with HLA-A*0201 molecule and were recognized by the CTLs. These results indicate that these peptides derived from TMEM22 may applicable to cancer vaccines for patients with TMEM22 ex-pressing tumors.

Homology Analysis of Antigen Peptides

The CTLs stimulated with TMEM22-A02-9-338 (SEQ ID NO: 35), TMEM22-A02-9-381 (SEQ ID NO: 38), TMEM22-A02-9-367 (SEQ ID NO: 41), TMEM22-A02-9-218 (SEQ ID NO: 48), TMEM22-A02-10-217 (SEQ ID NO: 61), TMEM22-A02-10-304 (SEQ ID NO: 62), TMEM22-A02-10-167 (SEQ ID NO: 65), TMEM22-A02-10-363 (SEQ ID NO: 67), TMEM22-A02-10-103 (SEQ ID NO: 70), TMEM22-A02-10-195 (SEQ ID NO: 74), TMEM22-A02-10-229 (SEQ ID NO: 77) and TMEM22-A02-10-356 (SEQ ID NO: 83) showed significant and specific CTL activity. This result may be due to the fact that the sequence of TMEM22-A02-9-338 (SEQ ID NO: 35), TMEM22-A02-9-381 (SEQ ID NO: 38), TMEM22-A02-9-367 (SEQ ID NO: 41), TMEM22-A02-9-218 (SEQ ID NO: 48), TMEM22-A02-10-217 (SEQ ID NO: 61), TMEM22-A02-10-304 (SEQ ID NO: 62), TMEM22-A02-10-167 (SEQ ID NO: 65), TMEM22-A02-10-363 (SEQ ID NO: 67), TMEM22-A02-10-103 (SEQ ID NO: 70), TMEM22-A02-10-195 (SEQ ID NO: 74), TMEM22-A02-10-229 (SEQ ID NO: 77) and TMEM22-A02-10-356 (SEQ ID NO: 83) are homologous to peptide derived from other molecules that are known to sensitize the human immune system. To exclude this possibility, homology analyses were performed for this peptide sequence using as queries the BLAST algorithm (www.ncbi.nlm.nih.gov/blast/blast.cgi) which revealed no sequence with significant homology. The results of homology analyses indicate that the following sequences are unique: TMEM22-A02-9-338 (SEQ ID NO: 35), TMEM22-A02-9-381 (SEQ ID NO: 38), TMEM22-A02-9-367 (SEQ ID NO: 41), TMEM22-A02-9-218 (SEQ ID NO: 48), TMEM22-A02-10-217 (SEQ ID NO: 61), TMEM22-A02-10-304 (SEQ ID NO: 62), TMEM22-A02-10-167 (SEQ ID NO: 65), TMEM22-A02-10-363 (SEQ ID NO: 67), TMEM22-A02-10-103 (SEQ ID NO: 70), TMEM22-A02-10-195 (SEQ ID NO: 74), TMEM22-A02-10-229 (SEQ ID NO: 77) and TMEM22-A02-10-356 (SEQ ID NO: 83). Thus, the possibility that these molecules can raise an unintended immunologic response to some unrelated molecule is remote.

In conclusion, novel HLA-A*0201 epitope peptides derived from TMEM22 were identified and demonstrated to be applicable for cancer immunotherapy.

INDUSTRIAL APPLICABILITY

The present invention provides new TAAs, particularly those derived from TMEM22 that induce potent and specific anti-tumor immune responses and have applicability to a wide array of cancer types. Such TAAs warrant further development as peptide vaccines against diseases associated with TMEM22, e.g., cancer, more particularly, AML, bladder cancer, CCC, esophagus cancer, lymphoma, prostate cancer, RCC and SCLC.

While the invention is herein described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention. Thus, the metes and bounds of the invention is intended to be defined not by the above description, but by the following claims and their equivalents.

The invention claimed is:

1. An isolated peptide of less than 15 amino acids selected from the group consisting of:
   (a) a peptide comprising the amino acid sequence as shown in SEQ ID NO: 74; and
   (b) a peptide comprising the amino acid sequence as shown in SEQ ID NO: 74, in which 1 or 2 amino acid(s) are substituted,
   wherein the peptide binds to an HLA-A2 antigen and has cytotoxic T lymphocyte (CTL) inducibility.

2. The isolated peptide of claim 1, which has one or both of the following characteristics:
   (a) the second amino acid from the N-terminus of the amino acid sequence of SEQ ID NO: 74 is substituted with an amino acid selected from the group consisting of leucine and methionine; and
   (b) the C-terminal amino acid of the amino acid sequence of SEQ ID NO: 74 is substituted with an amino acid selected from the group consisting of leucine and methionine; and
   (b) the C-terminal amino acid of the amino acid sequence of SEQ ID NO: 74 is substituted with leucine.

3. The isolated peptide of claim 1, wherein said peptide is a nonapeptide or decapeptide.

4. A composition for inducing CTL, wherein the composition comprises one or more peptide(s) of claim 1.

5. A pharmaceutical composition comprising one or more peptide(s) of claim 1 and an excipient.

6. The pharmaceutical composition of claim 5, wherein said composition is formulated for the administration to a subject whose HLA antigen is HLA-A2.

7. A method for inducing an antigen-presenting cell (APC) with CTL inducibility, wherein the method comprises
   contacting an APC with the peptide of claim 1 in vitro or ex vivo.

8. An in vitro method for inducing a CTL comprising at least one of the following steps:
   (a) co-culturing CD8-positive T cells with APCs, which APCs present on their surface a complex of an HLA antigen and the peptide of claim 1; and
   (b) co-culturing CD8-positive T cells with exosomes, which exosomes present on their surface a complex of an HLA antigen and the peptide of claim 1.

* * * * *

SEQUENCE LISTING

```
<160> NUMBER OF SEQ ID NOS: 96

<210> SEQ ID NO 1
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 1

Gly Tyr Lys Leu Tyr Trp Arg Asn Leu
1               5

<210> SEQ ID NO 2
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 2

Val Tyr Arg Ser Ile Lys Glu Lys Ile
1               5

<210> SEQ ID NO 3
<211> LENGTH: 9
```

```
<212> TYPE: PRT
<213> ORGANISM: Artificial Sequence
<220> FEATURE:
<223> OTHER INFORMATION: an artificially synthesized peptide sequence

<400> SEQUENCE: 3

Ile Tyr Asp Val Phe Gly Gly Val Ile
1               5

<210> SEQ ID NO 4
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 4

Ala Phe Leu Gly Val Tyr Tyr Ala Leu
1               5

<210> SEQ ID NO 5
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 5

Val Phe Val Leu Ala Gly Tyr Lys Leu
1               5

<210> SEQ ID NO 6
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 6

Val Phe Ser Ala Ile Leu Ala Phe Leu
1               5

<210> SEQ ID NO 7
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 7

Ile Phe Pro Ser Ile Tyr Asp Val Phe
1               5

<210> SEQ ID NO 8
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 8

Ala Phe Phe Gly Thr Met Asp Thr Leu
1               5

<210> SEQ ID NO 9
<211> LENGTH: 9
<212> TYPE: PRT
<213> ORGANISM: Artificial Sequence
```

```
<220> FEATURE:
<223> OTHER INFORMATION: an artificially synthesized peptide sequence

<400> SEQUENCE: 9

Gly Tyr Glu Glu Ile Asn Glu Gly Tyr
1               5

<210> SEQ ID NO 10
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 10

Ile Trp Gly Ile Ser Thr Met Phe Ile
1               5

<210> SEQ ID NO 11
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 11

Ile Phe Ile Arg Ser Val Phe Gln Val
1               5

<210> SEQ ID NO 12
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 12

Ile Phe Gln Ser Arg Lys Met Trp Ile
1               5

<210> SEQ ID NO 13
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 13

Met Trp Arg Ala Thr Thr Thr Val Phe
1               5

<210> SEQ ID NO 14
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 14

Ser Met Trp Thr Ala Leu Phe Thr Phe
1               5

<210> SEQ ID NO 15
<211> LENGTH: 9
<212> TYPE: PRT
<213> ORGANISM: Artificial Sequence
<220> FEATURE:
<223> OTHER INFORMATION: an artificially synthesized peptide sequence
```

```
<400> SEQUENCE: 15

Val Phe Gln Val Leu Ser Val Leu Val
1               5

<210> SEQ ID NO 16
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 16

Val Phe Gly Gly Val Ile Ile Met Ile
1               5

<210> SEQ ID NO 17
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 17

Lys Tyr Pro Val Lys Lys Arg Val Lys Ile
1               5                   10

<210> SEQ ID NO 18
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 18

Ile Phe Ile Arg Ser Val Phe Gln Val Leu
1               5                   10

<210> SEQ ID NO 19
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 19

Arg Ser Val Phe Gln Val Leu Ser Val Leu
1               5                   10

<210> SEQ ID NO 20
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 20

Tyr Tyr Gln Glu Ala Pro Phe Gly Pro Ser
1               5                   10

<210> SEQ ID NO 21
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 21
```

Phe Tyr Gly Val Cys Asn Val Ile Ser Ile
1               5                   10

<210> SEQ ID NO 22
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 22

Val Phe Ser Ala Ile Leu Ala Phe Leu Leu
1               5                   10

<210> SEQ ID NO 23
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 23

Gly Tyr Thr Met Thr Val Met Ala Gly Leu
1               5                   10

<210> SEQ ID NO 24
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 24

Ser Tyr Leu Ile Ala Ile Cys Val Cys Ser
1               5                   10

<210> SEQ ID NO 25
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 25

Ile Val Val Ala Met Val Leu Gln Leu Leu
1               5                   10

<210> SEQ ID NO 26
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 26

Ile Tyr Asp Val Phe Gly Gly Val Ile Ile
1               5                   10

<210> SEQ ID NO 27
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 27

Asp Tyr Gln Glu Ile Leu Asp Ser Pro Ile

```
<210> SEQ ID NO 28
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 28

Ile Ser Met Trp Thr Ala Leu Phe Thr Phe
1               5                   10

<210> SEQ ID NO 29
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 29

Ile Trp Gly Ile Ser Thr Met Phe Ile Leu
1               5                   10

<210> SEQ ID NO 30
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 30

Met Trp Ile Val Leu Phe Gly Ser Ala Leu
1               5                   10

<210> SEQ ID NO 31
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 31

Ile Ser Ile Thr Cys Ala Tyr Thr Ser Phe
1               5                   10

<210> SEQ ID NO 32
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 32

Thr Met Trp Arg Ala Thr Thr Thr Val
1               5

<210> SEQ ID NO 33
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 33

Ile Leu Gln Glu Pro Ile Ile Pro Leu
1               5
```

```
<210> SEQ ID NO 34
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 34

Val Met Ala Gly Leu Thr Thr Ala Leu
1               5

<210> SEQ ID NO 35
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 35

Ala Leu Asp Lys Phe His Pro Ala Leu
1               5

<210> SEQ ID NO 36
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 36

Leu Val Asp Glu Lys Met Ala Tyr Val
1               5

<210> SEQ ID NO 37
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 37

Val Ile Ile Met Ile Ser Val Phe Val
1               5

<210> SEQ ID NO 38
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 38

Ile Met Ile Ser Val Phe Val Leu Ala
1               5

<210> SEQ ID NO 39
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 39

Leu Val Leu His Ile Phe Pro Ser Ile
1               5

<210> SEQ ID NO 40
```

```
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 40

Tyr Leu Ile Ala Ile Cys Val Cys Ser
1               5

<210> SEQ ID NO 41
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 41

His Ile Phe Pro Ser Ile Tyr Asp Val
1               5

<210> SEQ ID NO 42
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 42

Phe Gln Ser Arg Lys Met Trp Ile Val
1               5

<210> SEQ ID NO 43
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 43

Ile Ile Met Ile Ser Val Phe Val Leu
1               5

<210> SEQ ID NO 44
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 44

Tyr Ala Leu Asp Lys Phe His Pro Ala
1               5

<210> SEQ ID NO 45
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 45

Thr Met Phe Ile Leu Gln Glu Pro Ile
1               5

<210> SEQ ID NO 46
<211> LENGTH: 9
<212> TYPE: PRT
```

```
<213> ORGANISM: Artificial Sequence
<220> FEATURE:
<223> OTHER INFORMATION: an artificially synthesized peptide sequence

<400> SEQUENCE: 46

Ala Leu Ala His Gly Cys Val Ala Leu
1               5

<210> SEQ ID NO 47
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 47

Phe Gln Val Leu Ser Val Leu Val Val
1               5

<210> SEQ ID NO 48
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 48

Met Ala Tyr Val Asp Met Ala Thr Val
1               5

<210> SEQ ID NO 49
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 49

Thr Val Val Cys Ser Ile Leu Gly Val
1               5

<210> SEQ ID NO 50
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 50

Gly Leu Thr Thr Ala Leu Ser Met Ile
1               5

<210> SEQ ID NO 51
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 51

Val Ala Met Val Leu Gln Leu Leu Val
1               5

<210> SEQ ID NO 52
<211> LENGTH: 9
<212> TYPE: PRT
<213> ORGANISM: Artificial Sequence
<220> FEATURE:
```

<223> OTHER INFORMATION: an artificially synthesized peptide sequence

<400> SEQUENCE: 52

Ile Leu Gly Val Cys Leu Val Met Ile
1               5

<210> SEQ ID NO 53
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 53

Ala Leu Val Ser Thr Val Gln His Leu
1               5

<210> SEQ ID NO 54
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 54

Val Leu Gln Leu Leu Val Leu His Ile
1               5

<210> SEQ ID NO 55
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 55

Lys Met Ala Tyr Val Asp Met Ala Thr
1               5

<210> SEQ ID NO 56
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 56

Phe Leu Leu Val Asp Glu Lys Met Ala
1               5

<210> SEQ ID NO 57
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 57

Cys Leu Val Met Ile Pro Asn Ile Val
1               5

<210> SEQ ID NO 58
<211> LENGTH: 9
<212> TYPE: PRT
<213> ORGANISM: Artificial Sequence
<220> FEATURE:
<223> OTHER INFORMATION: an artificially synthesized peptide sequence -continued

```
<400> SEQUENCE: 58

Arg Leu Val Ser Asp Arg Ser Lys Val
1               5

<210> SEQ ID NO 59
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 59

Ser Leu Leu Asn Ala Trp Lys Glu Ala
1               5

<210> SEQ ID NO 60
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 60

Trp Ile Val Leu Phe Gly Ser Ala Leu
1               5

<210> SEQ ID NO 61
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 61

Lys Met Ala Tyr Val Asp Met Ala Thr Val
1               5                   10

<210> SEQ ID NO 62
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 62

Phe Ile Leu Gln Glu Pro Ile Ile Pro Leu
1               5                   10

<210> SEQ ID NO 63
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 63

Leu Leu Val Asp Glu Lys Met Ala Tyr Val
1               5                   10

<210> SEQ ID NO 64
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 64
```

```
Tyr Leu Ile Ala Ile Cys Val Cys Ser Thr
1               5                   10

<210> SEQ ID NO 65
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 65

Arg Leu Phe Phe Tyr Gly Val Cys Asn Val
1               5                   10

<210> SEQ ID NO 66
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 66

Ala Leu Asp Lys Phe His Pro Ala Leu Val
1               5                   10

<210> SEQ ID NO 67
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 67

Leu Leu Val Leu His Ile Phe Pro Ser Ile
1               5                   10

<210> SEQ ID NO 68
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 68

Thr Ile Trp Gly Ile Ser Thr Met Phe Ile
1               5                   10

<210> SEQ ID NO 69
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 69

Ala Leu Ala His Gly Cys Val Ala Leu Ile
1               5                   10

<210> SEQ ID NO 70
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 70

Lys Met Trp Ile Val Leu Phe Gly Ser Ala
1               5                   10
```

```
<210> SEQ ID NO 71
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 71

Leu Ile Phe Ile Arg Ser Val Phe Gln Val
1               5                   10

<210> SEQ ID NO 72
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 72

Gly Leu Thr Thr Ala Leu Ser Met Ile Val
1               5                   10

<210> SEQ ID NO 73
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 73

Tyr Ala Leu Asp Lys Phe His Pro Ala Leu
1               5                   10

<210> SEQ ID NO 74
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 74

Thr Thr Met Trp Arg Ala Thr Thr Thr Val
1               5                   10

<210> SEQ ID NO 75
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 75

Phe Ser Ala Ile Leu Ala Phe Leu Leu Val
1               5                   10

<210> SEQ ID NO 76
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 76

Ala Leu Ser Met Ile Val Tyr Arg Ser Ile
1               5                   10
```

```
<210> SEQ ID NO 77
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 77

Ser Ile Leu Gly Val Cys Leu Val Met Ile
1               5                   10

<210> SEQ ID NO 78
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 78

Val Leu Val Val Cys Tyr Tyr Gln Glu Ala
1               5                   10

<210> SEQ ID NO 79
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 79

Ser Leu Glu Leu Ile Phe Ile Arg Ser Val
1               5                   10

<210> SEQ ID NO 80
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 80

Met Val Leu Gln Leu Leu Val Leu His Ile
1               5                   10

<210> SEQ ID NO 81
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 81

Ile Ile Met Ile Ser Val Phe Val Leu Ala
1               5                   10

<210> SEQ ID NO 82
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 82

Ala Thr Val Val Cys Ser Ile Leu Gly Val
1               5                   10

<210> SEQ ID NO 83
<211> LENGTH: 10
```

```
<212> TYPE: PRT
<213> ORGANISM: Artificial Sequence
<220> FEATURE:
<223> OTHER INFORMATION: an artificially synthesized peptide sequence

<400> SEQUENCE: 83

Val Val Ala Met Val Leu Gln Leu Leu Val
1               5                   10

<210> SEQ ID NO 84
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 84

Val Ile Ile Met Ile Ser Val Phe Val Leu
1               5                   10

<210> SEQ ID NO 85
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 85

Phe Gly Trp Thr Gly Thr Ile Trp Gly Ile
1               5                   10

<210> SEQ ID NO 86
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 86

Ser Thr Met Phe Ile Leu Gln Glu Pro Ile
1               5                   10

<210> SEQ ID NO 87
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 87

Gly Val Ile Ile Met Ile Ser Val Phe Val
1               5                   10

<210> SEQ ID NO 88
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 88

Thr Met Phe Ile Leu Gln Glu Pro Ile Ile
1               5                   10

<210> SEQ ID NO 89
<211> LENGTH: 10
<212> TYPE: PRT
<213> ORGANISM: Artificial Sequence
```

-continued

<220> FEATURE:
<223> OTHER INFORMATION: an artificially synthesized peptide sequence

<400> SEQUENCE: 89

Ala Leu Phe Thr Phe Gly Trp Thr Gly Thr
1               5                   10

<210> SEQ ID NO 90
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 90

Lys Val Pro Ser Leu Glu Leu Ile Phe Ile
1               5                   10

<210> SEQ ID NO 91
<211> LENGTH: 2079
<212> TYPE: DNA
<213> ORGANISM: Homo sapiens

<400> SEQUENCE: 91

```
cccgcagtct ccaactccgg cgccagtcag gttgtggggt gggggcggcg gagggcggag      60
agcgcaggcg cagagtccgc gcggcggcgc ccctctccct ccgcagtact ccgggcagcg     120
cccgcctcga ttttcccagg cgagggcacg cccgcgtcag tcgcctccgg ggcaccttcc     180
tcgccacgac acgcaggtaa ccgggccccg ggagccggtc ggcggcggcg gactgggacc     240
ttgatcctgc ctgcccggcc gcccgacaag ggaatgagag cggaccccga actccacaca     300
cccgcgttta gccgccacac ctaaggggca aacagtcttt ttgggtaagg gccgggctg      360
ggggcgacgc gccccgcccg cttttgcagac ttcggggtgc tctgcacgac gcctgaaagg     420
ccgcggggcc cgcatttctc tgtgctgccc tcctggagaa ccgggacacg gggacgggag     480
ggccagcatc ggctacggcc cggtttcccg tttctttccg ctgtcgcgtg tctgggccct     540
cctgcagcgt ccatgatgaa ggccaggggc tgttgctttc ctctcgccca gtagccaacc     600
caagcaaggg aattgattat ctgaagaaat ggatacttct ccctccagaa aatatccagt     660
taaaaacgg gtgaaaatac atcccaacac agtgatggtg aaatatactt ctcattatcc      720
ccagcctggc gatgatggat atgaagaaat caatgaaggc tatggaaatt ttatggagga     780
aaatccaaag aaaggtctgc tgagtgaaat gaaaaaaaaa gggagagctt ctttggaac     840
catggatacc ctacctccac caacagaaga cccaatgatc aatgagattg acaattcca     900
gagctttgca gaaaaaaaca ttttttcaatc ccgaaaatg tggatagtgc tgtttggatc    960
tgctttggct catggatgtg tagctcttat cactaggctt gtttctgatc ggtctaaagt    1020
tccatctcta gaactgattt ttatccgttc tgttttttcag gtcttatctg tgttagttgt    1080
gtgttactat caggaggccc cctttggacc cagtggatac agattacgac tcttcttta    1140
tggtgtatgc aatgtcattt ctatcacttg tgcttataca tcattttcaa tagttcctcc    1200
cagcaatggg accactatgt ggagagccac aactacagtc ttcagtgcca ttttggcttt    1260
tttactcgta gatgagaaaa tggcttatgt tgacatggct acagttgttt gcagcatctt    1320
aggtgttgt cttgtcatga tcccaaacat tgttgatgaa acaattctt tgttaaatgc    1380
ctggaaagaa gcctttgggt acaccatgac tgtgatggct ggactgacca ctgctctctc    1440
aatgatagta tacagatcca tcaaggagaa gatcagcatg tggactgcac tgtttacttt    1500
tggttggact gggacaattt ggggaatatc tactatgttt attcttcaag aacccatcat    1560
```

-continued

```
cccattagat ggagaaacct ggagttatct cattgctata tgtgtctgtt ctactgcagc      1620
attcttagga gtttattatg ccttggacaa attccatcca gctttggtta gcacagtaca      1680
acatttggag attgtggtag ctatggtctt gcagcttctc gtgctgcaca tatttcctag      1740
catctatgat gttttttggag gggtaatcat tatgattagt gttttttgtcc ttgctggcta     1800 taaactttac tggaggaatt taagaaagca ggactaccag gaaatactag actctcccat      1860
taaatgaata cctgattatt attgtctcat taatgttcag ttattatgta tactgccatt      1920
ttaatgttta cctatgaatg tcttttgtgt tatataactg acagagtgct ataaaatata      1980
taatatatac aaatgcagaa aatttattct agtctaatat attcaaatac aaatattaaa      2040
tatatgaaat acgttatgaa aaaaaaaaaa aaaaaaaa                              2079
```

<210> SEQ ID NO 92
<211> LENGTH: 412
<212> TYPE: PRT
<213> ORGANISM: Homo sapiens

<400> SEQUENCE: 92

```
Met Asp Thr Ser Pro Ser Arg Lys Tyr Pro Val Lys Lys Arg Val Lys
1               5                   10                  15

Ile His Pro Asn Thr Val Met Val Lys Tyr Thr Ser His Tyr Pro Gln
            20                  25                  30

Pro Gly Asp Asp Gly Tyr Glu Glu Ile Asn Glu Gly Tyr Gly Asn Phe
        35                  40                  45

Met Glu Glu Asn Pro Lys Lys Gly Leu Leu Ser Glu Met Lys Lys Lys
    50                  55                  60

Gly Arg Ala Phe Phe Gly Thr Met Asp Thr Leu Pro Pro Thr Glu
65                  70                  75                  80

Asp Pro Met Ile Asn Glu Ile Gly Gln Phe Gln Ser Phe Ala Glu Lys
                85                  90                  95

Asn Ile Phe Gln Ser Arg Lys Met Trp Ile Val Leu Phe Gly Ser Ala
            100                 105                 110

Leu Ala His Gly Cys Val Ala Leu Ile Thr Arg Leu Val Ser Asp Arg
        115                 120                 125

Ser Lys Val Pro Ser Leu Glu Leu Ile Phe Ile Arg Ser Val Phe Gln
    130                 135                 140

Val Leu Ser Val Leu Val Val Cys Tyr Tyr Gln Glu Ala Pro Phe Gly
145                 150                 155                 160

Pro Ser Gly Tyr Arg Leu Arg Leu Phe Phe Tyr Gly Val Cys Asn Val
                165                 170                 175

Ile Ser Ile Thr Cys Ala Tyr Thr Ser Phe Ser Ile Val Pro Pro Ser
            180                 185                 190

Asn Gly Thr Thr Met Trp Arg Ala Thr Thr Thr Val Phe Ser Ala Ile
        195                 200                 205

Leu Ala Phe Leu Leu Val Asp Glu Lys Met Ala Tyr Val Asp Met Ala
    210                 215                 220

Thr Val Val Cys Ser Ile Leu Gly Val Cys Leu Val Met Ile Pro Asn
225                 230                 235                 240

Ile Val Asp Glu Asp Asn Ser Leu Leu Asn Ala Trp Lys Glu Ala Phe
                245                 250                 255

Gly Tyr Thr Met Thr Val Met Ala Gly Leu Thr Thr Ala Leu Ser Met
            260                 265                 270

Ile Val Tyr Arg Ser Ile Lys Glu Lys Ile Ser Met Trp Thr Ala Leu
        275                 280                 285
```

```
Phe Thr Phe Gly Trp Thr Gly Thr Ile Trp Gly Ile Ser Thr Met Phe
    290                 295                 300

Ile Leu Gln Glu Pro Ile Ile Pro Leu Asp Gly Glu Thr Trp Ser Tyr
305                 310                 315                 320

Leu Ile Ala Ile Cys Val Cys Ser Thr Ala Ala Phe Leu Gly Val Tyr
                325                 330                 335

Tyr Ala Leu Asp Lys Phe His Pro Ala Leu Val Ser Thr Val Gln His
                340                 345                 350

Leu Glu Ile Val Val Ala Met Val Leu Gln Leu Leu Val Leu His Ile
            355                 360                 365

Phe Pro Ser Ile Tyr Asp Val Phe Gly Gly Val Ile Ile Met Ile Ser
    370                 375                 380

Val Phe Val Leu Ala Gly Tyr Lys Leu Tyr Trp Arg Asn Leu Arg Lys
385                 390                 395                 400

Gln Asp Tyr Gln Glu Ile Leu Asp Ser Pro Ile Lys
                405                 410

<210> SEQ ID NO 93
<211> LENGTH: 22
<212> TYPE: DNA
<213> ORGANISM: Artificial Sequence
<220> FEATURE:
<223> OTHER INFORMATION: An artificially synthesized sequence

<400> SEQUENCE: 93
gtctaccagg cattcgcttc at                                              22

<210> SEQ ID NO 94
<211> LENGTH: 24
<212> TYPE: DNA
<213> ORGANISM: Artificial Sequence
<220> FEATURE:
<223> OTHER INFORMATION: An artificially synthesized sequence

<400> SEQUENCE: 94
tcagctggac cacagccgca gcgt                                            24

<210> SEQ ID NO 95
<211> LENGTH: 21
<212> TYPE: DNA
<213> ORGANISM: Artificial Sequence
<220> FEATURE:
<223> OTHER INFORMATION: An artificially synthesized sequence

<400> SEQUENCE: 95
tcagaaatcc tttctcttga c                                               21

<210> SEQ ID NO 96
<211> LENGTH: 24
<212> TYPE: DNA
<213> ORGANISM: Artificial Sequence
<220> FEATURE:
<223> OTHER INFORMATION: An artificially synthesized sequence

<400> SEQUENCE: 96
ctagcctctg gaatcctttc tctt                                            24
```